(12) United States Patent
Young et al.

(10) Patent No.: US 7,700,735 B2
(45) Date of Patent: Apr. 20, 2010

(54) HIGH POTENCY RECOMBINANT ANTIBODIES AND METHOD FOR PRODUCING THEM

(75) Inventors: James F. Young, Darnestown, MD (US); Leslie S. Johnson, Germantown, MD (US); William D. Huse, Del Mar, CA (US); Herron Wu, Houston, TX (US); Jeffrey D. Watkins, Encinitis, CA (US)

(73) Assignee: MedImmune, LLC, Gaithersburg, MD (US)

( * ) Notice: Subject to any disclaimer, the term of this patent is extended or adjusted under 35 U.S.C. 154(b) by 162 days.

(21) Appl. No.: 09/796,848

(22) Filed: Mar. 1, 2001

(65) Prior Publication Data

US 2002/0098189 A1 Jul. 25, 2002

Related U.S. Application Data

(60) Provisional application No. 60/186,252, filed on Mar. 1, 2000.

(51) Int. Cl.
*C07K 16/10* (2006.01)
*A61K 39/42* (2006.01)

(52) U.S. Cl. .............. 530/387.1; 530/387.3; 530/388.1; 530/388.3; 424/130.1; 424/141.1; 424/147.1

(58) Field of Classification Search .............. 424/130.1, 424/133.1, 134.1, 135.1, 147.1; 435/7.1; 530/388.3, 387.1, 387.3, 388.1, 389.1, 387.5
See application file for complete search history.

(56) References Cited

U.S. PATENT DOCUMENTS

| | | | |
|---|---|---|---|
| 4,517,304 A | 5/1985 | Stott et al. | |
| 4,526,938 A | 7/1985 | Churchill et al. | |
| 4,659,563 A | 4/1987 | Dobkin | |
| 4,717,766 A | 1/1988 | Dobkin | |
| 4,760,026 A | 7/1988 | Lennox et al. | |
| 4,800,078 A | 1/1989 | Prince et al. | |
| 4,853,326 A | 8/1989 | Quash et al. | |
| 4,880,078 A | 11/1989 | Inoue et al. | |
| 4,917,893 A | 4/1990 | Okada et al. | |
| 5,071,758 A | 12/1991 | Stott et al. | |
| 5,128,326 A | 7/1992 | Balazs et al. | |
| 5,137,804 A | 8/1992 | Greene et al. | |
| 5,149,650 A | 9/1992 | Wertz et al. | |
| 5,183,657 A | 2/1993 | Buurman | |
| 5,194,595 A | 3/1993 | Wathen | |
| 5,219,996 A | 6/1993 | Bodmer et al. | |
| 5,223,254 A | 6/1993 | Paradiso et al. | |
| 5,223,409 A | 6/1993 | Ladner et al. | |
| 5,240,694 A | 8/1993 | Gwaltney, Jr. | |
| 5,271,927 A | 12/1993 | Parker et al. | |
| 5,279,935 A | 1/1994 | Nycz | |
| 5,288,630 A | 2/1994 | Wathen | |
| 5,290,540 A | 3/1994 | Prince et al. | |
| 5,332,567 A | 7/1994 | Goldenberg | |
| 5,332,805 A | 7/1994 | Carey et al. | |
| 5,340,926 A | 8/1994 | Lowe et al. | |
| 5,354,554 A | 10/1994 | Rhind | |
| 5,391,478 A | 2/1995 | Greene et al. | |
| 5,403,484 A | 4/1995 | Ladner et al. | |
| 5,411,749 A | 5/1995 | Mayo et al. | |
| 5,412,077 A | 5/1995 | Siber et al. | |
| 5,418,136 A | 5/1995 | Miller et al. | |
| 5,422,097 A | 6/1995 | Gwaltney, Jr. | |
| 5,424,189 A | 6/1995 | Oberst et al. | |
| 5,468,606 A | 11/1995 | Bogart et al. | |
| 5,470,736 A | 11/1995 | Verma et al. | |
| 5,476,997 A | 12/1995 | Kaneshima et al. | |
| 5,484,893 A | 1/1996 | Parker et al. | |
| 5,496,703 A * | 3/1996 | Babish et al. .............. 435/7.21 |
| 5,506,209 A | 4/1996 | Mukerji et al. | |
| 5,518,725 A | 5/1996 | Daynes et al. | |
| 5,530,102 A | 6/1996 | Gristina et al. | |
| 5,534,411 A | 7/1996 | Weltzin et al. | |
| 5,538,733 A | 7/1996 | Emery et al. | |
| 5,538,952 A | 7/1996 | Mukerji et al. | |
| 5,571,698 A | 11/1996 | Ladner et al. | |

(Continued)

FOREIGN PATENT DOCUMENTS

AU 713113 11/1999

(Continued)

OTHER PUBLICATIONS

J. of Molecular Recognition 1999, vol. 12 pp. 390-408.*

(Continued)

*Primary Examiner*—Mary E Mosher
*Assistant Examiner*—Myron G Hill
(74) *Attorney, Agent, or Firm*—Jones Day

(57) ABSTRACT

High potency antibodies, including immunologically active fragments thereof, having high kinetic association rate constants and optional high affinities are disclosed, along with methods for producing such antibodies. The high potency antibodies disclosed herein are of either the neutralizing or non-neutralizing type and have specificity for antigens displayed by microorganisms, especially viruses, as well as antigenic sites present on cancer cells and on various types of toxins, and the products of toxins. Processes for producing high potency neutralizing antibodies and increasing the potency of already existing neutralizing antibodies are also described. Methods of using said antibodies in the prevention and/or treatment of diseases, especially diseases induced or caused by viruses, are disclosed.

38 Claims, 5 Drawing Sheets

U.S. PATENT DOCUMENTS

| | | | |
|---|---|---|---|
| 5,585,089 A | 12/1996 | Queen et al. | 424/133.1 |
| 5,624,821 A | 4/1997 | Winter | |
| 5,648,260 A | 7/1997 | Winter | |
| 5,667,988 A | 9/1997 | Barbas et al. | 435/69.1 |
| 5,679,377 A | 10/1997 | Bernstein et al. | |
| 5,693,762 A | 12/1997 | Queen et al. | 530/387 |
| 5,762,905 A | 6/1998 | Burton et al. | |
| 5,811,524 A | 9/1998 | Brams et al. | |
| 5,824,307 A * | 10/1998 | Johnson | 424/133.1 |
| 5,840,298 A | 11/1998 | Brams et al. | |
| 5,855,913 A | 1/1999 | Hanes et al. | |
| 5,866,125 A | 2/1999 | Brams et al. | |
| 5,874,064 A | 2/1999 | Edwards et al. | |
| 5,912,015 A | 6/1999 | Bernstein et al. | |
| 5,916,597 A | 6/1999 | Lee et al. | |
| 5,929,212 A | 7/1999 | Adair et al. | |
| 5,934,272 A | 8/1999 | Lloyd et al. | |
| 5,939,068 A | 8/1999 | Brams et al. | |
| 5,955,364 A | 9/1999 | Brams et al. | |
| 5,958,765 A | 9/1999 | Brams et al. | |
| 5,985,309 A | 11/1999 | Edwards et al. | |
| 5,985,320 A | 11/1999 | Edwards et al. | |
| 5,989,463 A | 11/1999 | Tracy et al. | |
| 6,019,968 A | 2/2000 | Platz et al. | |
| 6,096,551 A | 8/2000 | Barbas et al. | |
| 6,117,980 A | 9/2000 | Gonzalez et al. | |
| 6,121,022 A | 9/2000 | Presta | |
| 6,194,551 B1 | 2/2001 | Idusogie | |
| 6,277,375 B1 | 8/2001 | Ward | |
| 6,413,771 B1 | 7/2002 | Brams et al. | |
| 6,519,948 B2 | 2/2003 | Zorn | |
| 6,528,624 B1 | 3/2003 | Idusogie | |
| 6,537,809 B2 | 3/2003 | Brams et al. | |
| 6,538,124 B1 | 3/2003 | Idusogie | |
| 6,565,849 B2 | 5/2003 | Koenig | |
| 6,565,888 B1 | 5/2003 | Tracy et al. | |
| 6,572,856 B1 | 6/2003 | Taylor et al. | |
| 6,656,467 B2 * | 12/2003 | Young et al. | 424/147.1 |
| 6,685,942 B1 | 2/2004 | Burton et al. | |
| 6,737,056 B1 | 5/2004 | Presta | |
| 6,818,216 B2 | 11/2004 | Young et al. | |
| 6,855,493 B2 | 2/2005 | Young et al. | |
| 7,083,784 B2 | 8/2006 | Dall'Acqua | |
| 7,132,100 B2 | 11/2006 | Oliver et al. | |
| 7,179,900 B2 | 2/2007 | Young et al. | |
| 7,208,162 B2 | 4/2007 | Prince et al. | |
| 7,229,619 B1 | 6/2007 | Young et al. | |
| 7,294,336 B2 | 11/2007 | Oliver et al. | |
| 7,323,172 B2 | 1/2008 | Young et al. | |
| 7,416,726 B2 | 8/2008 | Ravetch | |
| 7,425,618 B2 | 9/2008 | Oliver et al. | |
| 7,553,489 B2 | 6/2009 | Young et al. | |
| 2001/0026798 A1 | 10/2001 | Koenig | |
| 2001/0034062 A1 | 10/2001 | Koenig | |
| 2002/0001798 A1 | 1/2002 | Brams et al. | |
| 2002/0004046 A1 | 1/2002 | Johnson | |
| 2002/0018780 A1 | 2/2002 | Koenig et al. | |
| 2002/0051787 A1 | 5/2002 | Prince et al. | |
| 2002/0098189 A1 | 7/2002 | Young et al. | |
| 2002/0102257 A1 | 8/2002 | Johnson | |
| 2004/0002587 A1 | 1/2004 | Watkins | |
| 2004/0005323 A1 | 1/2004 | Brams et al. | |
| 2004/0005324 A1 | 1/2004 | Pilkington et al. | |
| 2004/0076631 A1 | 4/2004 | Brams et al. | |
| 2004/0131609 A1 | 7/2004 | Young et al. | |
| 2005/0002926 A1 | 1/2005 | Young et al. | |
| 2005/0147616 A1 | 7/2005 | Young et al. | |
| 2006/0099220 A1 | 5/2006 | Tous et al. | |
| 2006/0115485 A1 | 6/2006 | Losonsky et al. | |
| 2006/0198840 A1 | 9/2006 | Dall'Acqua et al. | |
| 2007/0122403 A1 | 5/2007 | Dall'Acqua et al. | |
| 2007/0196916 A1 | 8/2007 | Young et al. | |
| 2008/0286270 A1 | 11/2008 | Oliver et al. | |
| 2009/0175883 A1 | 7/2009 | Oliver et al. | |

FOREIGN PATENT DOCUMENTS

| | | |
|---|---|---|
| AU | 2002219944 | 2/2008 |
| CA | 2197684 | 2/1996 |
| CA | 2197684 | 10/2000 |
| EP | 0327378 | 8/1989 |
| EP | 0368684 | 5/1990 |
| EP | 0413622 | 2/1991 |
| EP | 0671927 | 9/1995 |
| EP | 0682040 | 11/1995 |
| EP | 0451216 | 1/1996 |
| EP | 699 756 A1 | 6/1996 |
| EP | 0327378 | 12/1996 |
| EP | 1265928 | 12/2002 |
| FR | 2758331 | 7/1998 |
| JP | 1268646 A | 10/1989 |
| WO | WO 90/07861 | 7/1990 |
| WO | WO 91/05548 | 5/1991 |
| WO | WO 92/05274 | 4/1992 |
| WO | WO 92/19244 | 11/1992 |
| WO | WO 93/05796 | 4/1993 |
| WO | WO 93/15199 | 8/1993 |
| WO | WO 93/15200 | 8/1993 |
| WO | WO 93/19197 | 9/1993 |
| WO | WO 93/20210 | 10/1993 |
| WO | WO 94/06448 | 3/1994 |
| WO | WO 94/29351 | 12/1994 |
| WO | WO 95/04081 | 2/1995 |
| WO | WO 96/05229 | 2/1996 |
| WO | WO 96/20698 | 7/1996 |
| WO | WO 96/40252 | 12/1996 |
| WO | WO 97/32572 | 9/1997 |
| WO | WO 97/34631 | 9/1997 |
| WO | WO 97/44013 | 11/1997 |
| WO | WO 98/23289 | 6/1998 |
| WO | WO 98/31346 | 7/1998 |
| WO | WO 98/33919 | 8/1998 |
| WO | WO 99/15154 | 4/1999 |
| WO | WO 99/20253 | 4/1999 |
| WO | WO 99/28471 | 6/1999 |
| WO | WO 99/51642 | 10/1999 |
| WO | WO 99/66903 | 12/1999 |
| WO | WO 00/29584 | 5/2000 |
| WO | WO 00/42072 | 7/2000 |
| WO | WO 00/56771 | 9/2000 |
| WO | WO 00/73346 | 12/2000 |
| WO | WO 01/55217 A | 8/2001 |
| WO | WO 01/58957 | 8/2001 |
| WO | WO 01/64751 A | 9/2001 |
| WO | WO 01/77137 | 10/2001 |
| WO | WO 02/060919 | 12/2001 |
| WO | WO 02/060919 | 8/2002 |
| WO | WO 03/054213 | 7/2003 |
| WO | WO 2004/010935 | 2/2004 |
| WO | WO 2004/016750 | 2/2004 |
| WO | WO 2004/029207 | 4/2004 |
| WO | WO 2004/035752 | 4/2004 |
| WO | WO 2004/083373 | 9/2004 |
| WO | WO 2006/034292 | 3/2006 |
| WO | WO 2007/002543 | 1/2007 |
| WO | WO 2009/003019 | 12/2008 |

OTHER PUBLICATIONS

Yang ,J of Molecular Biology 1995 vol. 254, pp. 392-403.*
Myszka ,J. of Molecular Recognition 1999, vol. 12 pp. 390-408.*
Talwar et al. PNAS 1976, vol. 73, No. 1, pp. 218-222.*
Schier, et al., Isolation of High-affinity Monomeric Human Anti-c-erbB-2 Single chain Fv Using Affinity-driven Selection, Journal of Molecular Biology 1996, vol. 255, Issue 1, pp. 28-43.*

Sakurai, et al., Antibody Responses to Mature and Immature Forms of Viral Envelope in Respiratory Syncytial Virus Infection: Significance for Subunit Vaccines J. Virol. 1999 73: 2956-2962.*

Hefta LJ, Immunotechnology. Jun. 1998;4(1):49-57. Kinetic and affinity constants of epitop specific anti-carcinoembryonic antigen (CEA) monoclonal antibodies for CEA and engineered CEA domain constructs.*

Laura J.F. Hefta, et al, "Kinetic and Affinity Constants of Epitope Specific Anti-Carcinembryonic Antigen (CEA) Monoclonal Antibodies for CEA and Engineered CEA Domain Constructs," Immunotechnology 4, pp. 49-57, Feb. 23, 1998.

Herren Wu, et al, "Humanization of Murine Monoclonal Antibody by Simultaneous Optimization of Framework and CDR Residues," Journal of Molecular Biology, Article No: jmbl., pp. 3141, Aug. 26, 1999.

Yang, Wei-Ping, et al, "CDR Walking Mutagenesis for the Affinity Maturation of a Potent Human Anit-HIV-1 Antibody into the Picomolar Range," Journal of Molecular Biology, Article No: J. Mol. Biol., pp. 254, 392-403, Sep. 5, 1995.

Schier, et al., Isolation of Picomolar Affinity Anti-c-erbB-2 Single-chain Fv by Molecular Evolution of the Complementarity Determining Regions . . . :, Academic Press Limited, pp. 551-567(1996).

Newman, et al., "Primatization" of Recombinant Antibodies for Immunotherapy of Human Diseases: A Macaque/Hunab Chimeric Antibody Against Human CD4, vol. 10, pp. 1455-1460, Nov. 1992.

Duenas, et al., "Selection of Phage Displayed Antibodies Based on Kinetic Constants", vol. 33, No. 3, pp. 279-285 (1996).

Duenas, et al., "In vitro Immunization of Naive Human B cells Yields High Affinity Immunoglobulin G Antibodies as Illustrated by Phage Display", pp. 1-7, Blackwell Science Ltd., (1996).

Foote, et al., "Kinetic Maturation of an Immune Response", Nature, vol. 352, (Aug. 8, 1991).

David G. Myszka, "Survey of the 1998 Optical Biosensor Literature", Journal of Molecular Recognition, (1999).

Knappik, et al., "Fully Synthetic Human Combinatorial Antibody Libraries (HuCAL) Based on Modular Consensus Frameworks and CDRs Randomized with Trinucleotides", Academic Press, pp. 57-86, (2000).

Myszka, et al., "Kinetic Analysis of a Protein Antigen-Antibody Interaction Limited by Mass Transport on an Optical Biosensor", Elsevier Science, pp. 127-137 (1997).

Johnson, et al., "Development of a Humanized Monoclonal Antibody (MEDI-493) with Potent In Vitro and In Vivo Activity against Respiratory Syncytial Virus," The Journal of Infectious Diseases, vol. 176, No. 5 (Nov. 1997).

Johnson, et al., "A Direct Comparison of the Activities of Two Humanized Respiratory Syncytal Virus Monoclonal Antibodies: MEDI-493 and RSHZ19," The Journal of Infectious Diseases, Vo. 180, No. 1 (Jul. 1999).

Wu, et al., "Stepwise In vitro Affinity Maturation of Vitaxin, an $\alpha_v\beta_a$-specific Humanized mAb," The National Academy of Sciences, vol. 95, pp. 6037-6042 (May 1998).

Prince, et al., "Treatment of Parainfluenza Virus Type 3 Bronchiolitis and Pneumonia in a Cotton Rat Model Using Topical Antibody and Glucocorticosteroid," The Journal of Infectious Diseases, pp. 598-608 (1996).

Glaser, et al., "Antibody Engineering by Codon-Based Mutagenesis in a Filamentous Phage Vector System," The Journal of Immunology, vol. 149, pp. 3903-3913 (Dec. 1992).

Rosok, et al., "A Combinatorial Library Strategy for the Rapid Humanization of Anticarcinoma BR 96 Fab," The Journal of Biological Chemistry, vol. 271, No. 27 pp. 22611-22618 (Sep. 1995).

Karlsson, et al., "Experimental Design for Kinetic Analysis of Protein—Protein Interactions with Surface Plasmon Resonance Biosensors," The Journal of Immunological Methods, (1997).

Foote, et al., "Kinetic and Affinity Limits on Antibodies Produced During Immune Response," Proc. Nat'l. Acad. Science USA, vol. 92, pp. 1254-1256 (Feb. 1995).

Roost, et al., "Early High-Affinity Neutralizing Anti-Viral IgG Responses Without Further Overall Improvements of Affinity," Proc. Nat'l. Acad. Sci. USA, vol. 92, pp. 1257-1261 (Feb. 1995).

Everitt, et al., "The Pharmacokinetics, Antigenicity, and Fusion-Inhibition Activity of RSHZ19, a Humanized Monoclonal Antibody to Respiratory Syncytial Virus, in Healthy Volunteers," The Journal of Infectious Diseases, (1996).

Prince, et al., "Quantitative Aspects of Passive Immunity to Respiratory Syncytkal Virus Infection in Infant Cotton Rats," Journal of Virology, pp. 517-520, vol. 55, No. 3 (1985).

Raman, et al., "Diffusion-Limited Rates for Monoclonal Antibody Binding to Cytochrome," Biochemistry (1992).

Chmura et al., PNAS (Jul. 17, 2001), vol. 98, No. 15, pp. 8480-8484.

Chamat et al., "Human monoclonal antibodies isolated from spontaneous Epstein-Barr Virus—transformed tumors of Hu-SPL-SCID mice and specific for fusion protein display broad neutralizing activity toward respiratory syncytial virus," *Journal of Infections Diseases* 180:268-277 (1999).

Heard et al., "Two neutralizing human anti-RSV antibodies: cloning, expression, and characterization," *Molecular Medicine* 5(1):35-45 (1999)

U.S. Appl. No. 60/168,426, filed Jan. 27, 2000, Young et al.
U.S. Appl. No. 60/186,252, filed Mar. 1, 2000, Young et al.
U.S. Appl. No. 09/724,396, filed Nov. 28, 2000, Young et al.
U.S. Appl. No. 09/724,531, filed Nov. 28, 2000, Young et al.
U.S. Appl. No. 10/403,180, filed Mar. 31, 2003, Young et al.

Abman et al., 1988, "Role of Respiratory Syncytial Virus in Early Hospitalizations for Respiratory Distress of Young Infants With Cystic Fibrosis", J Pediatr. 113(5):826-380.

American Academy of Pediatrics Committee on Infectious Diseases: Use of Ribavirin in the Treatment of Respiratory Syncytial Virus Infection. Pediatrics. Sep. 1993;92(3):501-504.

Anderson et al., 1985, "Microneutralization test for respiratory syncytial virus based on an enzyme immunoassay," J. Clin. Microbiol. 22:1050-1052.

Beeler et al., 1989, "Neutralization Epitopes of the F Glycoprotein of Respiratory Syncytial Virus: Effect of Mutation Upon Fusion Function", J Virol. 63(7):2941-2950.

Bentley and Rabbitts, 1980, "Human immunoglobulin variable region genes—DNA Sequences of Two V Kappa Genes and a Pseudogene", Nature 288: 730-733.

Boulianne et al., 1984, "Production of functional chimaeric mouse/human antibody," Nature 312(5995):643-646.

Carson and Freimark, 1986, "Human lymphocyte hybridomas and monoclonal antibodies," Adv. Immunol. 38:275-311.

Chanock et al., "Respiratory syncytial virus," *Viral Infections of Humans, Epidemiology and Control*, 3rd Evans, ed., A.S. Chapter 20:525-544 (1989).

Cleek et al., 1997, "Biodegradable Polymeric Carriers for a bFGF Antibody for Cardiovascular Application" Pro. Int'l Symp. Control. Rel Bioact. Mater. 24: 853-854.

Conrad et al., 1987, "Aerosolized ribavirin treatment of respiratory syncytial virus infection in infants hospitalized during an epidemic," Pediatr. Infect. Dis. J. 6(2):152-158.

Cruse and Lewis, 1995, Illustrated Dictionary of Immunology, Boca Raton: CRC Press, pp. 18-19.

Dorland's Illustrated Medical Dictionary, 1994, 28th ed., Philadelphia: WB Saunders p. 874.

Falsey, 1991, "Noninfluenza Respiratory Virus Infection in Long-Term Care Facilities", Infect Control Hosp Epidemiol. 12(10):602-608.

Garvie and Gray, 1980, "Outbreak of Respiratory Syncytial Virus Infection in the Elderly", Br. Med. J. 281(6250):1253-1254.

Geneseq Database, Accession No: AA W70933, entry date Oct. 1998 from patent No. FR2758331-A1 of Bourgeois et al.

Glezen et al., 1981, "Risk of Respiratory Syncytial Virus Infection for Infants From Low-Income Families in Relationship to Age, Sex, Ethnic Group, and Maternal Antibody Level", J. Pediatr. 98(5):708-715.

Greenspan et al., 1999, Nature Biotechnology 17:936-937.

Groothuis et al., 1988, "Respiratory Syncytial Virus Infection in Children with Bronchopulmonary Dysplasia", Pediatrics. 82(2):199-203.

Groothuis et al., 1993, "Prophylactic Administration of Respiratory Syncytial Virus Immune Globulin to High-risk Infants and Young Children", The Respiratory Syncytial Virus Immune Globulin Study Group. N Engl J Med. 329(21):1524-1530.

Groves et al., 1987, "Production of an ovine monoclonal antibody to testosterone by an interspecies fusion," Hybridoma 6(1):71-76.

Hacking and Hull, "Respiratory syncytial virus—viral biology and the host response," *J Infect.* 45(1):18-24 (2002).

Hall et al., 1975, "Nosocomial respiratory syncytial virus infections," N. Engl. J. Med. 293(26):1343-1346.

Hall et al., 1979, "Neonatal Respiratory Syncytial Virus Infection", N Engl J Med. 300(8):393-396.

Hall et al., 1983, "Aerosolized ribavirin treatment of infants with respiratory syncytial viral infection. A randomized double-blind study," N. Engl. J. Med. 308(24):1443-1447.

Hall et al., 1985, "Ribavirin treatment of respiratory syncytial viral infection in infants with underlying cardiopulmonary disease," JAMA 254(21):3047-3051.

Hall, "Respiratory syncytial virus," *Textbook of Pediatric Infectious Dieseases*, Feigin and Cherry, eds., WB Saunders, Philadelphia, pp. 1653-1676 (1987).

Hall, C.B., 1993, Respriratory Syncytial : What We Know Now, Contemp. Pediatrics, 10: 92-110.

Haynes et al., 2002, "Neutralizing anti-F glycoprotein and anti-substance P antibody treatment effectively reduces infection and inflammation associated with respiratory syncytial virus infection," J. Virol. 76(14):6873-6881.

Heard et al., "Two Neutralizing Human Anti RSV Antibodies: Cloning, Expression and Characterization," *Molec. Med.* 5:35-45 (1999).

Hemming et al., "Immunoglobulins in respiratory syncytial virus infections," *Clinical Use of Intravenous Immunoglobulins*, Morell and Nydegger., eds., Academic Press, London, pp. 285-294 (1986).

Hemming et al., 1985, "Studies of Passive Immunotherapy for Infections of Respiratory Syncytial Virus in the Respiratory Tract of a Primate Model", J Infect Dis. 152(5):1083-1087.

Henderson et al., 1979, "Respiratory-Syncytial-Virus Infections, Reinfections and Immunity. A Prospective, Longitudinal Study in Young Children", N Engl J Med. 300(10):530-534.

Hertz et al., 1989, "Respiratory Syncytial Virus-Induced Acute Lung Injury in Adult Patients With Bone Marrow Transplants: a Clinical Approach and Review of the Literature", Medicine (Baltimore). 68(5):269-281.

Howard et al., 1989, "Intracerebral Drug Delivery in Rats with Lesion-Induced Memory Deficits", J Neurosurg. 71(1):105-112.

Johnson et al., 1987, "Development of a Humanized Monoclonal Antibody (MEDI-493) With Potent In Vitro and In Vivo Activity Against Respiratory Syncytial Virus", J Infect Dis. 176(5):1215-1224.

Johnson et al., 1987, "The G Glycoprotein of Human Respiratory Syncytial Viruses of Subgroups A and B: Extensive Sequence Divergence Between Antigenically Related Proteins", Proc Natl Acad Sci U S A. 84(16):5625-5629.

Kapikian et al., 1969, "An Epidemiologic Study of Altered Clinical Reactivity to Respiratory Syncytial (RS) Virus Infection in Children Previously Vaccinated With an Inactivated RS Virus Vaccine", Am J Epidemiol. 89(4):405-421.

Kim et al., 1969, "Respiratory Syncytial Virus Disease in Infants Despite Prior Administration of Antigenic Inactivated Vaccine", Am J Epidemiol. 89(4):422-434.

Lam et al., 1997, "Microencapsulation of Recombinant Humanized Monoclonal Antibody for Local Delivery", Proc. Int'l. Symp. Control Rel. Bioact. Mater. 24:759-760.

Lamprecht et al., 1976, "Role of Maternal Antibody in Pneumonia and Bronchiolitis Due to Respiratory Syncytial Virus", J Infect Dis. 134(3):211-217.

Landry et al., "Evaluation of Reconstituted Lyophilized Palivizumab (Synagis™) Given Intravenously at 15 and 30 mg/kg," Annual Meeting of the American Pediatric Society and the Society for Pediatric Research, Meeting Poster/Abstract 969, *Pediatric Research* 45 (4 PART 2):166A (1999).

Levy et al., 1985, "Inhibition of Calcification of Bbioprosthetic Heart Valves by Local Controlled-release Diphosphonate", Science. 228(4696):190-192.

Liu et al., 1987, "Expression of mouse::human immunoglobulin heavy-chain cDNA in lymphoid cells," Gene 54(1):33-40.

LoBuglio et al., 1989, "Mouse/human chimeric monoclonal antibody in man: kinetics and immune response," Proc. Natl. Acad. Sci. USA 86(11):4220-4224.

MacDonald et al., 1982, "Respiratory Syncytial Viral Infection in Infants With Congenital Heart Disease", N Engl J Med. 307(7):397-400.

MedImmune, Inc., 1999, "SYNAGIS™ package insert", last revised Dec. 2, 1999.

MedImmune, SYNAGIS (registered trademark) package insert, revised Oct. 23, 2002.

Morrison et al., 1984, "Chimeric human antibody molecules: mouse antigen-binding domains with human constant region domains," Proc. Natl. Acad. Sci. USA 81(21):6851-6855.

Morrison et al., 1985, "Transfectomas provide novel chimeric antibodies," Science 229(4719):1202-1207.

Murphy et al., 1988, "Passive Transfer of Respiratory Syncytial Virus (RSV) Antiserum Suppresses The Immune Response to the RSV Fusion (F) and Large (G) Glycoproteins Expressed By Recombinant Vaccinia Viruses", J Viral. 62(10):3907-3910.

Murphy et al., 1991, "Effect of Passive Antibody on the Immune Response of Cotton Rats to Purified F and G HG Glycoproteins of Respiratory Syncytial Virus (RSV)", Vaccine. 9(3):185-189.

Murphy et al., 1994, "An Update on Approaches to the Development of Respiratory Syncytial Virus (RSV) and Parainfluenza Virus Type 3 (PIV3) Vaccines", Virus Res. 32(1):13-36.

Navas et al., 1992 , "Improved Outcome of Respiratory Syncytial Virus Infection in a High-Risk Hospitalized Population of Canadian children. Pediatric Investigators Collaborative Network on Infections in Canada", J Pediatr. 121(3):348-354.

Ning et al., 1996, "Intratumoral Radioimmunotherapy of a Human Colon Cancer Xenograft Using a Sustained Release Gel", Radiotherapy and Oncology 39: 179-189.

Ogra et al., 1988, "Respiratory Syncytial Virus Infection and the Immunocompromised Host", Pediatr Infect Dis J. Apr. 1988;7(4):246-249.

Orkin and Motulsky, "Report and recommendations of the panel to assess the NIH investment in research on gene therapy," available from http://www.nih.gov/news/panelrep.html (1995).

Palivizumab et al., 1998, "A Humanized Respiratory Syncytial Virus Monoclonal Antibody, Reduces Hospitalization From Respiratory Syncytial Virus Infection in High-Risk Infants", The IMpact-RSV Study Group. Pediatrics. 102(3 Pt 1):531-537.

Pohl et al., 1992, "Respiratory Syncytial Virus Infections in Pediatric Liver Transplant Recipients", J Infect Dis. 165(1):166-169.

Press and Hogg, 1970, "The Amino Acid Sequences of the Fd Fragments of Two Human Gamma-I Heavy chains", Biochem J. 117(4):641-660.

Prince et al., "Quantitative aspects of passive immunity to respiratory syncytial virus infection in infant cotton rats," Journal of Virology 55(3):517-520 (1985).

Prince et al., 1983, "Mechanisms of Immunity to Respiratory Syncytial Virus in Cotton Rats", Infect Immun. 42(1):81-87.

Prince et al., 1985, "Immunoprophylaxis and Immunotherapy of Respiratory Syncytial Virus Infection in the Cotton rat", Virus Res. 3(3):193-206.

Prince et al., 1990, "Mechanism of Antibody-mediated Viral Clearance in Immunotherapy of Respiratory Syncytial Virus Infection of Cotton Rats", J Virol. 64(6):3091-3092.

Rudikoff et al., 1982, "Single amino acid substitution altering antigen-binding specificity," Proc. Natl. Acad. Sci. USA 79(6):1979-1983.

Ruuskanen and Ogra, 1993, "Respiratory syncytial virus", Curr Probl Pediatr. 23(2):50-79.

Saez Llorens et al., "Safety and pharmacokinetics of an intramuscular humanized monoclonal antibody to respiratory synctial virus in premature infants and infants with bronchopulmonary dysplasia," *Pediatr. Infect Dis J* 17(9):787-791 (1998).

Saez-Llorens et al., "Phase I/II open label multi dose escalation trial of a humanized respiratory synctial virus (RSV) monoclonal antibody (Medi-493) administered intramuscularly (IM) in high risk children," Abstract in Non HIV virology, ICAAC Toronto. 37:229 (1997).

Sahagan et al., 1986, "A genetically engineered murine/human chimeric antibody retains specificity for human tumor-associated antigen," J. Immunol. 137(3):1066-1074.

Saudek et al., 1989, A Preliminary Trial of the Programmable Implantable Medication System for Insulin Delivery. N Engl J Med. 321(9):574-579.

Sefton, 1987, "Implantable Pumps", CRC Crit. Ref. Biomed. Eng. 14:20.

Smith et al., 1991, "A Controlled Trial of Aerosolized Ribavirin in Infants Receiving Mechanical Ventilation for Severe Respiratory Syncytial Virus Infection", N Engl J Med. 325(1):24-29.

Song et al., 1995, "Antibody Mediated Lung Targeting of Long-Circulating Emulsions", PDA Journal of Pharmaceutical Science & Technology 50: 372-377.

Sorbera et al., "Palivizumab," *Drugs of the Future* 23(9):970-976 (1998).

Sorbera et al., "Palivizumab," *Drug Data Report* 20:702-703 (1998).

Steplewski et al., 1988, "Biological activity of human-mouse IgG1, IgG2, IgG3, and IgG4 chimeric monoclonal antibodies with antitumor specificity," Proc. Natl. Acad. Sci. USA 85(13):4852-4856.

Subramanian et al., "Randomized double blind placebo controlled dose escalation trial of a humanized respiratory synctial virus monoclonal antibody in high risk infants," Poster session, *Infectious Diseases* 130A:768. (1997).

Subramanian et al., "Safety, tolerance and pharmacokinetics of a humanized monoclonal antibody to respiratory syncytial virus in premature infants and infants with bronchopulmonary dysplasia," *Pediatric Infectious Disease Journal* 17(2):110-115 (1997).

Sun et al., 1987, "Chimeric antibody with human constant regions and mouse variable regions directed against carcinoma-associated antigen 17-1A," Proc. Natl. Acad. Sci. USA 84(1):214-218.

Takeda et al., 1985, "Construction of chimaeric processed immunoglobulin genes containing mouse variable and human constant region sequences," Nature 314(6010):452-454.

U.S. Census Bureau, Age Data, website updated May 12, 2004, http://www.census.gov/population/www/socdemo/age.html.

U.S. Department of Commerce, Economics and Statistics Administration, Bureau of the Census, We the American Elderly, Sep. 1993.

van Wyke Coelingh et al., 1985, "Antigenic variation in the hemagglutinin-neuraminidase protein of human parainfluenza type 3 virus," Virology 143(2):569-582.

Verma et al., "Gene therapy promises, problems and prospects," *Nature* 389:239-242 (1997).

Wald et al., 1988, "In re ribavirin: a case of premature adjudication?" J. Pediatr. 112(1):154-158.

Walsh et al., 1987, "Immunization with Glycoprotein Subunits of Respiratory Syncytial Virus to Protect Cotton Rats Against Viral Infection", J Infect Dis. 155(6):1198-1204.

Wright et al., 1982, "Administration of a highly attenuated, live respiratory syncytial virus vaccine to adults and children," Infect. Immun. 37(1):397-400.

Barbas et al., "Selection and evolution of high-affinity human antiviral antibodies," *Trends in Biotechnology* 14(7):230-234 (1996).

Roguska et al, "Humanization of murine monoclonal antibodies through variable domain resurfacing," *Proceedings of the National Academy of Sciences of the United States of America* 91(3):969-973 (1994).

U.S. Appl. No. 11/230,593, filed Sep. 21, 2005, Tous et al.

Arbiza et al., "Characterization of two antigenic sites recognized by neutralizing monoclonal antibodies directed against the fusion glycoprotein of human respiratory syncytial virus," *J. Gen. Virol.* 73: 2225-2234 (1992).

Balint and Larrick, "Antibody engineering by parsimonious mutagenesis." *Gene* 137(1):109-118 (1993).

Bourgeois et al., "New peptides recognizing viral epitope with tropism to mucosa—useful for, e.g. diagnosing, preventing and treating viral infection(s)." GENESEQ database entry for Accession No. AAW70933; Oct. 14, 1998 and alignment with Seq ID No. 12 of U.S. Appl. No. 09/771,415.

Egan et al., "Effect of Sch 55700, a humanized monoclonal antibody to human interleukin-5, on eosinophilic responses and bronchial hyperreactivity." Arzneimittel-forschung. 49(9):779-790 (1999).

Garcia-Barreno, B. et al., "Marked Differences in the Antigenic Structure of Human Respiratory Syncytial Virus F and G Glycoproteins," *J. Virology.* 925-932 (1989).

Love et al., "How the anti-(metal chelate) antibody CHA255 is specific for the metal ion of its antigen: X-ray structures for two Fab'/hapten complexes with different metals in the chelate." *Biochemistry* 32(41):10950-10959 (1993).

Nguyen et al, "Efficient generation of respiratory syncytial virus (RSV)-neutralizing human MoAbs via human peripheral blood lymphocyte (hu-PBL)-SCID mice and scFv phage display libraries," *Clin. Exp. Immunol.* 122:85-93 (2000).

Palomo, C. et al., "Induction of a Neutralizing Immune Response to Human Respiratory Syncytial Virus with Anti-Idiotypic Antibodies" *J. Virology* 64(9): 4199-4206 (1990).
Whitlow et al., "1.85 A structure of anti-fluorescein 4-4-20 Fab." *Protein Eng.* 8(8):749-761 (1995).
Wu et al., "Ultra-potent Antibodies Against Respiratory Syncytial Virus: Effects of Binding Kinetics and binding Valence on Viral Neutralization," *J. Mol. Biol.* 350: 126-144 (2005).
Wu and An, "Tailoring Kinetics of Antibodies Using Focused Combinatorial Libraries" chapter 13 from *Methods in Molecular Biology* vol. 207, Eds. Welschop and Krauss, Humana Press Inc., Totowa, NJ, pp. 213-233 (2002).
Blake, et al., 1999, Automated kinetic exclusion assays to quantify protein binding interactions in homogeneous solution.Anal Biochem. 272(2):123-34.
Boder et al., 2000, "Directed evolution of antibody fragments with monovalent femtomolar antigen-binding affinity," Proc. Natl. Acad. Sci. U. S. A. 97(20):10701-5.
Boeckh et al., 2001, "Phase 1 Evaluation of the Respiratory Syncytial Virus-Specific Monoclonal Antibody Palivizumab in Recipients of Hematopoietic Stem Cell Transplants." J. of Infect. Dis. 184:350-354.
Chowdhury et al., 2005, "Tailor-made antibody therapeutics." Methods 36: 11-24.
Crowe et al., 1998, "Monoclonal antibody-resistant mutants selected with a respiratory syncytial virus-neutralizing human antibody fab fragment (Fab 19) define a unique epitope on the fusion (F) glycoprotein," Virology.252(2):373-5.
Dall'Acqua, 2002, "Increasing the Affinity of a Human IgG1 for the Neonatal Fc Receptor: Biological Consequences." J. of Immunol. 169: 5171-5180.
Dall'Acqua Declaration (dated Jun. 16, 2008)—Filed in U.S. Appl. No. 10/657,363 (U.S. Publ. No. 2004/0098189) on Jun. 16, 2008.
Delagrave et al., 1999, "Effects of humanization by variable domain resurfacing on the antiviral activity of a single-chain antibody against respiratory syncytial virus". Protein Eng. 12(4):357-62.
Evans et al., eds., 1989, Viral Infections of Humans: Epidemiology and Control, 3rd ed., Plenum Medical Book, New York, pp. 525-544.
Feigen et al., 1987, Textbook of Pediatric Infectious Diseases, WB Saunders, Philadelphia, pp. 1653-1675.
Fields et al., 1996, "Crystal Structure of the V-alpha domain of a T cell antigen receptor," Immunotechnology 2(4):270.
Gilchrist, et al. 1994 "National surveillance for respiratory syncytial virus, United States, 1985-1990," J. Infect. Dis. 170:986-990.
Hall et al., eds., 1995, Principles and Practice of Infectious Diseases 4th ed., Churchill Livingstone, New York, pp. 1501-1519.
Kunkel et al., 1987, "Rapid and efficient site-specific mutagenesis without phenotypic selection," Methods Enzymol. 154:367-382.
Landry et al., 1999, "Evaluation of reconstituted lyophilized palivizumab given intravenously at 15 and 30 mg/kg," Pediatric Research, 45 (4) Pt 2:166A, 969 Annual Meeting of the American Pediatric Society and the Society for Pediatric Research. San Francisco, California, USA. May 1-4, 1999 Poster Session (poster 87).
Malley et al., 1998, "Reduction of Respiratory Syncytial Virus (RSV) in Tracheal Aspirates in Intubated Infants by Use of Humanized Monoclonal Antibody to RSV F Protein." J. of Infect. Dis. 178:1555-1561.
Marks et al., 1992, "By-passing immunization: building high affinity human antibodies by chain shuffling," Biotechnology (N Y) 10(7):779-83.
McArthur-Vaughan et al., 2002, "A rhesus monkey model of respiratory syncytial virus infection," J. Med. Primatol. 31(2):61-73.

Medimmune, Inc. (MEDI) Release: Numax achieves primary endpoint in preliminary analysis of data from comparative phase 3 trial with Synagis (Nov. 6, 2006) BioSpace Beat, biospace.com (www.biospace.com/news_story.aspx?StoryID=36114&full=1).

Medimmune, Inc.'s (MEDI) phase I Numax study shows potential to reduce RSV disease in upper airway of children. (Sep. 1, 2005) BioSpace Beat, Biospace.com (www.biospace.com/news_story.aspx?StoryID=21014020).

Meissner et al., "Safety and Pharmacokinetics of an Intramuscular Monoclonal Antibody (SB 209763) Against Respiratory Syncytial Virus (RSV) in Infants and Young Children at Risk for Severe RSV Disease", *Antimicrob Agents Chemother* 43:1183-1188 (1999).

Motavizumab vs. palivizumab for Rsv infections in infants (Nov. 11, 2006) Inpharma vol. 1 No. 1563, p. 5.

Physician's Desk Reference, 2001, $55^{th}$ ed. p. 1863-1864.

Prince et al., 2000, "Treatment of Respiratory Syncytial Virus Bronchiolitis and Pneumonia in a Cotton Rat Model with Systematically Administered Monoclonal Antibody (Palivizumab) and Glucocorticosteroid," J Inf Diseases 182:1326-1330.

Prince, 2001, "An update on respiratory syncytial virus antiviral agents." Expert Opin Investig Drugs. 10(2):297-308.

Prince, 1975, "The Pathogenesis of Respiratory Syncytial Virus Infection in Infant Ferrets" Ph.D. Dissertation, University of California-Los Angeles.

Subramanian et al., 1998, "Safety, Tolerance and Pharmacokinetics of a Humanized Monoclonal Antibody to Respiratory Syncytial Virus in Premature Infants and Infants with Bronchopulmonary Dysplasia", Pediatric Infect Dis J. 17:110-115.

Van Der Merwe et al., 1993, "Affinity and kinetic analysis of the interaction of the cell adhesion molecules rat CD2 and CD48," Embo J. 12(13):4945-4954.

Van Der Merwe et al., 1994, "Human cell-adhesion molecule CD2 binds CD58 (LFA-3) with a very low affinity and an extremely fast dissociation rate but does not bind CD48 or CD59," Biochemistry 33(33):10149-10160.

Watkins et al., 1997, Determination of the relative affinities of antibody fragments expressed in *Escherichia coli* by enzyme-linked immunosorbent assay. Anal Biochem. 253(1):37-45.

Weltzin et al., 1994, "Intranasal Monoclonal Immunoglobulin A against Respiratory Syncytial Virus Protects against Upper and Lower Respiratory Tract Infections in Mice." Anitmicro Agents & Chemo. 38(12):2785-2791.

Weltzin et al., 1996, "Intranasal Monoclonal IgA Antibody to Respiratory Syncytial Virus Protects Rhesus Monkeys against Upper and Lower Tract Infection." J. of Infect Dis. 174:256-241.

Wu et al, 2002, "Tailoring Kinetics of Antibodies Using Focused Combinatorial Libraries" chapter 13 from *Methods in Molecular Biology* vol. 207, Eds. Welschop and Krauss, Humana Press Inc., Totowa, NJ, pp. 213-233.

U.S. Appl. No. 09/724,396—Office Action dated Mar. 26, 2002.
U.S. Appl. No. 09/724,396—Office Action dated Dec. 3, 2002.
U.S. Appl. No. 09/724,396—Office Action dated Jun. 3, 2003.
U.S. Appl. No. 09/724,396—Office Action dated Jul. 28, 2003.
U.S. Appl. No. 09/724,396—Office Action dated Apr. 5, 2004.
U.S. Appl. No. 09/724,531 (U.S. Patent No. 7,229,619)—Office Action dated Feb. 21, 2003.
U.S. Appl. No. 09/724,531 (U.S. Patent No. 7,229,619)—Office Action dated Oct. 21, 2003.
U.S. Appl. No. 09/724,531 (U.S. Patent No. 7,229,619)—Office Action dated Jun. 4, 2004.
U.S. Appl. No. 09/724,531 (U.S. Patent No. 7,229,619)—Office Action dated Feb. 9, 2005.
U.S. Appl. No. 09/724,531 (U.S. Patent No. 7,229,619)—Office Action dated Jun. 15, 2005.
U.S. Appl. No. 09/724,531 (U.S. Patent No. 7,229,619)—Office Action dated Apr. 4, 2006.
U.S. Appl. No. 09/724,531 (U.S. Patent No. 7,229,619)—Office Action dated Aug. 22, 2006.
U.S. Appl. No. 09/724,531 (U.S. Patent No. 7,229,619)—Office Action dated Jan. 30, 2007.
U.S. Appl. No. 09/996,288 (U.S. Patent No. 6,818,216)—Office Action dated Jul. 14, 2003.
U.S. Appl. No. 09/996,288 (U.S. Patent No. 6,818,216)—Office Action dated Jan. 29, 2004.
U.S. Appl. No. 09/996,288 (U.S. Patent No. 6,818,216)—Office Action dated Jun. 30, 2004.
U.S. Appl. No. 09/996,265 (U.S. Patent No. 6,855,493)—Office Action dated Aug. 12, 2003.
U.S. Appl. No. 09/996,265 (U.S. Patent No. 6,855,493)—Office Action dated Mar. 31, 2004.
U.S. Appl. No. 09/996,265 (U.S. Patent No. 6,855,493)—Office Action dated Jul. 13, 2004.
U.S. Appl. No. 10/403,180 (U.S. Patent No. 7,179,900)—Office Action dated Apr. 4, 2005.
U.S. Appl. No. 10/403,180 (U.S. Patent No. 7,179,900)—Office Action dated Oct. 19, 2005.
U.S. Appl. No. 10/403,180 (U.S. Patent No. 7,179,900)—Office Action dated Mar. 30, 2006.
U.S. Appl. No. 10/403,180 (U.S. Patent No. 7,179,900)—Office Action dated Sep. 6, 2006.
U.S. Appl. No. 10/657,363 (U.S. Publ. No. 2004/0098189)—Office Action dated May 30, 2007.
U.S. Appl. No. 10/657,363 (U.S. Publ. No. 2004/0098189)—Office Action dated Dec. 14, 2007.
U.S. Appl. No. 10/900,230 (U.S. Publ. No. 2005/0002926)—Office Action dated Jan. 24, 2006.
U.S. Appl. No. 10/900,230 (U.S. Publ. No. 2005/0002926)—Office Action dated Jun. 30, 2006.
U.S. Appl. No. 10/900,230 (U.S. Publ. No. 2005/0002926)—Office Action dated Dec. 26, 2006.
U.S. Appl. No. 10/900,230 (U.S. Publ. No. 2005/0002926)—Office Action dated Jun. 27, 2007.
U.S. Appl. No. 10/900,230 (U.S. Publ. No. 2005/0002926)—Office Action dated Feb. 21, 2008.
U.S. Appl. No. 10/962,285 (U.S. Patent No. 7,323,172)—Office Action dated Oct. 26, 2006.
U.S. Appl. No. 10/962,285 (U.S. Patent No. 7,323,172)—Office Action dated Apr. 13, 2007.
U.S. Appl. No. 11/263,230 (U.S. Publ. No. 2006/0115485)—Office Action dated Jan. 9, 2008.
U.S. Appl. No. 11/643,982 (U.S. Publ. No. 2007/0196916)—Office Action dated Sep. 2, 2008.
U.S. Appl. No. 09/771,415 (U.S. Patent No. 6,656,467)—Office Action dated Jun. 18, 2002.
U.S. Appl. No. 09/771,415 (U.S. Patent No. 6,656,467)—Office Action dated Feb. 10, 2003.
U.S. Appl. No. 09/771,415 (U.S. Patent No. 6,656,467)—Office Action dated May 6, 2003.
U.S. Appl. No. 10/900,230 (U.S. Publ. No. 2005/0002926)—Office Action dated Sep. 18, 2008.
U.S. Appl. No. 10/962,285 (U.S. Patent No. 7,323,172)—Office Action / Notice of Allowability dated Sep. 6, 2007.
U.S. Appl. No. 11/263,230 (U.S. Publ. No. 2006/0115485)—Office Action dated Oct. 2, 2008.
U.S. Appl. No. 10/020,354 (U.S. Patent No. 7,083,784)—Office Action dated Apr. 7, 2004.
U.S. Appl. No. 10/020,354 (U.S. Patent No. 7,083,784)—Office Action dated Nov. 17, 2004.
U.S. Appl. No. 10/020,354 (U.S. Patent No. 7,083,784)—Office Action dated Jun. 1, 2005.
U.S. Appl. No. 10/020,354 (U.S. Patent No. 7,083,784)—Office Action / Notice of Allowability dated Dec. 15, 2005.
Dall'Acqua Declaration (dated Oct. 3, 2005)—Filed in U.S. Appl. No. 10/020,354 (U.S. Patent No. 7,083,784) on Oct. 8, 2005.
U.S. Appl. No. 11/397,328 (U.S. Publ. No. 2006/0198840)—Office Action dated Oct. 18, 2007.
U.S. Appl. No. 11/397,328 (U.S. Publ. No. 2006/0198840)—Office Action / Notice of Allowability dated Aug. 7, 2008.
U.S. Appl. No. 10/461,904 (U.S. Patent No. 7,132,100)—Office Action dated Dec. 14, 2004.
U.S. Appl. No. 10/461,904 (U.S. Patent No. 7,132,100)—Office Action dated Nov. 25, 2005.
U.S. Appl. No. 10/461,904 (U.S. Patent No. 7,132,100)—Office Action / Notice of Allowability dated May 2, 2006.

U.S. Appl. No. 11/362,267 (U.S. Patent No. 7,294,336)—Office Action dated May 4, 2007.
U.S. Appl. No. 11/362,267 (U.S. Patent No. 7,294,336)—Office Action / Notice of Allowability dated Aug. 6, 2007.
U.S. Appl. No. 10/461,863 (U.S. Patent No. 7,425,618)—Office Action dated Dec. 18, 2006.
U.S. Appl. No. 10/461,863 (U.S. Patent No. 7,425,618)—Office Action dated Jun. 11, 2007.
U.S. Appl. No. 10/461,863 (U.S. Patent No. 7,425,618)—Office Action / Notice of Allowability dated Nov. 19, 2007.
U.S. Appl. No. 12/075,197, filed Mar. 10, 2008, Oliver et al.
U.S. Appl. No. 12/476,183, filed Jun. 1, 2009, Young et al.
Abbas et al., 1991. Cellular and Molecular Immunology- Chapter 3- Antibodies and Antigens, p. 45-47; W.B Saunders Company.
Adams et al., 1998. Prolonged in vivo tumour retention of a human diabody targeting the extracellular domain of human HER2/neu. Br J Cancer. 77(9):1405-12.
Ames et al., 1995. Conversion of murine Fabs isolated from a combinatorial phage display library to full length immunoglobulins. J. Immunol Methods.184(2):177-86.
Bennett et al., 2007. Immunopathogenesis of Respiratory Syncytial Virus Bronchiolitis. J Infect Dis. 195(10):1532-1540.
Berzofsky and Berkower, 1993. in Paul, W.E., Fundamental Immunology (Raven Press), Chapter 8: Immunogenicity and antigen structure, p. 242.
Berzofsky and Berkower, 1993. in Paul, W.E., Fundamental Immunology (Raven Press), Chapter 9: Structure and Function of Immunoglobulins, p. 292-295.
Better et al., 1988. *Escherichia coli* secretion of an active chimeric antibody fragment. Science. 240(4855):1041-3.
Blake et al., 1999. Automated Kinetic Exclusion Assays to Quantify Protein Binding Interactions in Homogeneous Solution. Analytical Biochemistry 272: 123-134.
Brinkmann et al., 1995. Phage display of disulfide-stabilized Fv fragments. J Immunol Methods. 182(1):41-50.
Burton and Barbas, 1994. Human antibodies from combinatorial libraries. Adv. Immunol. 57:191-280.
Cao et al., 2003. Bispecific antibody conjugates in therapeutics; Adv Drug Deliv Rev. 55(2):171-97.
Carlsson et al., 1992. Human peripheral blood lymphocytes transplanted into SCID mice constitute an in vivo culture system exhibiting several parameters found in a normal humoral immune response and are a source of immunocytes for the production of human monoclonal antibodies. J Immunol. 1992; 148(4):1065-71.
Chothia et al., 1998. Structural determinants in the sequences of immunoglobulin variable domain. J Mol Biol. 278(2):457-79.
Connors, 1990. Chemical Kinetics: The Study of Reaction Rates in Solution, p. 152.
Crowe et al., 1998. Monoclonal antibody-resistant mutants selected with a respiratory syncytial virus-neutralizing human antibody fab fragment (Fab 19) define a unique epitope on the fusion (F) glycoprotein. Virology. 252(2):373-5.
Crowe et al., 1993. Recombinant human respiratory syncytial virus (RSV) monoclonal antibody Fab is effective therapeutically when introduced directly into the lungs of RSV-infected mice. Proc Natl Acad Sci USA. 91:1386-1390.
Delagrave et al., 1999. Effects of humanization by variable domain resurfacing on the antiviral activity of a single-chain antibody against respiratory syncytial virus. Protein Eng. 12(4):357-62.
De Vincenzo et al., 2005. Factors Predicting Childhood Respiratory Syncytial Virus Severity—What They Indicate About Pathogenesis. Ped Inf Dis J. 24:S177-S183.
Downham et al., 1976. Breast-feeding protects against respiratory syncytial virus infections. Br Med J. 2(6030):274-6.
Fahy and O'Byrne, 2001. Reactive Airways Disease. Am J Respir Crit Care Med. 163(4):822-3.
Fields et al., 1990, Fields Virology, 2nd Ed., vol. 1, Raven Press, NY p. 1045-1072.
Fields et al., 1996. Crystal Structure of the V-alpha domain of a T cell antigen receptor. Immunotechnology 2(4):270.
Foecking and Hofstetter, 1986. Powerful and versatile enhancer-promoter unit for mammalian expression vectors. Gene. 45:101-105.

Gillies et al., 1989. High-level expression of chimeric antibodies using adapted cDNA variable region cassettes. J. Immunol Methods. 125:191-202.
Goldstein et al. 1993 "We The American Elderly", U.S. Dept. of Commerce, Economics and Statistics Admin., Bureau of the Census.
Hall et al., eds., 1995, Principles and Practice of Infectious Diseases 4th ed., Churchill Livingstone, New York, pp. 1501-1519.
Hammerling et al., 1981. Production of Antibody-Producing Hybridomas in the Rodent Systems, in Monoclonal antibodies and T-cell hybridomas, Elsevier, NY. p. 563-587.
Hellstrom et al., 1987. Antibodies for drug delivery. Controlled Drug Delivery, Fundamentals and Applications 2nd edition. Chapter 15: p. 623-653.
Hemming et al., 1988. Topically Administered Immunoglobulin Reduces PulmonaryRespiratory Syncytial Virus Shedding in Owl Monkeys. Antimicrob Agents Chemother. 32(8):1269-1270.
Hudson and Souriau, 2003. Engineered Antibodies. Nature Medicine 9(1):129-34.
Ifverson and Borrebaeck, 1996. SCID-hu-PBL: a model for making human antibodies? Semin Immunol. 8(4):243-8.
Johnson et al., 1991. Development of humanized monoclonal antibodies which neutralize respiratory syncytial virus. J. Cellular Biochem. Suppl. 15E. p. 120, Abstract No. 108.
Kettleborough et al., 1994. Isolation of tumor cell-specific single-chain Fv from immunized mice using phage-antibody libraries and the re-construction of whole antibodies from these antibody fragments. Eur J Immunol. 24(4):952-8.
Krishnan et al., 2008. Therapeutic addition of motavizumab, a monoclonal antibody against respiratory syncytial virus (RSV), modulates epithelial cell responses to RSV infection. Annual Interscience Conf Antimicrobial Agents Chemotherapy/Annual Meeting Infect Dis Soc Am. 48/46 Oct. 28 Abstract V-4147.
Kudo et al., 1993. Production of a human monoclonal antibody to a synthetic peptide by active in vivo immunization using a SCID mouse grafted with human lymphocytes; Tohoku J Exp Med. 171: 327-338.
Kunkel et al., 1987. Rapid and efficient site-specific mutagenesis without phenotypic selection. Methods Enzymol. 154:367-382.
Lagos et al., 2005. Administration of the anti-RSV monoclonal antibody (Mab) Numax™, is associated with a reduction in upper airway (UA) RSV load. World Congress Pediatr Infect Disease. Sep. 1-4.
Langer and Peppas, 1983. Chemical and physical structure of polymers as carriers for controlled release of bioactive agents: a review. J Macromol. Sci.- Rev. Macromol. Chem. Phys. C23(1):61-126.
Langer, 1990. New methods of drug delivery. Science. 249:1527-1533.
Lee et al., 1998. Demonstration of IgM antibodies of high affinity within the anti-Galalpha1-3Gal antibody repertoire. Transplantation; 66(8):1117-9.
Longberg and Huszar, 1995. Human antibodies form transgenic mice. Int. Rev. Immunol. 13:65-96.
McArthur-Vaughan et al., 2002. A rhesus monkey model of respiratory syncytial virus infection. J. Med. Primatol. 31(2):61-73.
McCall et al., 1999. Isolation and characterization of an anti-CD16 single-chain Fv fragment and construction of an anti-HER2/neu/anti-CD16 bispecific scFv that triggers CD16-dependent tumor cytolysis. Mol Immunol. 36(7):433-45.
Medimmune, Inc. Annual Report (2001).
Meissner et al., 1999. Safety and pharmacokinetics of an intramuscular monoclonal antibody (SB 209763) against respiratory syncytial virus (RSV) in infants and young children at risk for severe RSV disease. Antimicrob Agents Chemother. 43(5):1183-8.
Mejias et al., 2005. Respiratory synchytial virus infections: Old challenges and new opportunities. Ped. Infect. Dis. J. 24:S189-S197.
Mejias et al., 2005. Comparative Effects of Two Neutralizing Anti-Respiratory Syncytial Virus (RSV) Monoclonal Antibodies in the RSV Murine Model: Time versus Potency. Antimicrobial Agents and Chemotherapy. 49(11): 4700-4707.
Mullinax et al., 1992. Expression of a heterodimeric Fab antibody protein in one cloning step. Bio Techniques. 12:864-869.
O'Byrne and Postma, 1999. The Many Faces of Airway Inflammation. Am J Respir Crit Care Med. 159(5 Pt 2):S41-63.

Padlan, 1991. A possible procedure for reducing the immunogenicity of antibody variable domains while preserving their ligand-binding properties. Mol. Immunol. 28(4/5):489-498.

Persic et al., 1997. An integrated vector system for the eukaryotic expression of antibodies or their fragments after selection from phage display libraries. Gene. 187(1):9-18.

Physician's Desk Reference, 2001, 55th ed. p. 1863-1864.

Prince et al., 2000. Treatment of Respiratory Syncytial Virus Bronchiolitis and Pneumonia in a Cotton Rat Model with Systematically Administered Monoclonal Antibody (Palivizumab) and Glucocorticosteroid. J Inf Diseases. 182:1326-1330.

Prince, 1975. The Pathogenesis of Respiratory Syncytial Virus Infecton in Infant Ferrets. Ph.D. Dissertation, University of California-Los Angeles.

Prince, 2001. An update on respiratory syncytial virus antiviral agents. Expert Opin Investig Drugs. 10(2):297-308.

Prince et al., 1987. Effectiveness of Topically Administered Neutralizing Antibodies in Experimental Immunotherapy of Respiratory Syncytial Virus Infection in Cotton Rats. J Virol. 61(6):1851-1854.

Richter et al., 2008. Respiratory syncytial virus (RSV) therapy utilizing intranasally delivered motavizumab, a monoclonal antibody against F protein, Annual Interscience Conf Antimicrobial Agents Chemotherapy/Annual Meed Infect Dis Soc Am. 48/46 Oct. 28 Abstract V-4145.

Riechmann et al., 1988. Reshaping human antibodies for therapy. Nature. 332(6162):323-7.

Ruther and Muller-Hill, 1983. Easy identification of cDNA clones. Embo J. 2:1791-1794.

Scott et al., 1985. Cellular reactivity to respiratory syncytial virus in human colostrum and breast milk. J Med Virol. 17(1):83-93.

Seaver, Monoclonal antibodies in industry: More difficult than originally thought; Genetic Engineering News, vol. 14, No. 14, Aug. 1994, p. 10 and 21.

Sevier et al., 1981. Monoclonal antibodies in clinical immunology. Clin Chem. 27(11):1797-806.

Shreder, 2000. Synthetic haptens as probes of antibody response and immunorecognition; Methods; 20(3):372-9.

Stott et al., 1984. The characterization and uses of monoclonal antibodies to respiratory syncytial virus. Dev Biol Stand. 57:237-44.

Studnicka et al., 1994. Human-engineered monoclonal antibodies retain full specific binding activity by preserving non-CDR complementarity-modulating residues. Protein Eng. 7:805-814.

Takahashi et al. 1984. Rearranged immunoglobulin heavy chain variable region (VH) pseudogene that deletes the second complementarity-determining region. Proc Natl Acad Sci USA. 81: 5194-198.

Taylor et al., 1984. Monoclonal antibodies protect against respiratory syncytial virus infection in mice. Immunology. 52(1):137-42.

Taylor et al., 1992. Protective epitopes on the fusion protein of respiratory syncytial virus recognized by murine and bovine monoclonal antibodies. J Gen Virol. 73 (Pt 9):2217-23.

Van Der Merwe et al., 1993. Affinity and kinetic analysis of the interaction of the cell adhesion molecules rat CD2 and CD48. EMBO J. 12(13):4945-4954.

Van Der Merwe et al., 1994. Human cell-adhesion molecule CD2 binds CD58 (LFA-3) with a very low affinity and an extremely fast dissociation rate but does not bind CD48 or CD59. Biochemistry. 33(33):10149-10160.

Walsh et al., 1984. Protection from respiratory syncytial virus infection in cotton rats by passive transfer of monoclonal antibodies. Infect Immun. 43(2):756-8.

Ware et al., 1985. Human, rat or mouse hybridomas secrete high levels of monoclonal antibodies following transplantation into mice with severe combined immunodeficiency disease (SCID). J Immunol Methods. 85(2):353-61.

Watkins et al., 1997. Determination of the relative affinities of antibody fragments expressed in *Escherichia coli* by enzyme-linked immunosorbent assay. Anal Biochem. 253(1):37-45.

Watkins et al., 1998. Discovery of human antibodies to cell surface antigens by capture lift screening of phage-expressed antibody libraries. Anal Biochem. 256(2):169-77.

Weltzin et al., 1989. Binding and transepithelial transport of immunoglobulins by intestinal M cells: demonstration using monoclonal IgA antibodies against enteric viral proteins. J. Cell Biol. 108(5):1673-85.

Wilson et al., 1984. The structure of an antigenic determinant in a protein. Cell. 37(3):767-78.

Wu et al., 2008. Immunoprophylaxis of RSV Infection: Advancing from RSV-IGIV to Palivizumab and Motavizumab. Curr Topics Microbiol Immunol. 317:103-123.

Colman, 1994. Effects of amino acid sequence changes on antibody-antigen interactions; Res Immunol. 145(1):33-6.

Edelman et al., 1969. The Covalent Structure of an Entire gammaG Immunoglobulin Molecule. Proc Natl Acad Sci USA. 63:78-85.

Kudo et al., 1992. New strategies to establish human monoclonal antibodies; Tohoku J Exp Med. 168(2):323-327.

MacCallum et al., 1996. Antibody-antigen interactions: contact analysis and binding site topography. J Mol Biol. 262(5):732-45.

Morell et al., 1986. Clinical Use of Intravenous Immunoglobulins. Academic Press, London, pp. 285-294.

Wu et al., 2007. Development of Motavizumab, an Ultra-potent Antibody for the Prevention of Respiratory Syncytial Virus Infection in the Upper and Lower Respiratory Trace. J Mol Biol. 368(3): 652-65.

Adams et al., 1998. Increased affinity leads to improved selective tumor delivery of single-chain Fv antibodies. Cancer Res. 58(3):485-90.

Boder et al., 2000. Directed evolution of antibody fragments with monovalent femtomolar antigen-binding affinity. Proc Natl Acad Sci U S A. 97(20):10701-5.

Ichiyoshi et al., 1995. A human anti-insulin IgG autoantibody apparently arises through clonal selection from an insulin-specific "germline" natural antibody template. Analysis by V gene segment reassortment and site-directed mutagenesis. J Immunol. 154(1):226-38.

Jackson et al., 1998. Antigen specificity and tumour targeting efficiency of a human carcinoembryonic antigen-specific scFv and affinity-matured derivatives. Br. J. Cancer. 78(2):181-8.

Marks et al., 1992. By-passing immunization: building high affinity human antibodies by chain shuffling. Biotechnology (NY) 10(7):779-83.

Maynard et al., 2002. Protection against anthrax toxin by recombinant antibody fragments correlates with antigen affinity. Nat Biotechnol. 20(6):597-601.

Thompson et al., 1996. Affinity maturation of a high-affinity human monoclonal antibody against the third hypervariable loop of human immunodeficiency virus: use of phage display to improve affinity and broaden strain reactivity. J. Mol. Biol. 256(1):77-88.

Vancott et al., 1994. Dissociation rate of antibody-gp120 binding interactions is predictive of V3-mediated neutralization of HIV-1. J. Immunol. 153(1):449-59.

U.S. Appl. No. 10/900,230 (U.S. Publ. No. 2005/0002926)—Interview Summary dated Mar. 27, 2009.

U.S. Appl. No. 10/900,230 (U.S. Publ. No. 2005/0002926)—Office Action / Notice of Allowability dated Jun. 17, 2009.

U.S. Appl. No. 11/643,982 (U.S. Publ. No. 2007/0196916)—Office Action / Notice of Allowability dated Feb. 13, 2009.

U.S. Appl. No. 11/263,230 (U.S. Publ. No. 2006/0115485)—Office Action dated Mar. 30, 2009.

U.S. Appl. No. 09/796,848 (U.S. Publ. No. 2002/0098189)—Office Action dated Jan. 22, 2009.

U.S. Appl. No. 10/657,363 (U.S. Publ. No. 2004/0131609)—Office Action / Notice of Allowability dated Dec. 31, 2008.

U.S. Appl. No. 11/397,328 (U.S. Publ. No. 2006/0198840)—Office Action dated Feb. 13, 2009.

U.S. Appl. No. 11/649,455 (U.S. Publ. No. 2007/0122403)—Office Action dated Feb. 26, 2009.

U.S. Appl. No. 11/906,543 (U.S. Publ. No. 2008/0286270)—Office Action dated Jun. 12, 2009.

U.S. Appl. No. 12/559,375, filed Sep. 14, 2009, Young et al.

U.S. Appl. No. 10/657,363 (U.S. Publ. No. 2004/0131609)—Office Action dated Jul. 6, 2009.

U.S. Appl. No. 11/397,328 (U.S. Publ. No. 2006/0198840)—Office Action / Notice of Allowability dated Sep. 29, 2009.
U.S. Appl. No. 11/906,543 (U.S. Publ. No. 2008/0286270)—Office Action dated Oct. 19, 2009.

U.S. Appl. No. 10/657,363 (U.S. Publ. No. 2004/0131609)—Interview Summary dated Oct. 8, 2009.

* cited by examiner

DIQMTQSPST LSASVGDRVT ITC<u>KCQLSVGYMH</u> WYQQKPG    40
                                            *CDR L1*

KAPKLLIY <u>DTSKLAS</u> GVPSR FSGSGSGTEF TLTISSLQPD    80
          *CDR L2*

DFATYYC <u>FQGSGYPFT</u> FGGGTKLEIK                            106
         *CDR L3*

B

QVTLRESGPA LVKPTQTLTL TCTFSGFSLS <u>TSGMSVG</u> WIR    40
                                            *CDR H1*

QPPGKALEWL A <u>DIWWDDKKDYNPSLKS</u> RLT ISKDTSKNQV    80
                       *CDR H2*

VLKVTNMDPA DTATYYCAR <u>SMITNWYFDV</u> W GAGTTVTVSS    120
                               *CDR H3*

DIQMTQSPST LSASVGDRVT ITC<u>SASSSVGYMH</u> WYQQKPG  40
              *CDR L1*

KAPKLLIY <u>DTSKLAS</u> GVPSR FSGSGSGTEF TLTISSLQPD  80
   *CDR L2*

DFATYYC <u>FQGSGYPFT</u> FGGG TKVEIK  106
   *CDR L3*

B

QVTLRESGPA LVKPTQTLTL TCTFSGFSLS <u>TSGMSVG</u> WIR  40
              *CDR H1*

QPPGKALEWL A <u>DIWWDDKKDYNPSLKS</u> RLT ISKDTSKNQV  80
      *CDR H2*

VLKVTNMDPA DTATYYCAR <u>SMITNWYFDV</u> WGQGTTVTVSS  120
          *CDR H3*

DIQMTQSPST LSASVGDRVT ITC<u>SLSSRVGYMH</u> WYQQKPG    40
<div style="text-align:center">CDR L1</div>

KAPKLLIY <u>DTMYQSS</u> GVPSR FSGSGSGTEF TLTISSLQPD    80
<div style="text-align:center">CDR L2</div>

DFATYYC <u>FQGSGYPFT</u> FGGG TKVEIK    106
<div style="text-align:center">CDR L3</div>

B

QVTLRESGPA LVKPTQTLTL TCTFSGFSLS <u>TAGMSVG</u> WIR    40
<div style="text-align:center">CDR H1</div>

QPPGKALEWL A <u>DIWWDGKKSYNPSLKD</u> RLT ISKDTSKNQV    80
<div style="text-align:center">CDR H2</div>

VLKVTNMDPA DTATYYCAR <u>DMIFNFYFDV</u> WGQGTTVTVSS    120
<div style="text-align:center">CDR H3</div>

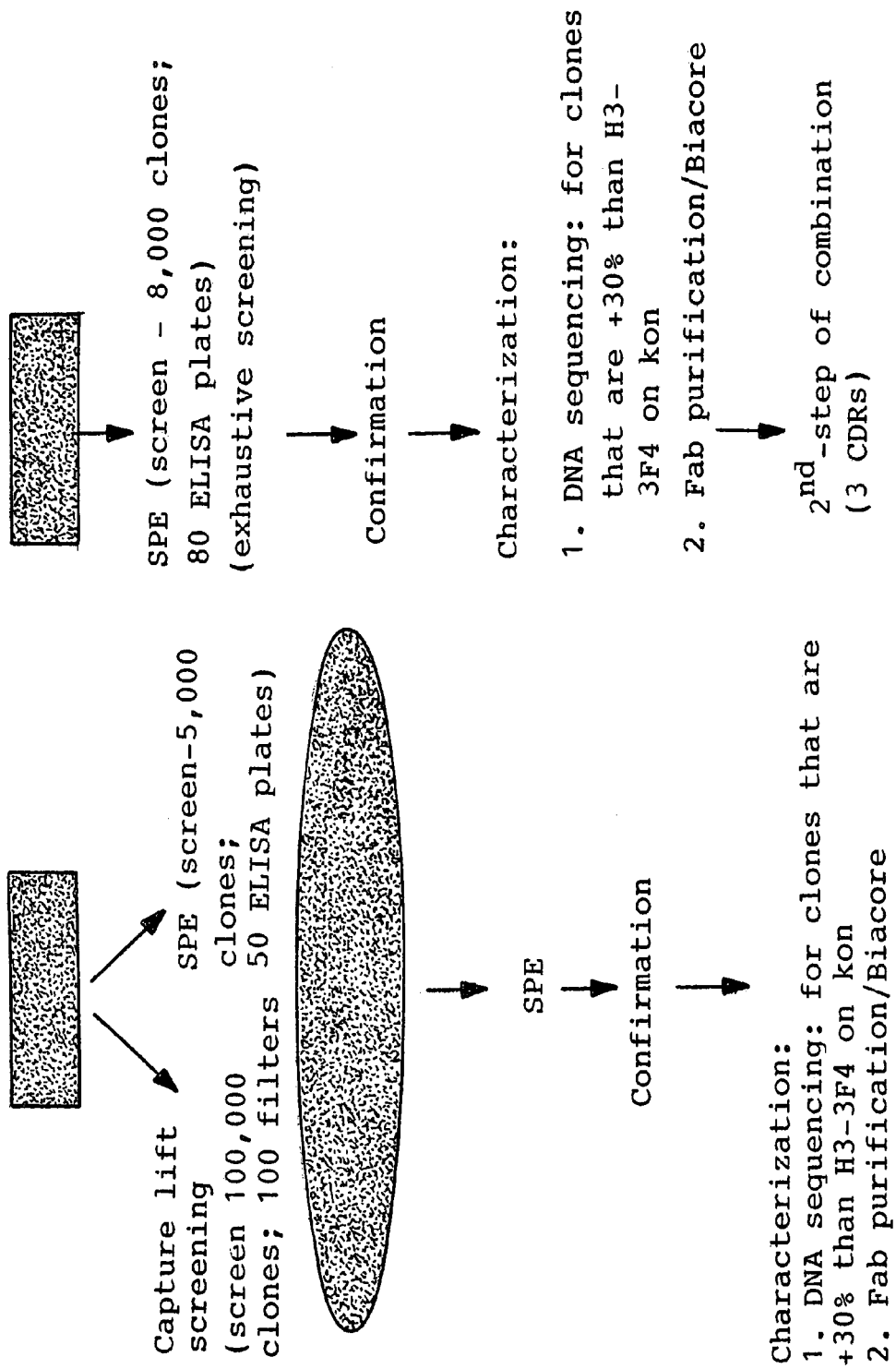

HIGH POTENCY RECOMBINANT ANTIBODIES AND METHOD FOR PRODUCING THEM

This application claims priority of U.S. Provisional Application Ser. No. 60/186,252, filed 1 Mar. 2000, the disclosure of which is hereby incorporated by reference in its entirety.

FIELD OF THE INVENTION

The present invention relates to high potency antibodies, methods of increasing antibody potency and to methods of using such antibodies for prevention and treatment of diseases.

BACKGROUND OF THE INVENTION

Antibodies have been, and are currently being, developed for the prevention and treatment of various diseases, especially those caused by infectious microorganisms, such as the viruses.

One approach has been the development of antibodies, especially neutralizing monoclonal antibodies, some with high specific neutralizing activity. One drawback to this approach has been the need to produce human antibodies rather than those of mouse or rat and thus minimize the development of human anti-mouse or anti-rat antibody responses, which potentially results in further immune pathology.

An alternative approach has been the production of human-murine chimeric antibodies in which the genes encoding the mouse heavy and light chain variable regions have been coupled to the genes for human heavy and light chain constant regions to produce chimeric, or hybrid, antibodies. For example, a humanized anti-RSV antibody has been prepared and is currently being marketed. [See: Johnson, U.S. Pat. No. 5,824,307]

In some cases, mouse complementarity determining regions (CDRs) have been grafted onto human constant and framework regions with some of the mouse framework amino acids (amino acids in the variable region of the antibody but outside of the CDRs) being substituted for correspondingly positioned amino acids from a human antibody of like specificity to provide a so-called "humanized" antibody [see, for example, Queen, U.S. Pat. Nos. 5,693,761 and 5,693,762]. However, such antibodies contain intact mouse CDR regions and have met with mixed effectiveness and exhibiting affinities often no higher than $10^7$ to $10^8$ $M^{-1}$.

The production of high potency antibodies (i.e., antibodies with high biological activity, such as antigen neutralizing ability), including antibodies with ultra high affinity for the target antigen, would be desirable from the point of view of both the neutralizing ability of such an antibody as well as from the more practical aspects of requiring less antibody in order to achieve a desirable degree of clinical effectiveness, thereby cutting costs of use.

Antibody affinity is measured by the binding constant of the antibody for a particular antigen, and such binding constant is often calculated by the ratio of the rate constant for antibody-antigen complex formation (referred to as the "$k_{on}$" value) to the rate constant for dissociation of said complex (the "$k_{off}$" value). In accordance with the present invention, it has been determined that antibody potency is a function of the $k_{on}$ value, irrespective of specificity. The present invention thus provides a solution to problems of achieving high antibody potency in that the higher the $k_{on}$ value, the higher the potency of the antibody thereby affording high potency antibodies and a method for producing them.

BRIEF SUMMARY OF THE INVENTION

In accordance with an aspect of the present invention, there are provided high potency antibodies useful in the treatment and/or prevention of a disease. In another aspect, the potency of an antibody is increased by increasing the rate constant for antigen-antibody complex formation (the "$k_{on}$" value).

In one aspect, the present invention relates to high potency antibodies, other than vitaxin, including immunologically active portions, fragments, or segments thereof, having a $k_{on}$ of at least $2.5 \times 10^5$ $M^{-1}$ $s^{-1}$, preferably at least about $5 \times 10^5$ $M^{-1}$ $s^{-1}$, and most preferably at least about $7.5 \times 10^5$ $M^{-1}$ $sec^{-1}$. antibodies may also have a high affinity (at least about $10^9$ $M^{-1}$).

In another aspect, the present invention relates to high potency neutralizing antibodies, including immunologically active portions, fragments, or segments thereof, having a $k_{on}$ of at least $2.5 \times 10^5$ $M^{-1}$ $s^{-1}$, preferably at least about $5 \times 10^5$ $M^{-1}$ $s^{-1}$, and most preferably at least about $7.5 \times 10^5$ $M^{-1}$ $sec^{-1}$. Such antibodies may also have a high affinity (at least about $10^9$ $M^{-1}$).

It is a further object of the present invention to provide methods for increasing the potency of neutralizing antibodies by increasing the $k_{on}$ value with respect to a given antigen without changing the epitope to which the antibody binds.

It is a still further object of the present invention to provide a means of screening antibodies for properties that will insure high potency with respect to a desired antigen, said potency being at least 2- to 10-fold over known antibodies.

More specifically, it is an object of the present invention to produce antibodies having $k_{on}$ values at least as high as $2.5 \times 10^5$ $M^{-1}$ $sec^{-1}$, preferably at least $5 \times 10^5$ $M^{-1}$ $sec^{-1}$, and most preferably as high as $7.5 \times 10^5$ $M^{-1}$ $sec^{-1}$.

It is also an object of the present invention to provide high affinity, high potency antibodies having high specificity toward one or more antigens exhibited by an infectious microorganism (or microbe), especially one that causes infection of the respiratory system, most especially viruses.

In one embodiment, the present invention provides antibodies having substantially the variable chain framework (FR) regions of the antibody disclosed in FIG. 1 (with the same specificity as this antibody) but wherein the polypeptide structures contain one or more amino acid differences in one or more of the CDRs (or complementarity determining regions) thereof. In a preferred embodiment, the antibodies of the present invention will differ from the antibody of FIGS. 1 or 2 (hereafter, the "basic structure" or "reference structure") only in the sequences of one or more of the CDRs, including L1, L2, L3, H1, H2 and H3. One preferred sequence is shown in FIG. 3.

It is another object of the present invention to provide compositions comprising the antibodies disclosed herein wherein said antibodies are suspended in a pharmacologically acceptable carrier, diluent or excipient.

It is a still further object of the present invention to provide methods of preventing and/or treating diseases, such as is caused by viruses, especially respiratory syncytial virus, comprising the administering to a patient at risk thereof, or afflicted therewith, of a therapeutically effective amount of a composition containing an antibody as disclosed herein.

BRIEF DESCRIPTION OF THE DRAWINGS

FIG. 1 shows the amino acid sequence of the light and heavy chain variable regions of a high affinity monoclonal antibody whose potency can be increased by the methods of the present invention. For reference purposes, this antibody is the MEDI-493 antibody sequence disclosed in Johnson et al, *J. Infect. Dis.*, 176:1215-1224 (1997). Here, the CDR regions are underlined while non-underlined residues form the framework regions of the variable regions of each polypeptide structure. In this structure, CDRs are derived from a mouse antibody while the framework regions are derived from a human antibody. The constant regions (not shown) are also derived from a human antibody. FIG. 1A shows the light chain variable region (SEQ ID NO: 1) and FIG. 1B shows the heavy chain variable region (SEQ ID NO: 2) of the light and heavy chains, respectively.

FIG. 2 shows the heavy and light chain variable regions for a different basic or reference polypeptide sequence. Again, CDR regions are underlined. This sequence differs from FIG. 1 in the first 4 residues of CDR L1 of the light chain, residue 103 of the light chain and residue 112 of the heavy chain. All of the high potency neutralizing Fab structures of the present invention (CDR structures shown in Table 2) use the framework sequences of this reference or basic structure. FIG. 2A shows the light chain (SEQ ID NO: 3) and FIG. 2B shows the heavy chain (SEQ ID NO: 4) variable regions.

FIG. 3 shows the heavy (SEQ ID NO: 36) and light chain (SEQ ID NO: 35) variable regions of a preferred embodiment of the present invention. This preferred antibody has several high $k_{on}$ CDRs (or high potency CDRs) present, which give rise to higher association rate constants (i.e., $k_{on}$) than the basic or reference antibody of FIG. 2 and thus higher potency. This preferred antibody has the same framework amino acid sequences as the sequence of FIG. 2 and, for purposes of the present disclosure, is denoted as "clone 15" in Tables 2 and 3, below. These sequences are readily generated by the methods disclosed herein, all of which are readily known to those of skill in the art. The kinetic constants were measured according to the procedure of Example 1 and the potency determined as described in Example 2.

FIG. 5 shows a schematic diagram for the screening procedure used for the antibodies of the present invention. "SPE" refers to a single point ELISA. "H3-3F4" is a designation for clone 4 of Tables 2 and 3.

DETAILED SUMMARY OF THE INVENTION

Figure 4:
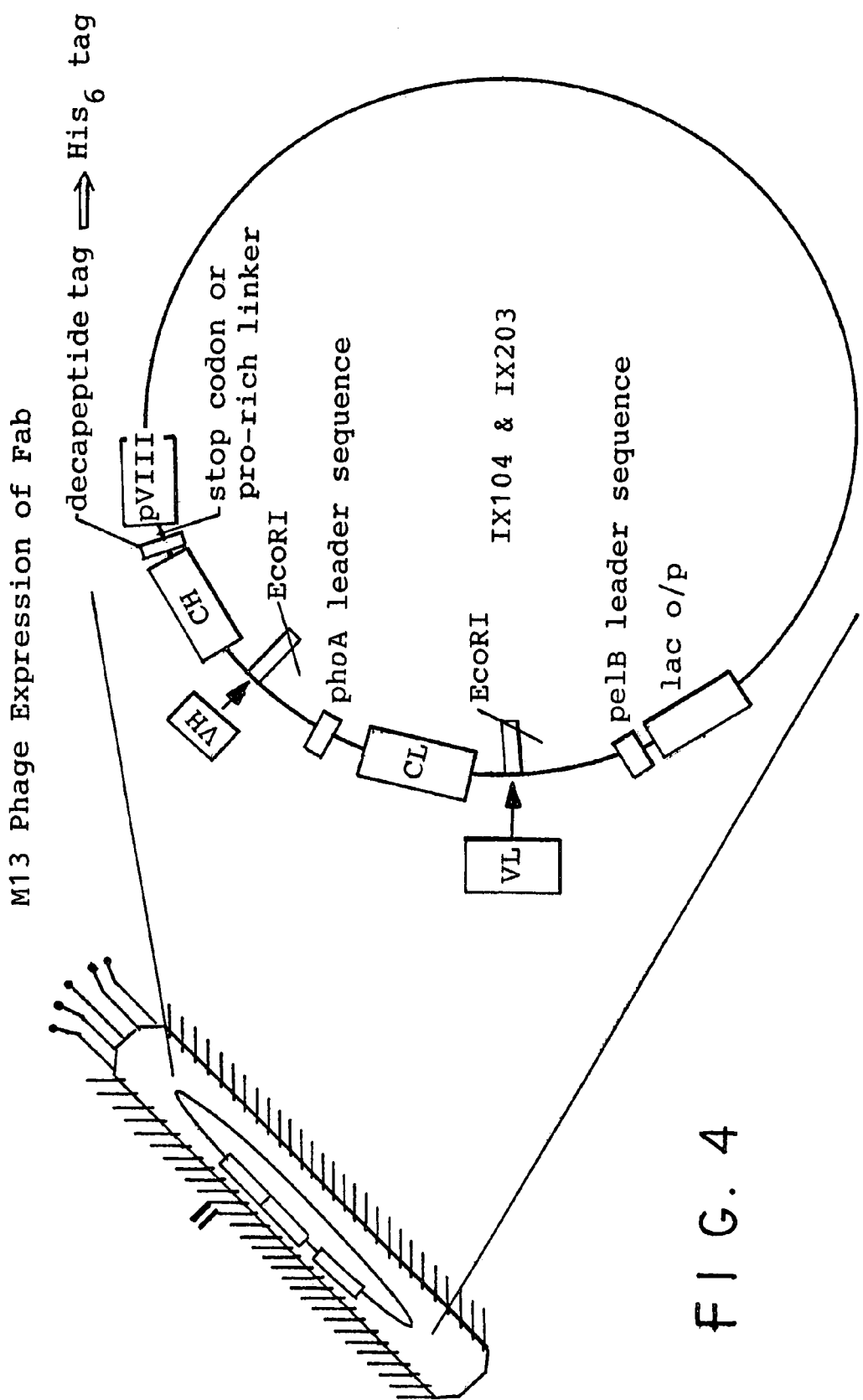
FIG. 4 shows a schematic diagram of the use of phage M13 for generation of Fab fragments in accordance with the present invention and using a histidine tag sequence (6 histidine residues) to facilitate purification.

In accordance with an aspect of the present invention, there are provided high potency antibodies useful in the treatment and/or prevention of disease. In another aspect, the potency of an antibody is increased by increasing the rate constant for antigen-antibody complex formation, which is referred to as the "$k_{on}$" value, by replacement of CDR sequences of such antibody with high potency CDR sequences in their place.

In one aspect, the present invention relates to high potency antibodies, other than vitaxin, including immunologically active portions, fragments, or segments of said high potency antibodies, having a $k_{on}$ of at least 2.5×10$^5$ M$^{-1}$ s$^{-1}$, preferably at least about 5×10$^5$ M$^{-1}$ s$^{-1}$, and most preferably at least about 7.5×10$^5$ M$^{-1}$ sec$^{-1}$. Such antibodies may also have a high affinity (at least about 10$^9$ M$^{-1}$).

In one aspect, the present invention relates to high potency neutralizing antibodies, including immunologically active portions, fragments, or segments thereof, having a $k_{on}$ of at least 2.5×10$^5$ M$^{-1}$ s$^{-1}$, preferably at least about 5×10$^5$ M$^{-1}$ s$^{-1}$, and most preferably at least about 7.5×10$^5$ M$^{-1}$ sec$^{-1}$. Such antibodies may also have a high affinity (at least about 10$^9$ M$^{-1}$).

The present invention is directed to methods of producing antibodies, neutralizing or non-neutralizing, having high potency, or biological activity, preferably having an affinity of at least about 10$^9$ M$^1$, and having a $k_{on}$ value of at least about 2.5×10$^5$ M$^{-1}$ sec$^{-1}$, preferably at least about 5×10$^5$ M$^{-1}$ sec$^{-1}$, and most preferably at least about 7.5×10$^5$ M$^{-1}$ s$^{-1}$.

With the advent of methods of molecular biology and recombinant DNA technology, it is now possible to produce antibodies, including active fragments thereof, by recombinant means and thereby generate gene sequences that code for specific amino acid sequences found in the polypeptide structure of the antibodies. This has permitted the ready production of antibodies having sequences characteristic of neutralizing antibodies from different species and sources.

Regardless of how they are constructed, antibodies have a similar overall 3 dimensional structure usually given as $L_2H_2$ wherein the molecule commonly comprises 2 light (L) amino acid chains and 2 heavy (H) amino acid chains. Both chains have regions capable of interacting with a structurally complementary antigenic target. The regions interacting with the target are referred to as "variable" or "V" regions and are characterized by differences in amino acid sequence from antibodies of different antigenic specificity.

The variable regions of either H or L chains contain the amino acid sequences capable of specifically binding to antigenic targets. Within these sequences are smaller sequences dubbed "hypervariable" because of their extreme variability between antibodies of differing specificity. Such hypervariable regions are called "complementarity determining regions" or "CDR" regions. These CDR regions account for the basic specificity of the antibody for a particular antigenic determinant structure.

The CDRs represent non-contiguous stretches of amino acids within the variable regions but the positional locations of these critical amino acid sequences within the variable heavy and light chain regions have been found to have similar locations within the amino acid sequences of the immunoglobulin structure. The variable heavy and light chains of all antibodies each have 3 CDR regions, each non-contiguous with the others (termed L1, L2, L3, H1, H2, H3) for the respective light and heavy chains. The accepted CDR regions have been described by Kabat et al, *J Biol. Chem.* 252:6609-6616 (1977). The numbering scheme is shown in FIGS. 1-3, where the CDRs are underlined and the numbers follow the Kabat scheme.

In all mammalian species, antibody polypeptides contain constant (i.e., highly conserved) and variable regions comprising both CDRs and so-called "framework regions," the latter made up of amino acid sequences within the variable region but outside the CDRs.

Among the properties commonly used to characterize an antibody, or fragment thereof, are the specificity and affinity of the antibody. Specificity refers to the particular ligand, or antigenic structure, that the antibody binds strongly, or most strongly, to. Affinity refers to a quantitative measure of the strength of binding of the antibody to a particular ligand and is given in terms of an "affinity constant." Such affinity constants may be determined as either association or dissociation constants and represent the ratio of the equilibrium concentrations of the free ligand and free antibody with respect to the antibody-ligand complex. As used herein, affinity will be given as an association constant.

Such constants are commonly measured by the kinetics of antigen-antibody complex formation, with the rate constant for association to form the complex being denoted as the $k_{on}$ and the rate constant for dissociation denoted as the $k_{off}$. Measurement of such constants is well within the abilities of those in the art. The antibody and respective antigen combine to form a complex as follows:

Antibody(Ab)+Antigen(Ag)⇌Ab-Ag

Here, the affinity constant is given as an association constant and thus represents:

$$K_a = \frac{[Ab-Ag]}{[Ab][Ag]}$$

where $K_a$=the association (or affinity) constant while the brackets indicate molar concentration of the enclosed species. For a given set of conditions such as temperature, pressure and ionic strength, the ratio of the concentration of the complex to the product of the concentrations of the reacting species is constant. So long as saturating conditions are not reached for the antibody or antigen (ligand), a change in concentration of either binding species will alter the concentration of the complex (Ab-Ag) by an amount dictated by the above equation (sine $K_a$ is constant). Such interaction operates according to a mass-action law.

In addition, this relationship depends on concentrations and not on absolute amount of the species present so that overall volume is also relevant to any measurements of affinity. Thus, if the reaction occurs in half the volume, twice as much complex will be formed because each reactant species (Ab and Ag) is now present at twice the concentration and so almost four times as much complex will be formed. Conversely, dilution may greatly reduce concentration of the Ab-Ag complex. In general, the kinetics of antigen-antibody interaction are well known to those skilled in the art.

Such antibody-antigen reaction can be described kinetically as a dynamic equilibrium where the affinity constant can be measured as a ratio of the individual rate constants for formation and dissociation of the complex:

$$Ab + Ag \underset{k_{off}}{\overset{k_{on}}{\rightleftharpoons}} Ab - Ag$$

Thus, the $k_{on}$ value is the rate constant, or specific reaction rate, of the forward, or complex-forming, reaction, measured in units: $M^{-1} \sec^{-1}$. The $k_{off}$ value is the rate constant, or specific reaction rate, for dissociation of the Ab-Ag complex and is measured in units of $\sec^{-1}$.

The values of $k_{on}$ for the antibodies, and active fragments thereof, of the present invention were measured using the BIAcore protocol and equipment as disclosed in the Examples.

In accordance with the foregoing, the present invention relates to high potency neutralizing antibodies, including immunologically active portions, fragments, and/or segments thereof, having a $k_{on}$ of at least $2.5 \times 10^5$ $M^{-1}$ $s^{-1}$, preferably at least about $5 \times 10^5$ $M^{-1}$ $s^{-1}$, and most preferably at least about $7.5 \times 10^5$ $M^{-1}$ $s^{-1}$.

As used herein, the terms "portion," "segment," and "fragment," when used in relation to polypeptides, refer to a continuous sequence of residues, such as amino acid residues, which sequence forms a subset of a larger sequence. For example, if a polypeptide were subjected to treatment with any of the common endopeptidases, such as trypsin, chymotrypsin, pepsin, papain, etc., the oligopeptides resulting from such treatment would represent portions, segments or fragments of the starting polypeptide. Such proteainases are commonly used to generate fragments of antibodies, such as those described herein, although such fragments can now more easily be generated by direct cloning or synthesis of the particular polypeptide desired to be produced.

The antibodies of the present invention are high potency antibodies, generally exhibiting high $k_{on}$ values. For purposes of the present disclosure, the term "high potency" refers to a potency reflected by an $EC_{50}$ (or effective concentration showing at least a reduction of 50% in the $OD_{450}$ in the below described microneutralization assay) of below about 6 nM (nanomolar or $10^{-9}$ molar). The antibodies according to the present invention may be neutralizing (causing destruction of the target species, such as a virus, and thereby decreasing viral load). An antibody not neutralizing for one use may be neutralizing for a different use.

The high potency antibodies of the present invention may have specificity for antigenic determinants found on microbes and are capable of neutralizing said microbes by attaching thereto. In accordance with the present invention, such microbes are most often viruses, bacteria or fungi, especially organisms that cause respiratory disease and most preferably viruses. A specific example, used in the examples herein, is respiratory syncytial virus (RSV); another example is parainfluenza virus (PIV).

The high potency antibodies of the present invention may also have specificity for antigens displayed on the surfaces of cancer cells (but will generally not include antibodies, such as vitaxin, that are non-neutralizing. (See: Wu et al., *Proc. Natl. Acad. Sci.* 95:6037-6042 (1998)) The antibodies of the present invention also include antibodies for use in other non-neutralizing reactions.

The high potency antibodies of the present invention may also have specificity for chemical substances such as toxic substances, or toxins, or for the products of toxins, including, but not limited to, products produced by an organism's metabolism of such toxin(s). For example, the high potency antibodies of the present invention may be useful in nullifying, or otherwise ameliorating, the effects of addictive drugs, such as cocaine.

The high potency antibodies of the present invention may also have high affinity for their specific antigen, such as the F antigen of RSV, and, where such high affinity is exhibited, the affinity constant $(K_a)$ of such antibodies is at least about $10^9$ $M^{-1}$, preferably at least about $10^{10}$ $M^{-1}$, and most preferably at least about $10^{11}$ $M^{-1}$.

The antibodies of the present invention exhibit high potency when measured in, for example, the microneutralization assay described in Example 2. In that assay, high potency is measured by the $EC_{50}$ value and commonly have an $EC_{50}$ of less than about 6.0 nM (nanomolar or $10^{-9}$ M), preferably less than about 3.0 nM, and most preferably less than about 1.0 nM. In general, the lower the $EC_{50}$, the higher the potency, or biological activity.

The high potency antibodies of the present invention exhibit such high potency due to their high $k_{on}$ values, which is determined by the amino acid sequences making up the framework (FR) and complementarity determining regions (CDRs). These antibodies, or active fragments thereof, have high potency complementarity determining regions (CDR) within their amino acid sequences. The high potency neutralizing antibodies of the present invention may comprise at least 2 high potency CDRs, or 3 high potency CDRs, or even 4 high potency CDRs, or 5 high potency CDRs, and may even comprise 6 high potency CDRs. Of course, in the latter case, all 6 CDRs of the antibody, or active fragments thereof, are high potency CDRs. In accordance therewith, such high potency neutralizing antibodies of the present invention have high potency CDRs that consist of one each of light chain CDRs L1 (CDR L1), L2 (CDR L2), and L3 (CDR L3) and heavy chain CDRs H1 (CDR H1), H2 (CDR H2) and H3 (CDR H3).

In specific embodiments of such high potency antibodies, said high potency CDRs have amino acid sequences selected from the group consisting of SEQ ID NO: 11, 12, 13 and 56 for CDR L1, SEQ ID NO: 14, 15, 16, 17, 18, 19, 20, 21, 22, 57 and 58 for CDR L2, SEQ ID NO: 23 for CDR L3, SEQ ID NO: 24 and 25 for CDR H1, SEQ ID NO: 26, 27, 28, 29, 30 and 55 for CDR H2, SEQ ID NO: 31, 32, 33 and 34 for CDR H3.

In preferred embodiments, the high potency neutralizing antibodies of the present invention comprise variable heavy and light chains with amino acid sequences selected from the group consisting of SEQ ID NO: 35 and 36.

The present invention further relates to a process for producing a high potency antibody comprising:

(a) producing a recombinant antibody, including immunologically active fragments thereof, comprising heavy and light chain constant regions derived from a mammalian antibody and heavy and light chain variable regions containing one or more framework and/or complementarity determining regions (CDRs) having preselected amino acid sequences;

(b) screening said recombinant antibodies for high $k_{on}$ when said antibody reacts in vitro with a selected antigen; and (c) selecting antibodies with said high $k_{on}$.

The antibodies produced according to the present invention will commonly have high affinity constants and high $k_{on}$ values, the latter yielding high biological activity, or potency. In specific embodiments, the high potency antibodies produced according to the present invention commonly have a $k_{on}$ of at least about $2.5 \times 10^5$ M$^{-1}$ s$^{-1}$, preferably at least about $5 \times 10^5$ M$^{-1}$ s$^{-1}$, and most preferably at least about $7.5 \times 10^5$ M$^{-1}$ s$^{-1}$.

In one embodiment, the processes of the invention produce a high potency antibody wherein the preselected amino acid sequences producing a high $k_{on}$ (and resulting high potency) are present in either both framework region and at least two or three CDR regions, perhaps all six CDR regions, of the antibody or are restricted to just CDR regions.

In another embodiment, the preselected amino acid sequences producing a high $k_{on}$ are present in either both framework region and at least three CDR regions of the antibody or are restricted to just CDR regions.

In an additional embodiment, the preselected amino acid sequences producing a high $k_{on}$ are present in either both framework region and at least four CDR regions of the antibody or are restricted to just CDR regions.

In addition, the antibodies produced according to the present invention may be complete tetrameric antibodies, having the $H_2L_2$ structure, or may be fragments of such antibody structures, including single chain antibodies or fragments such as Fab or F(ab)$_2$' fragments.

In accordance with the present invention, the antigens for which the antibodies are specific are often, but not always, antigens expressed by viruses, such as respiratory syncytial virus (RSV) or parainfluenza virus (PIV).

The present invention also relates to a process for producing a high potency antibody comprising producing a recombinant antibody comprising heavy and light chain constant region derived from a mammalian antibody and heavy and light chain variable regions containing framework and/or complementarity determining regions (CDR) wherein at least one CDR is a high $k_{on}$ (or high potency) CDR having an amino acid sequence not found in nature and wherein the presence of said CDR results in a high $k_{on}$.

In specific embodiments, the processes of the present invention produce high potency recombinant antibodies wherein the recombinant high $k_{on}$ antibody comprises at least two high $k_{on}$ CDRs, possibly three high $k_{on}$ CDRs, and even four high $k_{on}$ CDRs, and as many as five or six high $k_{on}$ CDRs. The presence of such CDR sequences result in the antibody, or fragment, exhibiting a high $k_{on}$ and thereby a high potency.

In further embodiments of the methods of the invention, the aforementioned high association constant of the antibodies produced by the methods of the invention are at least about $2.5 \times 10^5$ M$^{-1}$ s$^{-1}$, preferably at least about $5 \times 10^5$ M$^{-1}$ s$^{-1}$, and most preferably at least about $7.5 \times 10^5$ M$^{-1}$ s$^{-1}$.

The present invention further relates to a process for producing a high potency antibody comprising:

(a) producing a recombinant antibody, including immunologically active fragments thereof, comprising heavy and light chain constant regions derived from a mammalian antibody and heavy and light chain variable regions containing one or more framework and/or complementarity determining regions (CDRs) having preselected amino acid sequences;

(b) screening said recombinant antibodies for both high affinity and high $k_{on}$ when said antibody reacts in vitro with a selected antigen; and (c) selecting antibodies with both high affinity and high $k_{on}$.

In preferred embodiments of the present invention, the processes disclosed herein produce high potency antibodies having both high affinity and high $k_{on}$ wherein the affinity constant is at least $10^9$ M$^{-1}$ and $k_{on}$ is at least $2.5 \times 10^5$ M$^{-1}$ s$^{-1}$, especially where said affinity is at least $10^{10}$ M$^{-1}$ and said $k_{on}$ is at least $2.5 \times 10^5$ M$^{-1}$ S$^{-1}$, most especially where said affinity constant is at least $10^{11}$ M$^{-1}$ and said $k_{on}$ is at least $2.5 \times 10^5$ M$^{-1}$ s$^{-1}$, with most preferred embodiments having very high affinity and $k_{on}$, especially where said affinity is at least $10^9$ M$^{-1}$ and said $k_{on}$ is at least $5 \times 10^5$ M$^{-1}$ s$^{-1}$, and most especially where the affinity constant is at least $10^{10}$ M$^{-1}$ and $k_{on}$ is at least $2.5 \times 10^5$ M$^{-1}$ s$^{-1}$, a most especially preferred embodiment being one wherein the processes of the invention produce a high potency antibody wherein the affinity constant is at least $10^{11}$ M$^{-1}$ and the $k_{on}$ is at least $7.5 \times 10^5$ M$^{-1}$ s$^{-1}$. It is to be understood that, where high affinity is also sought, any combination of the above mentioned affinity ($K_a$) and kinetic association ($k_{on}$) values are within the present invention.

These embodiments of the present invention also include processes wherein the preselected amino acid sequence producing a high $k_{on}$ is present in either both framework region and CDR regions, or just CDR regions, and wherein such sequences, selected from SEQ ID NO: 11 to 34 and 55 to 58, are present in 1, 2, 3, 4, 5, or all 6, CDR regions, wherein the individual CDR sequence is selected from the individual sequences as disclosed herein. Methods of doing this are well within the skill of those in the art and will not be discussed further herein.

The methods of the present invention are not limited to merely producing novel high affinity antibodies that are specific for a particular antigen and which have been produced without regard to already existing immunogenic molecules and structures. Thus, the methods disclosed herein provide a means for selected modifications to the structures of known antibody molecules, thereby producing increases in the $k_{on}$ of such antibodies and concomitant increased biological activity. This is accomplished by selective incorporation of the high potency CDR sequences disclosed herein.

In separate embodiments of the present invention, the antibody whose potency is to be increased will have an initial and/or final affinity constant of at least $10^9$ $M^{-1}$, preferably at least about $10^{10}$ $M^{-1}$, and most preferably at least about $10^{11}$ $M^{-1}$.

In accordance with the present invention, the antibodies produced according to the methods of the invention will have higher $k_{on}$ constants after amino acid changes to produce high potency sequences of the invention and as a result of said amino acid changes, especially where the $k_{no}$ value following said amino acid changes is at least $2.5 \times 10^5$ $M^{-1}$ $sec^{-1}$, especially at least about $5 \times 10^5$ $M^{-1}$ $s^{-1}$, and most especially at least about $7.5 \times 10^5$ $M^{-1}$ $s^{-1}$ (regardless of the particular affinity constant) ($K_a$).

In applying the methods of the present invention it is to be understood that the aforementioned changes in amino acid sequence used to increase the potency of an antibody, or active fragments thereof, or the use of selected amino acid sequences to produce high potency antibodies, or active high potency fragments thereof, achieve said high potency, or increased potency, through the production of high $k_{on}$ values. Because the affinity constant is a numerical ratio of $k_{on}$ to $k_{off}$, an increased $k_{on}$ may result in increased affinity if the $k_{off}$ is not changed by the same factor. Thus, high potencies of the antibodies produced according to the present methods are a function of the value of $k_{on}$ and not the value of $K_a$ (the affinity constant). For example, the use of selected amino acid sequences in the CDRs of an antibody molecule may result in a sizeable increase in both association ($k_{on}$) and dissociation ($k_{off}$) rate constants and, if both are increased by the same factor, the result is a high, or higher, potency (due to the higher $k_{on}$) but with no resulting increase in $K_a$ (because the ratio of the $k_{on}$ to $k_{off}$ is the same). Conversely, where use of such preselected amino acid sequences within the CDRs of a high potency antibody results in a decreased $k_{off}$ and no increased $k_{on}$, the result is an antibody, or active fragment thereof, with higher affinity but with little or no increase in potency. Thus, it has been found that there is little or no change in potency where the $k_{off}$ value alone changes (because $K_a$ is the ratio of $k_{on}$ to $k_{off}$) but $k_{on}$ remains constant despite a numerical change in $K_a$.

In accordance with the present invention, several convenient methods are available for measurement of the potency of antibodies, or active fragments thereof, such as Fab fragments. One such method uses the cotton rat model, details of which are disclosed in the examples provided below. Another is the microneutralization assay (see Example 2).

Also in accordance with the present invention, there is provided a process for preventing or treating a disease comprising administering to a patient at risk of such disease, or afflicted with such disease, a therapeutically (or prophylactically) effective amount of a high potency antibody, or active fragment thereof, having a polypeptide sequence as disclosed herein or produced according to the methods disclosed herein. In a preferred embodiment, the disease is caused by a virus, especially one selected from the group respiratory syncytial virus and parainfluenza virus.

The highly potent neutralizing antibodies of the present invention are achieved through generating appropriate antibody gene sequences, i.e., amino acid sequences, by arranging the appropriate nucleotide sequences and expressing these in a suitable cell line. Any desired nucleotide sequences can be produced using the method of codon based mutagenesis, as described, for example, in U.S. Pat. Nos. 5,264,563 and 5,523,388 (the disclosures of which are hereby incorporated by reference in their entirety). Such procedures permit the production of any and all frequencies of amino acid residues at any desired codon positions within an oligonucleotide. This can include completely random substitutions of any of the 20 amino acids at an desired position or in any specific subset of these. Alternatively, this process can be carried out so as to achieve a particular amino acid a desired location within an amino acid chain, such as the novel CDR sequences according to the invention. In sum, the appropriate nucleotide sequence to express any amino acid sequence desired can be readily achieved and using such procedures the novel CDR sequences of the present invention can be reproduced. This results in the ability to synthesize polypeptides, such as antibodies, with any desired amino acid sequences. For example, it is now possible to determine the amino acid sequences of any desired domains of an antibody of choice and, optionally, to prepare homologous chains with one or more amino acids replaced by other desired amino acids, so as to give a range of substituted analogs.

In applying such methods, it is to be appreciated that due to the degeneracy of the genetic code, such methods as random oligonucleotide synthesis and partial degenerate oligonucleotide synthesis will incorporate redundancies for codons specifying a particular amino acid residue at a particular position, although such methods can be used to provide a master set of all possible amino acid sequences and screen these for optimal function as antibody structures or for other purposes. Such methods are described in Cwirla et al, *Proc. Natl. Acad. Sci.* 87:6378-6382 (1990) and Devlin et al., Science 249:404-406 (1990). Alternatively, such antibody sequences can be synthesized chemically or generated in other ways well known to those skilled in the art.

In accordance with the invention disclosed herein, enhanced antibody variants can be generated by combining in a single polypeptide structure one, two or more novel CDR sequences as disclosed herein (see, for example, SEQ ID NO: 11-34), each shown to independently result in enhanced potency or biological activity. In this manner, several novel amino acids sequences can be combined into one antibody, in the same or different CDRs, to produce antibodies with desirable levels of biological activity. Such desirable levels will often result from producing antibodies whose $k_{on}$ values are at least about $2.5 \times 10^5$ $M^{-1}$ $sec^{-1}$. By way of non-limiting example, 3 such novel CDR sequences may be employed and the resulting antibodies screened for potency, or biological activity, using either the cotton rat protocol or the microneutralization protocol described herein, where the said antibody demonstrates high affinity for a particular antigenic structure, such as the F antigen of RSV. The overall result would thus be an iterative process of combining various single amino acid substitutions and screening the resulting antibodies for antigenic affinity and potency in a step by step manner, thereby insuring that potency is increased without sacrifice of a desirably high, or at least minimum value for, affinity.

Using the novel sequences and methods of the present invention, such an approach would avoid the time and expense of generating and screening all possible permutations and combinations of antibody structure in an effort to find the antibody with the maximum efficacy. Conversely, complete randomization of a single 10 amino acid residue CDR would generate over 10 trillion variants, a number virtually impossible to screen.

This iterative method can be used to generate double and triple amino acid replacements in a stepwise process so as to narrow the search for antibodies having higher affinity.

Conversely, it must be appreciated that not all locations within the sequences of the different antibody domains may be equal. Substitutions of any kind in a particular location may be helpful or detrimental. In addition, substitutions of certain kinds of amino acids at certain locations may likewise be a plus or a minus regarding affinity. For example, it may not be necessary to try all possible hydrophobic amino acids at a given position. It may be that any hydrophobic amino acid will do as well. Conversely, an acidic or basic amino acid at a given location may provide large swings in measured affinity. It is therefore necessary also to learn the "rules" of making such substitutions but the determination of such "rules" does not require the study of all possible combinations and substitutions—trends may become apparent after examining fewer than the maximum number of substitutions.

In accordance with the present invention, such rules determine the amino acid changes that must be made in the CDR regions of antibodies, or the amino acid sequences that must be prepared in wholly novel and synthetic antibody polypeptides, so as to achieve high affinities. However, it has now been discovered that, while high affinity is often a property of antibodies useful in therapeutic applications, such antibodies do not always have a sufficient potency to afford practical utility in such uses.

As already described, affinity is measured by the ratio of the $k_{on}$ and $k_{off}$ constants. For example, a $k_{on}$ of $10^5$ $M^{-1}$ $sec^{-1}$ and a $k_{off}$ of $10^5$ $sec^{-1}$ would combine to give an affinity constant of $10^{10}$ $M^{-1}$ (see values in Table 3). However, antibodies showing such high affinity may still lack the potency required to make them useful therapeutic agents. In accordance with the present invention, antibody potency is dependent on the value of the $k_{on}$ rate for the antibody binding reaction. Thus, an antibody, regardless of affinity for the respective antigen, will exhibit an increase in potency (such as neutralizing ability) where said antibody has a higher $k_{on}$ value, regardless of $K_a$ or $k_{off}$.

In accordance with the methods of the present invention, increased potency of an existing antibody, regardless of its antigen affinity, is achieved through selective changes to one or more of the amino acids present in one or more of the CDR regions of said antibody whereby said amino acid changes have the effect of producing an increase in the $k_{on}$ for said antibody, preferably with an increase in antibody affinity. Higher potency can be achieved with a higher $k_{on}$ value even if the affinity remains the same or is reduced somewhat. Such an antibody is most advantageously produced by synthesis of the required polypeptide chains via synthesis in suitably engineered cells having incorporated therein the appropriate nucleotide sequences coding for the required polypeptide chains containing the altered CDR segments. Also in accordance with the methods of the present invention, a novel antibody having a desirable level of potency, or biological activity, can be prepared de novo by incorporation of selected amino acids at selected locations within the CDR regions of said antibody polypeptide chains using genetically engineered cells as described herein or wholly through chemical synthesis of the required polypeptide chains with subsequent formation of the necessary disulfide bonds.

In this regard, it should be kept clearly in mind that the antibodies produced according to the methods of the present invention may be antibodies possessing tetrameric, dimeric or monomeric structures. Thus, the term "antibody" as used herein includes whole tetrameric antibody molecules, as are commonly found in nature, as well as portions and fragments thereof, including $L_2H_2$, LH, Fab, F(ab')$_2$, and other fragments, the only requirement of such structures being that they retain biological activity as measured by the assays and protocols described herein.

In accordance with the foregoing, the antibodies of the present invention are high affinity monoclonal antibodies. Such antibodies, however, are monoclonal only in the sense that they may be derived from a clone of a single cell type. However, this is not meant to limit them to a particular origin. Such antibodies may readily be produced in cells that commonly do not produce antibodies, such as CHO or COS cells. In addition, such antibodies may be produced in other types of cells, especially mammalian and even plant cells, by genetically engineering such cells to express and assemble the polypeptide light and heavy chains forming the antibody product. In addition, such chains can be chemically synthesized but, since they would be specific for a given antigenic determinant, would still constitute "monoclonal" antibodies within the spirit in which that term is used. Thus, as used herein, the term monoclonal antibody is intended to denote more the specificity and purity of the antibody molecules produced by the methods disclosed herein rather than the mere mechanism used for production of said antibodies.

Also as used herein, the term potency is intended to describe the dependency of the effect of the antibody, when utilized for its intended purpose, on the concentration of such antibody. Thus, potency means biological activity with respect to a given antigen. By way of non-limiting example, the potency, or biological activity, or biological effect, is measured for an anti-RSV antibody, by either the cotton rat procedure or the microneutralization procedure, as described in the Methods section. Conversely, the affinity of an antibody for the antigen is simply a mathematical measure of the ratio of $k_{on}$ to $k_{off}$.

In addition, the affinities ($K_a$) of the antibodies produced according to the methods of the present invention will typically be in the range of $10^{10}$ $M^{-1}$. This range may, for example, be within 10-fold, higher or lower, of $10^{10}$ $M^{-1}$ or be more than 10-fold greater than $10^{10}$ $M^{-1}$ or may even be numerically equal to $10^{10}$ $M^{-1}$. The affinity of the antibody for antigen is proportional to the value of this constant (i.e., the higher the constant, the greater the affinity due to greater concentration of the complex—see the equation for the affinity constant). Such a constant is measured by standard kinetic methodology for antibody reactions (as described in Example 1).

In one embodiment, the antibodies produced according to the methods of the present invention (other than where the term "antibody" means an active portion, fragment or segment, all of which, for purposes of the present disclosure, are considered to be included within the meaning of the term antibody) will commonly comprise a mammalian, preferably a human, constant region and a variable region, said variable region comprising heavy and light chain framework regions and heavy and light chain CDRs, wherein the heavy and light chain framework regions have sequences characteristic of a mammalian antibody, preferably a human antibody, and wherein the CDR sequences are similar to those of an antibody of some species other than a human, preferably a mouse. Where the framework amino acid sequences are characteristic of those of a non-human, the latter is preferably a mouse.

In another embodiment, the antibody is a human antibody wherein the antibody has a $k_{on}$ value as herein described to provide for improved potency.

In addition, antibodies produced according to the present invention will commonly bind the same epitope as prior to applying the methods disclosed herein to increase the $k_{on}$ value. Thus, after applying the methods of the present invention, the antibody will have CDR sequences similar, but not identical, to the CDR sequences prior to application of the methods disclosed herein in that at least one of the CDRs of said antibody will contain a high potency amino acid sequence, such as one selected from SEQ ID NO: 11-34 if the antibody is to be used to neutralize a virus such as RSV.

In keeping with the foregoing, and in order to better describe the sequences disclosed according to the invention with respect to a humanized antibody against RSV, a basic or starting sequence of light and heavy chain variable regions of an antibody, or fragment thereof, whose potency is to be increased, are shown in FIG. 1A (light chain variable region—SEQ ID NO: 1) and FIG. 1B (heavy chain variable region—SEQ ID NO: 2) or an Fab fragment of such an antibody (for example, the sequences of FIG. 2a (light chain variable region—SEQ ID NO: 3) and FIG. 2B (heavy chain variable region—SEQ ID NO: 4). Also in accordance with the invention, specific amino acids different from those of these starting sequences were generated by recombinant methods starting with prepared nucleotide sequences designed to generate said amino acid sequences when expressed in recombinant cells. The products of said cells are the monoclonal antibodies of the present invention. Alternatively, such antibodies can be produced without the use of an engineered or recombinant cell by synthetic means well known in the art.

In one embodiment of the present invention, potency is increased using a neutralizing antibody against respiratory syncytial virus (RSV) having an affinity constant of at least $10^9$ $M^{-1}$, and preferably at least $10^{10}$ $M^{-1}$ (for the F antigen thereof) by increasing the $k_{on}$ value to at least $2.5\times10^5$ $M^{-1}$ $sec^{-1}$. The amino acids present in the CDRs of such an Fab fragment are shown in Table 3 (for example, clone 5).

In general, the approach used to determine affinity and kinetic constants of antibodies before and after application of the methods of the invention to increase the $k_{on}$ value, was to generate nucleotide sequences for the genes expressing the desired antibody chains (in accordance with the present invention) and insert these into vectors that were then used to transform COS-1 cells by standard protocols. The cells were grown in wells and the supernatant sampled and measured for antigen binding using standard ELISA techniques. These polynucleotides were designed so as to provide one or more amino acid replacements in the CDRs that could then be screened for increased $k_{on}$ values, with beneficial replacements (those yielding increased $k_{on}$ values) being selectively combined for increased affinity. These are then subsequently screened for binding affinity for the respective antigen, such as the F antigen of RSV versus the basic or reference structure, thereby determining that no serious change in affinity resulted from the increase in $k_{on}$ values.

In specific embodiments, the present invention relates to an isolated antibody comprising an affinity constant of at least $10^9$ $M^{-1}$, preferably at least $10^{10}$ $M^{-1}$ and most preferably at least $10^{11}$ $M^{-1}$ and wherein the $k_{on}$ is at least about $2.5\times10^5$ $M^{-1}$ $sec^{-1}$, preferably at least about $5\times10^5$ $M^{-1}$ $sec^{-1}$, and most preferably at least $7.5\times10^5$ $M^{-1}$ $sec^{-1}$ (including all combinations thereof).

Also in accordance with the present invention, such isolated antibody may be any kind of antibody already known or newly synthesized and novel. Thus, antibodies produced according to the methods of the present invention will include an antibody selected from the group consisting of a naturally occurring mammalian antibody, naturally occurring human antibodies, naturally occurring mouse antibodies, single chain antibodies, chimeric antibodies (having constant regions of an antibody of one species and variable regions of an antibody of a different species), CDR-grafted antibodies (having the CDR regions of an antibody of one species and the constant and, possibly, framework regions of an antibody of a different species), humanized antibodies (in which selected amino acids, of either the variable framework and/or CDR regions, have been altered so as to be similar to a human antibody despite such sequences being largely derived from a different species, such as a mouse), preferably humanized mouse antibodies, altered mammalian, preferably mouse, most preferably human, antibodies (wherein selected amino acids of an existing antibody have been altered at some point in the polypeptide chain, commonly through the techniques of genetic engineering, to afford antibody structures similar to the antibody structures on which they are based), and wholly synthetic novel antibodies, the latter not previously existing in nature.

The present invention also relates to methods of increasing the potency of one of the aforementioned types of antibodies (as previously described) comprising selectively changing the amino acids within the variable regions of the antibody so as to increase the measured $k_{on}$ value of said antibody with respect to a particular antigen. Of course, the $k_{on}$ value may be different for the same antibody following the same amino acid changes where the reaction is measured using a different antigen or antigenic determinant. However, in such cases, affinities are also likely to change as the identity of the antigenic determinant changes.

Also in accordance with the methods of the present invention the amino acid changes introduced into the sequences of the polypeptides of such antibodies are preferably restricted to the CDR portions of the variable regions of the antibodies although these could involve changes to the framework regions as well.

Although the most advantageous CDR sequences are commonly identified by screening modified clones of antibodies whose potency is to be increased by the methods disclosed herein, once such high potency clones have been identified the resulting antibody is most advantageously produced thereafter through synthesis of the appropriate heavy and light polypeptide chains within suitable animal or plant cells following introduction into such cells of suitable vectors containing the appropriate DNA sequences corresponding to the desired amino acid sequences, taking advantage of the genetic code to design the required nucleotide sequences. As a consequence of this approach, wholly novel antibodies with high potency can be produced at the outset using the amino acid sequence identities suggested by the methods of the present invention without the need to select already existing antibody sequences for modification. Thus, the methods disclosed herein facilitate the production of high potency antibodies of a completely novel structure in that their CDR sequences are high potency CDRs as determined by the methods disclosed herein so as to deliberately increase the $k_{on}$ values of such antibodies and without destroying the specificity and affinity of such antibody for the intended antigenic target.

In one embodiment of the methods of the present invention, an already existing antibody is modified to increase the potency thereof by increasing the $k_{on}$ value. In a preferred embodiment, the antibody is one with high affinities, e.g., at least about $10^9$ $M^{-1}$ or $10^{10}$ $M^{-1}$. The antibody is synthesized, using clones or genetically engineered animal or plant cells, so as to introduce amino acid changes into the heavy and/or light polypeptide chains of said antibody, preferably where said antibody changes are introduced into the complementarity determining regions (CDRs) of said polypeptide chains, to increase the $k_{on}$ value for binding of said antibody to a particular antigen with concomitant increase in the potency of the antibody. Thus, the methods of the present invention are advantageously utilized to produce an antibody molecule wherein the $k_{on}$ value of said antibody following the amino acid changes to its sequence, preferably the variable regions of said sequence, most preferably the CDR portions, is higher than the $k_{on}$ value exhibited by said antibody prior to said amino acid changes when the $k_{on}$ values are measured with respect to the same antigen.

In general, where the methods of the present invention are applied to known antibodies, the $k_{on}$ of said antibodies will be increased by at least 2-fold, preferably at least 5-fold, and most preferably at least 10-fold. More specifically, the $k_{on}$ value of said antibody is increased to at least about $2.5 \times 10^5$ $M^{-1}$ $sec^{-1}$, preferably increased to at least $5 \times 10^5$ $M^{-1}$ $sec^{-1}$, most preferably at least $7.5 \times 10^5$ $M^{-1}$ $sec^{-1}$.

Because the methods disclosed herein are equally effective for designing novel recombinant high potency antibodies previously unknown, the present invention also relates to a method of producing an antibody having a $k_{on}$ value of at least $2.5 \times 10^5$ $M^{-1}$ $sec^{-1}$, comprising preparing an antibody whose polypeptide sequences contain selected amino acids at selected locations, especially within the CDR sequences, and then screening said antibodies for those having a $k_{on}$ value of at least $2.5 \times 10^5$ $M^{-1}$ $sec^{-1}$, or a $k_{on}$ value of at least $5 \times 10^5$ $M^{-1}$ $sec^{-1}$ or even $7.5 \times 10^5$ $M^{-1}$ $sec^{-1}$. Such antibodies will result from the presence of one or more of the high potency CDRs as disclosed herein. Such antibodies are readily screened for high $k_{on}$ values.

The methods of the present invention can be utilized for the production of antibodies with high potency, or antibodies of increased potency, having affinity for any desired antigen, although such antigen is preferably an antigen characteristic of a microorganism, such as a bacterium, virus, or fungus, preferably a virus (for example, respiratory syncytial virus (RSV)).

In another embodiment, the present invention relates to a method of preventing or treating a disease comprising administering to a patient at risk of such disease, or afflicted with such disease, of a therapeutically active amount of an antibody prepared by the methods disclosed herein. Thus, such antibody may be a completely novel antibody or a known and clinically useful antibody whose potency has been increased by application of the methods of the present invention. The disease prevented or treated by antibodies prepared by the methods disclosed herein may commonly be diseases caused by microorganisms, such as bacteria and viruses, preferably viruses and most preferably RSV.

The antibodies thus disclosed will also commonly have framework regions derived from a human antibody but, where not so derived, preferably from a mouse.

In generating the clones, the basic or reference antibody (heavy and light chain variable regions (CDRs plus Framework) shown in FIGS. 1 and 2) was used as the "template" for generating the novel CDR sequences of the antibodies of the present invention, the latter imparting higher $k_{on}$ values. Standard approaches to characterizing and synthesizing the six CDR libraries of single mutations were used (see Wu et al, *Proc. Natl. Acad. Sci.* 95:6037-6042 (1998), the disclosure of which is hereby incorporated by reference in its entirety). The target CDR was first deleted for each of the libraries prior to annealing the nucleotides. For synthesis of the libraries, the CDRs of a reference antibody (see FIG. 2) were defined as in Table 1. Codon based mutagenesis for oligonucleotide synthesis to yield the CDR sequences of the invention was employed (as described above).

Libraries were initially screened by capture lift to identify the highest affinity variants. Subsequently, these clones were further characterized using capture ELISA and by titration on immobilized antigen. Following such screening, the antibodies are then screened for their respective $k_{on}$ values, the positive effects of which are then measured by determination of potency. FIGS. 4 and 5 show additional details on preparation and screening procedures used herein.

TABLE 1

Basic CDR sequences as provided in FIG. 2.

| CDR | Residues of FIG. 2 | Sequence | SEQ ID NO. |
|-----|---------------------|----------|------------|
| L1 | 24-33 | SASSSVGYMH | 5 |
| L2 | 49-55 | DTSKLAS | 6 |
| L3 | 88-96 | FQGSGYPFT | 7 |
| H1 | 31-37 | TSGMSVG | 8 |
| H2 | 52-67 | DIWWDDKKDYNPSLKS | 9 |
| H3 | 100-109 | SMITNWYFDV | 10 |

In accordance with the present invention, DNA from the highest $k_{on}$ variants was sequenced to determine the nature of the beneficial or high potency replacements. After screening, antibodies are then prepared with the high-$k_{on}$ amino acid replacements, either singly or in various combinations, so as to maximize the effects of such substitutions and thereby produce high affinity antibodies also exhibiting high potency.

As a general rule, the most beneficial of high $k_{on}$ CDRs were found to result from amino acid replacements in up to 6 CDRs. Thus, the high potency (i.e., high $k_{on}$) neutralizing antibodies disclosed herein contain amino acid sequences differing from that of the base or reference antibody (for example, as shown in FIGS. 1 and 2) only in complementarity determining regions L1 (or CDRL1), L2 (or CDRL2), L3 (or CDRL3), H1 (or CDRH1) and H3 (or CDRH3).

TABLE 2

Sequences of CDRs tending to induce high potency in antibodies.

| Clone | CDR | High Potency CDR | Sequence | SEQ ID NO. |
|-------|-----|------------------|----------|------------|
| 1 | L1 | — | SASSSVGYMH | 5 |
|   | L2 | X | DTEKLDS | 14 |
|   | L3 | — | FQGSGYPFT | 7 |
|   | H1 | X | TEGMSVG | 24 |
|   | H2 | — | DIWWDDKKDYNPSLKS | 9 |
|   | H3 | X | DMITNEYFDV | 31 |
| 2 | L1 | — | SASSSVGYMH | 5 |
|   | L2 | X | DTEKLAS | 15 |
|   | L3 | — | FQGSGYPFT | 7 |
|   | H1 | X | TAGMSVG | 24 |
|   | H2 | — | DIWWDDKKDYNPSLKS | 9 |
|   | H3 | X | DMIENWYFDV | 32 |
| 3 | L1 | — | SASSSVGYMH | 5 |
|   | L2 | X | DTMKQTS | 16 |
|   | L3 | — | FQGSGYPFT | 7 |
|   | H1 | X | TEGMSVG | 24 |
|   | H2 | — | DIWWDDKKDYNPSLKS | 9 |
|   | H3 | X | DMIENWYFDV | 32 |
| 4 | L1 | — | SASSSVGYMH | 5 |
|   | L2 | X | DTRYLSS | 17 |
|   | L3 | — | FQGSGYPFT | 7 |
|   | H1 | X | TEGMSVG | 24 |
|   | H2 | — | DIWWDDKKDYNPSLKS | 9 |
|   | H3 | X | DMIENWYFDV | 32 |
| 5 | L1 | — | SASSSVGYMH | 5 |
|   | L2 | X | DTEKLAS | 15 |

TABLE 2-continued

Sequences of CDRs tending to induce high potency in antibodies.

| Clone | CDR | High Potency CDR | Sequence | SEQ ID NO. |
|---|---|---|---|---|
| | L3 | – | FQGSGYPFT | 7 |
| | H1 | X | TAGMSVG | 24 |
| | H2 | – | DIWWDDKKDYNPSLKS | 9 |
| | H3 | X | DMITNEYFDV | 31 |
| 6 | L1 | – | SASSSVGYMH | 5 |
| | L2 | X | DTEKLAS | 15 |
| | L3 | X | FQGSEYPFT | 23 |
| | H1 | X | TAGMSVG | 24 |
| | H2 | – | DIWWDDKKDYNPSLKS | 9 |
| | H3 | X | SMITNEYFDV | 33 |
| 7 | L1 | X | SASSRVGYMH | 11 |
| | L2 | X | DTEKLAS | 15 |
| | L3 | – | FQGSGYPFT | 7 |
| | H1 | X | TAGMSVG | 24 |
| | H2 | – | DIWWDDKKDYNPSLKS | 9 |
| | H3 | X | DMITNEYFDV | 31 |
| 8 | L1 | – | SASSSVGYMH | 5 |
| | L2 | X | DTFRLAS | 60 |
| | L3 | – | FQGSGYPFT | 7 |
| | H1 | X | TAGMSVG | 24 |
| | H2 | – | DIWWDDKKDYNPSLKS | 9 |
| | H3 | X | DMITNEYFDV | 31 |
| 9 | L1 | X | SDSSRVGYMH | 12 |
| | L2 | X | DTFYLSS | 61 |
| | L3 | – | FQGSGYPFT | 7 |
| | H1 | X | TAGMSVG | 25 |
| | H2 | X | DIWWDDKKHYNPSLKD | 26 |
| | H3 | X | DMIENEYFDV | 34 |
| 10 | L1 | X | SDSSRVGYMH | 12 |
| | L2 | X | DTRGLES | 18 |
| | L3 | – | FQGSGYPFT | 7 |
| | H1 | X | TAGMSVG | 25 |
| | H2 | X | DIWWDGKKHYNPSLKD | 27 |
| | H3 | X | DMIENEYFDV | 34 |
| 11 | L1 | X | SBSSRVGYMH | 13 |
| | L2 | X | DTMRLAS | 19 |
| | L3 | – | FQGSGYPFT | 7 |
| | H1 | X | TAGMSVG | 25 |
| | H2 | X | DIWWDGKKHYNPSLKD | 27 |
| | H3 | X | DMIENYYFDV | 32 |
| 12 | L1 | X | SDSSRVGYMH | 12 |
| | L2 | X | DTEKLSS | 20 |
| | L3 | – | FQGSGYPFT | 7 |
| | H1 | X | TAGMSVG | 24 |
| | H2 | X | DIWWDGKKHYNPSLKD | 27 |
| | H3 | X | DMIENYYFDV | 32 |
| 13 | L1 | X | SASSRVGYMH | 11 |
| | L2 | X | DTEKLSS | 20 |
| | L3 | – | FQGSGYPFT | 7 |
| | H1 | X | TAGMSVG | 24 |
| | H2 | X | DIWWDGKKDYNPSLKD | 28 |
| | H3 | X | DMIENEYFDV | 34 |
| 14 | L1 | X | SPSSRVGYMH | 13 |
| | L2 | X | DTYRHSS | 21 |
| | L3 | – | FQGSGYPFT | 7 |
| | H1 | X | TAGMSVG | 24 |
| | H2 | X | DIWWDDKKHYNPSLKD | 29 |
| | H3 | X | DMIENWYFDV | 32 |
| 15 | L1 | X | SDSSRVGYMH | 12 |
| | L2 | X | DTMYQSS | 22 |
| | L3 | – | FQGSGYPFT | 7 |
| | H1 | X | TAGMSVG | 24 |
| | H2 | X | DIWWDGKKSYNPSLKD | 30 |
| | H3 | X | DMIENEYFDV | 34 |
| 16 | L1 | – | KCQLSVGYMH | 59 |
| | L2 | – | DTSKLAS | 6 |
| | L3 | – | FQGSGYPFT | 7 |
| | H1 | – | TSGMSVG | 8 |
| | H2 | – | DIWWDDKKDYNPSLKS | 9 |
| | H3 | – | SMITNWYFDV | 10 |
| 17 | L1 | – | SASSSVGYMH | 5 |
| | L2 | X | DTEKLAS | 15 |
| | L3 | X | FQGSEYPFT | 23 |
| | H1 | X | TAGMSVG | 24 |
| | H2 | – | DIWWDDKKDYNPSLKS | 9 |
| | H3 | X | SMITNEYFDV | 33 |
| 18 | L1 | X | LPSSRVGYMH | 56 |
| | L2 | X | DTMYQSS | 22 |
| | L3 | – | FQGSGYPFT | 7 |
| | H1 | X | TAGMSVG | 24 |
| | H2 | X | DIWWDDKKSYNPSLKD | 55 |
| | H3 | X | DMIENEYFDV | 34 |
| 19 | L1 | X | SASSRVGYMH | 11 |
| | L2 | X | DTFELDS | 57 |
| | L3 | – | FQGSGYPFT | 7 |
| | H1 | X | TAGMSVG | 24 |
| | H2 | X | DIWWDDKKHYNPSLKD | 26 |
| | H3 | X | DMIENYEYFDV | 34 |

TABLE 2-continued

Sequences of CDRs tending to induce high potency in antibodies.

| Clone | CDR | High Potency CDR | Sequence | SEQ ID NO. |
|---|---|---|---|---|
| 20 | L1 | X | S[E]S S[R]VGYMH | 13 |
|  | L2 | X | DT[RYQS]S | 58 |
|  | L3 | — | FQGSGYPFT | 7 |
|  | H1 | X | T[A]GMSVG | 24 |
|  | H2 | X | DIWWDDKK[S]YNPSLK[D] | 55 |
|  | H3 | X | [D]MI[E]NWYFDV | 32 |

Thus, for the amino acid sequences of FIG. 3, selected amino acids of the sequence of FIG. 2 were replaced as a means of increasing the potency of the antibody with heavy and light chain sequences shown in FIG. 2.

Selected high $k_{on}$ antibodies (and active fragments thereof) resulting from the methods disclosed herein are shown in Table 2 (all of which have the framework sequences of FIG. 2) where the reference clone is the clone with heavy and light chain variable region sequences shown in FIG. 2 (SEQ ID NO: 3 and 4 for the light and heavy sequences, respectively).

Table 2 indicates the amino acid sequences (all sequences in standard amino acid one letter code) of the high $k_{on}$ CDRs employed in the high potency antibodies prepared according to the methods disclosed herein. In table 2, the locations of key amino acid substitutions made in the corresponding CDRs of table 1 (i.e., locations at which CDRs differ in amino acids) are indicated by a box around the amino acid(s).

In accordance with the invention, by combining such amino acid substitutions so that more than one occurred in the same antibody molecule, it was possible to greatly increase the potency of the antibodies disclosed herein.

In general, there is a correlation between $k_{on}$ and potency of the antibody, with all of the higher $k_{on}$ variants having more than one beneficial or high $k_{on}$ CDR, including having all six CDRs substituted.

In one embodiment, an antibody prepared so as to have increased $k_{on}$ is an RSV-neutralizing antibody, with an affinity of at least $10^9$ M$^{-1}$ and preferably at least $10^{10}$ M$^{-1}$, that is also a humanized antibody that includes a human constant region and a framework for the heavy and light chains wherein at least a portion of the framework is derived from a human antibody (or from a consensus sequence of a human antibody framework).

In another embodiment, all of the framework is derived from a human antibody (or a human consensus sequence).

In another embodiment, an antibody produced according to the present invention, with an affinity of at least $10^9$ M$^{-1}$ and preferably at least $10^{10}$ M$^{-1}$, is a grafted antibody having a human constant region, one or more CDRs that are derived from a non-human antibody in which at least one of the amino acids in at least one of said CDRs is changed and in which all or a portion of the framework is derived from a human antibody (or a consensus sequence of a human antibody framework).

So long as the desired CDR sequences, and the constant and framework sequence are known, genes with the desired sequences can be assembled and, using a variety of vectors, inserted into appropriate cells for expression of the functional tetrameric antibody molecules. Coupling this with the methodology already described, permits the assembly of single mutation libraries wherein the antibodies possess the same sequences as corresponding grafted antibodies and, therefore, the same structure and binding affinities.

The combinations of CDR sequences disclosed in Table 2 can be present in whole tetrameric antibody molecules or in active fragments, such as Fab fragment. The potency data for clones 1 through 15 shown in Table 3 are for Fab fragments while the data for clones 16 and 17 of Table 3 are for whole antibody molecules (clone 16 is MEDI-493 with sequence disclosed in Johnson et al (1997)).

Whole antibody molecules according to the present invention include antibody molecules having heavy chain sequences (variable plus constant region) selected from the group consisting of SEQ ID NO: 37, 39, 41, 43, 45, 47, 49, 51 and 53 and with light chain sequences (variable plus constant region) selected from the group consisting of SEQ ID NO: 38, 40, 42, 44, 46, 48, 50, 52, and 54.

The relatively high $k_{on}$ antibodies of the invention can be present in a relatively pure or isolated form as well as in a supernatant drawn from cells grown in wells or on plates. The antibodies of the invention can thus also be present in the form of a composition comprising the antibody of the invention and wherein said antibody is suspended in a pharmacologically acceptable diluent or excipient. The antibodies of the invention may be present in such a composition at a concentration, or in an amount, sufficient to be of therapeutic or pharmacological value in treating or preventing diseases, (for example, preventing RSV, including the higher incidence of asthma and wheezing that often occur following such infections). Said antibodies may also be present in a composition in a more dilute form.

Consequently, the invention is also directed to providing a method of preventing and/or treating disease, especially viral diseases, most especially respiratory syncytial virus infections, comprising the administering to a patient at risk thereof, or afflicted therewith, of a therapeutically effective amount of the antibody composition described herein.

In one particular embodiment, a high potency neutralizing antibody of the present invention has the heavy chain domain and light chain domain sequences depicted in FIG. 3B (SEQ ID NO:36) and FIG. 3A (SEQ ID NO:35), respectively. The heavy and light chain CDRs are the same as those given in Table 2 for clone 15.

It should be kept in mind that while the increased $k_{on}$ antibodies of the present invention could be assembled from CDR regions and non-CDR regions derived from actual neutralizing antibodies by splicing amino acid segments together (and antibodies so assembled would be within the invention disclosed herein) the antibodies of the present invention are most conveniently prepared by genetically engineering appropriate gene sequences into vectors that may then be transfected into suitable cell lines for eventual expression of the assembled antibody molecules by the engineered cells. In fact, such recombinant procedures were employed to prepare the antibodies disclosed herein. In addition, because the sequences of the chains of the high affinity antibodies are known from the disclosure herein, such antibodies could also be assembled by direct synthesis of the appropriate chains and then allowed to self-assemble into tetrameric antibody structures.

General Materials and Methods

Monoclonal Antibodies. MEDI-493 is an IgG$_1$ (COR)/kappa (K102) humanized MAb (heavy and light chain variable region sequences shown in FIG. 1) containing the antigen binding determinants of murine MAb 1129 [Johnson et al, *J.*

Infect. Dis., 176, 1215-1224 (1997); Beeler and van Wyck Coelingh, J. Virol., 63, 2941-2950 (1989)].

RSV Fusion Inhibition Assay. The ability of the antibodies to block RSV-induced fusion after viral attachment to the cells was determined in a fusion inhibition assay. This assay was identical to the microneutralization assay, except that the cells were infected with RSV (Long) for four hours prior to addition of antibody [Taylor et al, J. Gen. Virol., 73, 2217-2223 (1992)]

BIAcore Analysis. Epitope analysis of the MAbs was performed using a BIAcore biosensor (BIAcore, Piscataway, N.J.) [Karlsson et al, J. Immunol. Methods, 145, 229-240 (1991); Johne, Mol. Biotechnol., 9, 65-71 (1998)] with a plasmin resonance microfluidics system. The antigen used for this assay was a truncated RSV (A2) F protein (amino acids 1-526) expressed in baculovirus. Purified RSV F protein was covalently coupled to an N-hydroxysuccinimide/I-ethyl-3-[3-dimethylaminopropyl]-carbodiimide activated CM5 sensor chip according to the manufacturer's protocol, and unreacted active ester groups were reacted with 1 M ethanolamine. A primary injection of either 1 µM or 10 µM MEDI-493 was followed by an HBSS wash step, and then by a secondary injection of either MEDI-493 or RHSZI9. Sensorgrams were analyzed using BIAevaluation software.

Isothermal Titration Calorimetry. The solution affinity of each MAb for RSV F protein was determined by isothermal titration calorimetry [Wiseman et al, Anal. Biochem., 179, 131-137 (1989)]. A 1.4 mL solution of 4.5 µM RSV F protein was titrated with 5.5 µL injections of 26 µM MEDI-493 or RSHZ19. After each injection of MAb, the amount heat given off, which is proportional to the amount of binding, was measured. The antigen used was an RSV (A2) F protein truncate (amino acids 25-524) expressed in drosophila cells. Titrations were conducted at 44° and 55° C. to achieve optimal signal to noise. Thermal stability of the MAbs and the F protein at these temperatures was demonstrated by circular dichroism unfolding experiments. Affinities were corrected to 37° C. for comparison with in vivo data using the integrated van't Hoff equation [Doyle and Hensley, Methods Enzymol., 295, 88-99 (1998)]. The van't Hoff correction is based solely on the F protein binding enthalpy change which was measured directly by calorimetry. Since the binding enthalpy changes for MEDI-493 and RSHZ19 were found to be very similar, the temperature corrections for their Kds were nearly identical.

Cotton Rat Prophylaxis. In vivo efficacy is determined using the cotton rat model [Prince et al, J. Virol., 55, 517-520 (1985)]. Cotton rats (Sigmodon hispidus, average weight 100 grams) are anesthetized with methoxyflurane, bled, and given 0.1 mL of purified MAb by intramuscular injection (i.m.) at doses of 5, 2.5, 1.25, or 0.625 mg/kg body weight, or bovine serum albumin (BSA) control at 5 mg/kg body weight. Twenty-four hours later animals are again anesthetized, bled for serum MAb concentration determination, and challenged by intranasal instillation (i.n.) of $10^5$ PFU A (Long) or B (18537) strains of RSV. Four days later animals are sacrificed and their lungs were harvested. Lungs are homogenized in 10 parts (wt/vol) of Hanks balanced salt solution and the resultant suspension is used to determine pulmonary viral titers by plaque assay. Serum antibody titers at the time of challenge were determined by an anti-human IgG ELISA.

EXAMPLE 1

Kinetic Analysis of Humanized RSV Mabs by BIAcore™

The kinetics of interaction between high affinity anti-RSV Mabs and the RSV F protein was studied by surface plasmon resonance using a Pharmacia BIAcore™ biosensor. A recombinant baculovirus expressing a C-terminal truncated F protein provided an abundant source of antigen for kinetic studies. The supernatant, which contained the secreted F protein, was enriched approximately 20-fold by successive chromatography on concanavalin A and Q-sepharose columns. The pooled fractions were dialyzed against 10 mM sodium citrate (pH 5.5), and concentrated to approximately 0.1 mg/mi. In a typical experiment, an aliquot of the F-protein (100 ml) was amine-coupled to the BIAcore sensor chip. The amount immobilized gave approximately 2000 response units ($R_{max}$) of signal when saturated with either H1129 or H1308F (prepared as in U.S. Pat. No. 5,824,307, whose disclosure is hereby incorporated by reference). This indicated that there was an equal number of "A" and "C" antigenic sites on the F-protein preparation following the coupling procedure. Two unrelated irrelevant Mabs (RVFV 4D4 and CMV H758) showed no interaction with the immobilized F protein. A typical kinetic study involved the injection of 35 ml of Mab at varying concentrations (25-300 nM) in PBS buffer containing 0.05% Tween-20 (PBS/Tween). The flow rate was maintained at 5 ml/min, giving a 7 min binding phase. Following the injection of Mab, the flow was exchanged with PBS/Tween buffer for 30 min for determining the rate of dissociation. The sensor chip was regenerated between cycles with a 2 min pulse of 10 mM HCI. The regeneration step caused a minimal loss of binding capacity of the immobilized F-protein (4% loss per cycle). This small decrease did not change the calculated values of the rate constants for binding and dissociation (also called the $k_{on}$ and $k_{off}$, respectively).

More specifically, for measurement of $k_{assoc}$ (or $k_{on}$), F protein was directly immobilized by the EDC/NHS method (EDC=N-ethyl-N'-[3-diethylaminopropyl)-carbodiimide). Briefly, 4 µg/ml of F protein in 10 mM NaOAc, pH 4.0 was prepared and about a 30 µl injection gives about 500 RU (response units) of immobilized F protein under the above referenced conditions. The blank flow cell (VnR immobilized-CM dextran surface) was subtracted for kinetic analysis. The column could be regenerated using 100 mM HCI (with 72 seconds of contact time being required for full regeneration). This treatment removed bound Fab completely without damaging the immobilized antigen and could be used for over 40 regenerations. For $k_{on}$ measurements, Fab concentrations were 12.5 nM, 25 nM, 50 nM, 100 nM, 200 nM, and 400 nM. The dissociation phase was analyzed from 230 seconds (30 seconds after start of the dissociation phase) to 900 seconds. Kinetics were analyzed by 1:1 Langmuir fitting (global fitting). Measurements were done in HBS-EP buffer (10 mM HEPES, pH 7.4, 150 mM NaCl, 3 mM EDTA, 0.005% (v/v) Surfactant P20.

For measurements of combinatorial clones, as disclosed herein, the $k_{on}$ and $k_{off}$ were measured separately. The $k_{on}$ was measured at conditions that were the same as those for the single mutation clones and was analyzed similarly.

For measuring $k_{off (or kdissoc)}$ the following conditions were employed. Briefly, 4100 RU of F protein were immobilized (as above) with CM-dextran used as the blank. Here, 3000 RU of Fab was bound (with dissociated Fab high enough to offset machine fluctuation). HBS plus 5 nM F protein (about 350-2000 times higher than the $k_{dissoc}$ or $K_d$—the dissociation equilibrium constant) was used as buffer. The dissociation phase was 6-15 hours at a flow rate of 5 μl/min. Under the conditions used herein, re-binding of the dissociated Fab was minimal. For further details, see the manual with the biosensor.

The binding of the high affinity anti-RSV antibodies to the F protein, or other epitopic sites on RSV, disclosed herein was calculated from the ratio of the first order rate constant for dissociation to the second order rate constant for binding or association ($K_d=k_{diss}/k_{assoc}$). The value for $k_{assoc}$ was calculated based on the following rate equation:

$$dR/dt = k_{assoc}[Mab]R_{max} - (k_{assoc}[Mab]+k_{diss})R$$

where R and $R_{max}$ are the response units at time t and infinity, respectively. A plot of dr/dt as a function of R gives a slope of ($k_{assoc}[Mab]+k_{diss}$)—Since these slopes are linearly related to the [Mab], the value $k_{assoc}$ can be derived from a replot of the slopes versus [Mab]. The slope of the new line is equal to $k_{assoc}$. Although the value of $k_{diss}$ can be extrapolated from the Y-intercept, a more accurate value was determined by direct measurement of $k_{diss}$. Following the injection phase of the Mab, PBS/Tween buffer flows across the sensor chip. From this point, [Mab]=0. The above stated equation for dR/dt thus reduces to:

$$dr/dt = k_{diss}R \text{ or } d/R = k_{diss}dt$$

Integration of this equation then gives:

$$ln(R_0/R_t) = k_{diss}t$$

where $R_0/R_t$ are the response units at time 0 (start of dissociation phase) and t, respectively. Lastly, plotting $ln(R_0/R_t)$ as a function of t gives a slope of $k_{diss}$.

In the preferred embodiment herein, the numerical values from such antibody variants are shown in Table 3.

For the clones in Tables 2 and 3, the reference clone is the Fab fragment with the sequences shown in FIG. 2 and CDRs shown in Table 1. Clones 1-15 are Fab fragments having the framework sequences of FIG. 2 and the indicated CDR combinations of clones 1-15 of Table 2 (where the "X" indicates a high potency CDR (i.e., a CDR whose presence versus the reference sequence results in high potency and higher potency than the reference Fab)). Where no "X" appears next to the CDR of Table 2, the sequence is just the corresponding sequence of the reference Fab (from Table 1 and FIG. 2).

Results in Table 4 compare Fab fragments and full tetrameric antibody molecules as related by $IC_{50}$ values (or the concentration in μg/ml giving 50% inhibition versus controls similar to those for Table 3). Clone 16 of the table is the reference antibody with CDRs described in Table 2.

TABLE 3

Summary of Kinetic Constants for High Potency Antibodies.

| Clone No. | $K_{on} \times 10^5$ (M$^{-1}$s$^{-1}$) | $K_{off} \times 10^{-4}$ (s$^{-1}$) | $EC_{50}$ (nM) |
|---|---|---|---|
| Ref. | 1.85 | 6.5 | 3.52 |
| 1 | 3.65 | 3.26 | 2.26 |
| 2 | 5.31 | 4.22 | 5.05 |
| 3 | 6.05 | 4.22 | 4.70 |
| 4 | 7.57 | 4.62 | 3.55 |
| 5 | 4.16 | 3.06 | 2.61 |
| 6 | 1.85 | 3.20 | 2.88 |
| 7 | 3.70 | 2.51 | 1.59 |
| 8 | 3.75 | 2.73 | 2.67 |
| 9 | 6.63 | 2.82 | 0.29 |
| 10 | 5.27 | 2.99 | 1.06 |
| 11 | 5.71 | 7.17 | 20.9 |
| 12 | 7.9 | 4.53 | 3.24 |
| 13 | 7.43 | 2.30 | 0.81 |
| 14 | 7.35 | 2.50 | 2.23 |
| 15 | 7.81 | 2.80 | 0.56 |
| 16 | 2.04 | 7.35 | 6.12 |
| 17 | 1.09 | 2.49 | 2.7 |

TABLE 4

End Point RSV Microneutralization Titers of High On Rate Mutant IgGs and Fabs

| Type | Clone No. | Mean IC50 μg/ml | Standard IC50 | Fold Difference | Mean IC50 (Control) μg/ml | Standard (Control IC50) | Fold Difference (Control IC50) | Number of Assay Repeats |
|---|---|---|---|---|---|---|---|---|
| IgG | 16 | 0.4527 | 0.208 | — | 0.5351 | 0.238 | — | 8 |
| " | 24 | 0.0625 | 0.0268 | 7 | 0.0645 | 0.0223 | 8 | 3 |
| " | 18 | 0.0342 | 0.022 | 13 | 0.0354 | 0.0187 | 15 | 4 |
| " | 23 | 0.0217 | 0.0331 | 21 | 0.0289 | 0.0110 | 19 | 5 |
| " | 21 | 0.0231 | 0.0141 | 20 | 0.0223 | 0.0083 | 24 | 6 |
| " | 20 | 0.0337 | 0.0309 | 13 | 0.0383 | 0.0283 | 14 | 5 |
| " | 25 | 0.0357 | 0.0316 | 13 | 0.0354 | 0.0261 | 15 | 7 |
| " | 22 | 0.0242 | 0.0163 | 19 | 0.0235 | 0.0076 | 23 | 7 |
| " | 26 | 0.0376 | 0.0268 | 12 | 0.0375 | 0.0213 | 14 | 6 |
| " | 19 | 0.0171 | 0.0018 | 27 | 0.0154 | 0.00417 | 35 | 2 |
| Fab | 12 | 0.157 | — | 3 | 0.125 | — | 4 | 1 |
| " | 27 | 0.0179 | — | 25 | 0.0171 | — | 31 | 1 |
| " | 11 | >1.00 | — | — | >1.00 | — | — | 1 |
| " | 9 | 0.0407 | 0.0112 | 11 | 0.0326 | 0.009 | 16 | 2 |
| " | 28 | 0.177 | — | 3 | 0.157 | — | 34 | 1 |
| " | 13 | 0.0287 | 0.00417 | 16 | 0.0310 | 0.00982 | 17 | 2 |
| " | 10 | 0.0464 | 0.00791 | 10 | 0.0351 | 0.0126 | 15 | 2 |
| " | 15 | 0.0264 | 0.00141 | 17 | 0.0258 | 0.00071 | 21 | 2 |
| " | 29 | 0.0414 | — | 11 | 0.0411 | — | 13 | 1 |

TABLE 4-continued

End Point RSV Microneutralization Titers of High On Rate Mutant IgGs and Fabs

| Type | Clone No. | Mean IC50 µg/ml | Standard IC50 | Fold Difference | Mean IC50 (Control) µg/ml | Standard (Control IC50) | Fold Difference (Control IC50) | Number of Assay Repeats |
|---|---|---|---|---|---|---|---|---|
| " | 14 | 0.120 | 0.0222 | 4 | 0.1022 | 0.0260 | 5 | 2 |
| " | 30 | 0.194 | 0.462 | 2 | 0.176 | 0.0625 | 3 | 2 |

Clones 16 and 17 of Table 3 are actual monoclonal antibodies with the framework sequences of FIG. 1 and constant regions as described in Johnson et al (1997). The framework sequences of these antibodies may differ slightly from those of the Fab fragments.

Clones 18 to 26 of Table 4 are tetrameric antibody molecules similar to clones 16 and 17 but having high potency CDR sequences. Antibody clone 21 has the same CDR sequences as Fab clone 9, antibody clone 22 has the same CDR sequences as Fab clone 10, antibody clone 23 has the same CDR sequences as Fab clone 11, antibody clone 24 has the same CDR sequences as Fab clone 12, antibody clone 25 has the same CDR sequences as Fab clone 13, and antibody clone 26 has the same CDR sequences as Fab clone 15. Antibody clones 18, 19 and 20 of Table 3 are full length tetrameric antibodies with CDR combinations given in Table 2. The framework sequences of these antibodies may differ slightly from those of the Fab fragments.

The underlined amino acids of the CDR sequences of Table 2 represent the amino acid residues located at the key locations within the high potency CDRs of the high potency antibodies produced by the methods of the present invention. For example, to increase the potency of an antibody by producing a higher $k_{on}$ value, the amino acids located at the key positions as taught herein by the bold and underlined residues in Table 1 for the reference antibody would be replaced by the amino acids listed under CDRs in Table 2 (and also bold and underlined). Thus, these one letter codes represent the amino acids replacing the reference amino acids at the key positions (or critical positions) of the CDRs shown in FIG. 2 (residues in bold in the sequences of Table 2) for a reference antibody whose potency is to be increased.

For the clones of Table 4, clone 18 has the full length sequences given by SEQ ID NO: 41 (heavy chain) and 42 (light chain), clone 19 has the full length sequences given by SEQ ID NO: 45 (heavy chain) and 46 (light chain), clone 20 has the full length sequences given by SEQ ID NO: 47 (heavy chain) and 48 (light chain), clone 21 has the full length sequences given by SEQ ID NO: 51 (heavy chain) and 52 (light chain), clone 22 has the full length sequences given by SEQ ID NO: 53 (heavy chain) and 54 (light chain), clone 23 has the full length sequences given by SEQ ID NO: 49 (heavy chain) and 50 (light chain), clone 24 has the full length sequences given by SEQ ID NO: 43 (heavy chain) and 44 (light chain), clone 25 has the full length sequences given by SEQ ID NO: 37 (heavy chain) and 38 (light chain), and clone 26 has the full length sequences given by SEQ ID NO: 39 (heavy chain) and 40 (light chain), Here, clone 18 (IgG) and clone 27 (Fab) have the same CDRs, clone 19 (IgG) and clone 29 (Fab) have the same CDRs, clone 20 (IgG) and clone 28 (Fab) have the same CDRs, clone 21 (IgG) and clone 9 (Fab) have the same CDRs, clone 22 (IgG) and clone 10 (Fab) have the same CDRs, clone 23 (IgG) and clone 11 (Fab) have the same CDRs, clone 24 (IgG) and clone 12 (Fab) have the same CDRs, clone 25 (IgG) and clone 13 (Fab) have the same CDRs, clone 26 (IgG) and clone 15 (Fab) have the same CDRs. Thus, the data of Table 4 correlates the activity of Fab fragments with that of a complete antibody molecule.

Thus, the present invention includes full tetrameric high potency neutralizing antibodies wherein said antibody has a heavy chain amino acid sequence selected from the group consisting of SEQ ID NO: 37, 39, 41, 43, 45, 47, 49, 51 and 53, and a light chain amino acid sequence selected from the group consisting of SEQ ID NO: 38, 40, 42, 44, 46, 48, 50, 52 and 54, preferably where said antibodies are the antibodies of clones 18-26.

The present specification is being filed with a computer readable form (CRF) copy of the Sequence Listing. The CRF entitled 10271155999SeqListing.txt, which was created on Oct. 10, 2008 and is 71,430 bytes in size, is identical to the paper copy of the Sequence Listing and is incorporated herein by reference in its entirety.

EXAMPLE 2

Microneutralization Assay

Neutralization of the antibodies of the present invention were determined by microneutralization assay. This microneutralization assay is a modification of the procedures described by Anderson et al ["Microneutralization test for respiratory syncytial virus based on an enzyme immunoassay, *J. Clin. Microbiol.* 22, 1050-1052 (1985), the disclosure of which is hereby incorporated by reference in its entirety]. The procedure used here is described in Johnson et al [*J. Infectious Diseases*, 180, 35-40 (1999), the disclosure of which is hereby incorporated by reference in its entirety]. Antibody dilutions were made in triplicate using a 96-well plate. Ten $TCID_{50}$ of respiratory syncytial virus (RSV—Long strain) were incubated with serial dilutions of the antibody (or Fabs) to be tested for 2 hours at 37° C. in the wells of a 96-well plate. RSV susceptible HEp-2 cells ($2.5 \times 10^4$) were then added to each well and cultured for 5 days at 37° C. in 5% $CO_2$. After 5 days, the medium was aspirated and cells were washed and fixed to the plates with 80% methanol and 20% PBS. RSV replication was then determined by F protein expression. Fixed cells were incubated with a biotin-conjugated anti-F protein monoclonal antibody (pan F protein, C-site-specific MAb 133-1H) washed and horseradish peroxidase conjugated avidin was added to the wells. The wells were washed again and turnover of substrate TMB (thionitrobenzoic acid) was measured at 450 nm. The neutralizing titer was expressed as the antibody concentration that caused at least 50% reduction in absorbency at 450 nm (the $OD_{450}$) from virus-only control cells.

What is claimed is:

1. An isolated antibody that specifically binds to the F protein of respiratory syncytial virus (RSV), said antibody comprising a light chain variable region (VL) complementarily determining region (CDR)1 having the amino acid sequence of SLSSRVGYMH (SEQ ID NO:12), a VL CDR2 having the amino acid sequence of DTFYLSS (SEQ ID NO:61), a VL CDR3 having the amino acid sequence of FQGSGYPFT (SEQ ID NO:7 ), a heavy chain variable region (VH) CDR1 having the amino acid sequence of TPGMSVG (SEQ ID NO:25), a VH CDR2 having the amino acid sequence of DIWWDDKKHYNPSLKD (SEQ ID NO:26), and a VH CDR3 having the amino acid sequence of DMIFNFYFDV (SEQ ID NO:34).

2. The antibody of claim 1, wherein the antibody is a Fab or F(ab')$_2$ fragment.

3. The antibody of claim 1, wherein the antibody is a whole tetrameric antibody molecule.

4. The antibody of claim 1, wherein the antibody is a humanized antibody.

5. A composition comprising the antibody of claim 1 and a pharmacologically acceptable diluent or excipient.

6. The antibody of claim 1, wherein the antibody is a monoclonal antibody.

7. An isolated antibody that specifically binds to the F protein of a RSV, wherein the antibody:

(a) has a k$_{on}$ of at least 2.5×10$^5$ M$^{-1}$s$^{-1}$ as measured by surface plasmon resonance;

(b) binds to the same epitope of the RSV F antigen as an existing antibody comprising a VH having the amino acid sequence of SEQ ID NO:4 (FIG. 2B) and a VL having the amino acid sequence of SEQ ID NO:3 (FIG. 2A); and (c) comprises the following CDRs with one or more amino acid changes at the underlined and bolded positions in one or more of the CDRs:

| | | |
|---|---|---|
| VH CDR1 | TSGMSVG | (SEQ ID NO:8); |
| VH CDR2 | DIWWDDKKDYNPSLKS | (SEQ ID NO:9); |
| VH CDR3 | SMITNWYFDV | (SEQ ID NO:10); |
| VL CDR1 | SASSSVGYMH | (SEQ ID NO:5); |
| VL CDR2 | DTSKLAS | (SEQ ID NO:6); and |
| VL CDR3 | FQGSGYPFT | (SEQ ID NO:7). |

8. An isolated antibody that specifically binds to the F protein of a RSV, wherein the antibody:

(a) has a k$_{on}$ of at least 2.5×10$^5$ M$^{-1}$ s$^{-1}$ as measured by surface plasmon resonance;

(b) has an EC$_{50}$ of less than 6.0 nM as measured in a microneutralization assay;

(c) binds to the same epitope of the RSV F antigen as an existing antibody comprising a VH having the amino acid sequence of SEQ ID NO:4 (FIG. 2B) and a VL having the amino acid sequence of SEQ ID NO:3 (FIG. 2A); and (d) comprises the following CDRs with one or more amino acid changes at the underlined and bolded positions in one or more of the CDRs:

| | | |
|---|---|---|
| VH CDR1 | TSGMSVG | (SEQ ID NO:8); |
| VH CDR2 | DIWWDDKKDYNPSLKS | (SEQ ID NO:9); |
| VH CDR3 | SMITNWYFDV | (SEQ ID NO:10); |
| VL CDR1 | SASSSVGYMH | (SEQ ID NO:5); |
| VL CDR2 | DTSKLAS | (SEQ ID NO:6); and |
| VL CDR3 | FQGSGYPFT | (SEQ ID NO:7). |

9. The antibody of claim 7, wherein the antibody has a $k_{on}$ of at least $5 \times 10^5$ $M^{-1}$ $s^{-1}$ as measured by surface plasmon resonance.

10. The antibody of claim 8, wherein the antibody has a $k_{on}$ of at least $5 \times 10^5$ $M^{-1}$ $s^{-1}$ as measured by surface plasmon resonance.

11. The antibody of claim 7, wherein the antibody has a $k_{on}$ of at least $7.5 \times 10^5$ $M^{-1}s^{-1}$ as measured by surface plasmon resonance.

12. The antibody of claim 8, wherein the antibody has a $k_{on}$ of at least $7.5 \times 10^5$ $M^{-1}s^{-1}$ as measured by surface plasmon resonance.

13. The antibody of claim 7, wherein the antibody has a $k_{on}$ of between $2.5 \times 10^5$ $M^{-1}s^{-1}$ and $7.5 \times 10^5$ $M^{-1}s^{-1}$ as measured by surface plasmon resonance.

14. The antibody of claim 8, wherein the antibody has a $k_{on}$ of between $2.5 \times 10^5$ $M^{-1}s^{-1}$ and $7.5 \times 10^5$ $M^{-1}s^{-1}$ as measured by surface plasmon resonance.

15. The antibody of claim 7, wherein the antibody has a $k_{on}$ of between $3.7 \times 10^5$ $M^{-1}s^{-1}$ and $7.9 \times 10^5$ $M^{-1}s^{-1}$ as measured by surface plasmon resonance.

16. The antibody of claim 8, wherein the antibody has a $k_{on}$ of between $3.7 \times 10^5$ $M^{-1}s^{-1}$ and $7.9 \times 10^5$ $M^{-1}s^{-1}$ as measured by surface plasmon resonance.

17. The antibody of claim 8, wherein the antibody has an $EC_{50}$ of less than 3.0 nM.

18. The antibody of claim 8, wherein the antibody has an $EC_{50}$ of less than 1.0 nM.

19. The antibody of claim 7, wherein the antibody is a monoclonal antibody.

20. The antibody of claim 9, wherein the antibody is a monoclonal antibody.

21. The antibody of claim 11, wherein the antibody is a monoclonal antibody.

22. The antibody of claim 13, wherein the antibody is a monoclonal antibody.

23. The antibody of claim 15, wherein the antibody is a monoclonal antibody.

24. The antibody of claim 7, wherein the antibody is a Fab or F(ab')$_2$ fragment.

25. The antibody of claim 9, wherein the antibody is a Fab or F(ab')$_2$ fragment.

26. The antibody of claim 11, wherein the antibody is a Fab or F(ab')$_2$ fragment.

27. The antibody of claim 7, wherein the antibody is a whole tetrameric antibody molecule.

28. The antibody of claim 7, wherein the antibody is a humanized antibody.

29. The antibody of claim 9, wherein the antibody is a humanized antibody.

30. The antibody of claim 11, wherein the antibody is a humanized antibody.

31. The antibody of claim 7, wherein the antibody blocks RSV-induced fusion.

32. The antibody of claim 7, wherein the antibody blocks RSV-induced fusion after viral attachment to cells.

33. A composition comprising the antibody of claim 7, and a pharmacologically acceptable diluent or excipient.

34. A composition comprising the antibody of claim 8, and a pharmacologically acceptable diluent or excipient.

35. A composition comprising the antibody of claim 9, and a pharmacologically acceptable diluent or excipient.

36. A composition comprising the antibody of claim 11, and a pharmacologically acceptable diluent or excipient.

37. A composition comprising the antibody of claim 13, and a pharmacologically acceptable diluent or excipient.

38. A composition comprising the antibody of claim 15, and a pharmacologically acceptable diluent or excipient.

* * * * *

UNITED STATES PATENT AND TRADEMARK OFFICE
CERTIFICATE OF CORRECTION

| | | |
|---|---|---|
| PATENT NO. | : 7,700,735 B2 | Page 1 of 1 |
| APPLICATION NO. | : 09/796848 | |
| DATED | : April 20, 2010 | |
| INVENTOR(S) | : Young et al. | |

It is certified that error appears in the above-identified patent and that said Letters Patent is hereby corrected as shown below:

Title Page item (75) Inventors: "Herron Wu" should be corrected to read --Herren Wu--.

Signed and Sealed this
Tenth Day of May, 2011

David J. Kappos
*Director of the United States Patent and Trademark Office*

SEQUENCE LISTING

<160> NUMBER OF SEQ ID NOS: 61

<210> SEQ ID NO 1
<211> LENGTH: 106
<212> TYPE: PRT
<213> ORGANISM: Artificial Sequence
<220> FEATURE:
<223> OTHER INFORMATION: Description of Artificial Sequence: Light chain
      variable region sequence of Medi-493 humanized
      antibody.

<400> SEQUENCE: 1

Asp Ile Gln Met Thr Gln Ser Pro Ser Thr Leu Ser Ala Ser Val Gly
 1               5                  10                  15

Asp Arg Val Thr Ile Thr Cys Lys Cys Gln Leu Ser Val Gly Tyr Met
                20                  25                  30

His Trp Tyr Gln Gln Lys Pro Gly Lys Ala Pro Lys Leu Leu Ile Tyr
            35                  40                  45

Asp Thr Ser Lys Leu Ala Ser Gly Val Pro Ser Arg Phe Ser Gly Ser
        50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys
            100                 105

<210> SEQ ID NO 2
<211> LENGTH: 120
<212> TYPE: PRT
<213> ORGANISM: Artificial Sequence
<220> FEATURE:
<223> OTHER INFORMATION: Description of Artificial Sequence:Heavy chain
      variable region sequence of Medi-493 humanized
      antibody.

<400> SEQUENCE: 2

Gln Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ser
                20                  25                  30

Gly Met Ser Val Gly Trp Ile Arg Gln Pro Pro Gly Lys Ala Leu Glu
            35                  40                  45

Trp Leu Ala Asp Ile Trp Trp Asp Asp Lys Lys Asp Tyr Asn Pro Ser
        50                  55                  60

Leu Lys Ser Arg Leu Thr Ile Ser Lys Asp Thr Ser Lys Asn Gln Val
 65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Trp Tyr Phe Asp Val Trp Gly Ala
            100                 105                 110

Gly Thr Thr Val Thr Val Ser Ser
        115                 120

<210> SEQ ID NO 3
<211> LENGTH: 106
<212> TYPE: PRT
<213> ORGANISM: Artificial Sequence
<220> FEATURE:

<223> OTHER INFORMATION: Description of Artificial Sequence:Light chain
      variable region sequence of a humanized antibody.

<400> SEQUENCE: 3

Asp Ile Gln Met Thr Gln Ser Pro Ser Thr Leu Ser Ala Ser Val Gly
 1               5                  10                  15

Asp Arg Val Thr Ile Thr Cys Ser Ala Ser Ser Ser Val Gly Tyr Met
             20                  25                  30

His Trp Tyr Gln Gln Lys Pro Gly Lys Ala Pro Lys Leu Leu Ile Tyr
         35                  40                  45

Asp Thr Ser Lys Leu Ala Ser Gly Val Pro Ser Arg Phe Ser Gly Ser
 50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Phe Gln Gly Ser Gly Tyr Pro Phe Thr
                 85                  90                  95

Phe Gly Gly Gly Thr Lys Val Glu Ile Lys
            100                 105

<210> SEQ ID NO 4
<211> LENGTH: 120
<212> TYPE: PRT
<213> ORGANISM: Artificial Sequence
<220> FEATURE:
<223> OTHER INFORMATION: Description of Artificial Sequence:Heavy chain
      variable region sequence of a humanized antibody.

<400> SEQUENCE: 4

Gln Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ser
             20                  25                  30

Gly Met Ser Val Gly Trp Ile Arg Gln Pro Pro Gly Lys Ala Leu Glu
         35                  40                  45

Trp Leu Ala Asp Ile Trp Trp Asp Asp Lys Lys Asp Tyr Asn Pro Ser
 50                  55                  60

Leu Lys Ser Arg Leu Thr Ile Ser Lys Asp Thr Ser Lys Asn Gln Val
 65                  70                  75                  80

Val Leu Lys Val Thr Asn Met Asp Pro Ala Asp Thr Ala Thr Tyr Tyr
                 85                  90                  95

Cys Ala Arg Ser Met Ile Thr Asn Trp Tyr Phe Asp Val Trp Gly Gln
            100                 105                 110

Gly Thr Thr Val Thr Val Ser Ser
        115                 120

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence:Light chain
      CDR reference sequence.

<400> SEQUENCE: 5

Ser Ala Ser Ser Ser Val Gly Tyr Met His
 1               5                  10

<210> SEQ ID NO 6
<211> LENGTH: 7
<212> TYPE: PRT

```
<213> ORGANISM: Artificial Sequence
<220> FEATURE:
<223> OTHER INFORMATION: Description of Artificial Sequence:Light chain
      CDR reference sequence.

<400> SEQUENCE: 6

Asp Thr Ser Lys Leu Ala Ser
  1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence:Light chain
      CDR reference sequence.

<400> SEQUENCE: 7

Phe Gln Gly Ser Gly Tyr Pro Phe Thr
  1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence:Heavy Chain
      CDR reference sequence.

<400> SEQUENCE: 8

Thr Ser Gly Met Ser Val Gly
  1               5

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence:Heavy Chain
      CDR reference sequence.

<400> SEQUENCE: 9

Asp Ile Trp Trp Asp Asp Lys Lys Asp Tyr Asn Pro Ser Leu Lys Ser
  1               5                  10                  15

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence:Heavy Chain
      CDR reference sequence.

<400> SEQUENCE: 10

Ser Met Ile Thr Asn Trp Tyr Phe Asp Val
  1               5                  10

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence:High potency
      CDR sequence.

<400> SEQUENCE: 11

Ser Ala Ser Ser Arg Val Gly Tyr Met His
  1               5                  10
```

```
<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence:High potency
      CDR sequence.

<400> SEQUENCE: 12

Ser Leu Ser Ser Arg Val Gly Tyr Met His
 1               5                  10

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence:High potency
      CDR sequence.

<400> SEQUENCE: 13

Ser Pro Ser Ser Arg Val Gly Tyr Met His
 1               5                  10

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence:High potency
      CDR sequence.

<400> SEQUENCE: 14

Asp Thr Phe Lys Leu Thr Ser
 1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence:High potency
      CDR sequence.

<400> SEQUENCE: 15

Asp Thr Phe Lys Leu Ala Ser
 1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence:High potency
      CDR sequence.

<400> SEQUENCE: 16

Asp Thr Tyr Lys Gln Thr Ser
 1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence:High potency
      CDR sequence.
```

```
<400> SEQUENCE: 17

Asp Thr Arg Tyr Leu Ser Ser
  1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence:High potency
      CDR sequence.

<400> SEQUENCE: 18

Asp Thr Arg Gly Leu Pro Ser
  1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence:High potency
      CDR sequence.

<400> SEQUENCE: 19

Asp Thr Met Arg Leu Ala Ser
  1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence:High potency
      CDR sequence.

<400> SEQUENCE: 20

Asp Thr Phe Lys Leu Ser Ser
  1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence:High potency
      CDR sequence.

<400> SEQUENCE: 21

Asp Thr Tyr Arg His Ser Ser
  1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence:High potency
      CDR sequence.

<400> SEQUENCE: 22

Asp Thr Met Tyr Gln Ser Ser
  1               5

<210> SEQ ID NO 23
<211> LENGTH: 9
```

```
<212> TYPE: PRT
<213> ORGANISM: Artificial Sequence
<220> FEATURE:
<223> OTHER INFORMATION: Description of Artificial Sequence:High potency
      CDR sequence.

<400> SEQUENCE: 23

Phe Gln Gly Ser Phe Tyr Pro Phe Thr
 1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence:High potency
      CDR sequence.

<400> SEQUENCE: 24

Thr Ala Gly Met Ser Val Gly
 1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence:High potency
      CDR sequence.

<400> SEQUENCE: 25

Thr Pro Gly Met Ser Val Gly
 1               5

<210> SEQ ID NO 26
<211> LENGTH: 16
<212> TYPE: PRT
<213> ORGANISM: Artificial Sequence
<220> FEATURE:
<223> OTHER INFORMATION: Description of Artificial Sequence:High potency
      CDR sequence.

<400> SEQUENCE: 26

Asp Ile Trp Trp Asp Asp Lys Lys His Tyr Asn Pro Ser Leu Lys Asp
 1               5                  10                  15

<210> SEQ ID NO 27
<211> LENGTH: 16
<212> TYPE: PRT
<213> ORGANISM: Artificial Sequence
<220> FEATURE:
<223> OTHER INFORMATION: Description of Artificial Sequence:High potency
      CDR sequence.

<400> SEQUENCE: 27

Asp Ile Trp Trp Asp Gly Lys Lys His Tyr Asn Pro Ser Leu Lys Asp
 1               5                  10                  15

<210> SEQ ID NO 28
<211> LENGTH: 16
<212> TYPE: PRT
<213> ORGANISM: Artificial Sequence
<220> FEATURE:
<223> OTHER INFORMATION: Description of Artificial Sequence:High potency
      CDR sequence.

<400> SEQUENCE: 28

Asp Ile Trp Trp Asp Gly Lys Lys Asp Tyr Asn Pro Ser Leu Lys Asp
```

```
                1               5                  10                  15

<210> SEQ ID NO 29
<211> LENGTH: 16
<212> TYPE: PRT
<213> ORGANISM: Artificial Sequence
<220> FEATURE:
<223> OTHER INFORMATION: Description of Artificial Sequence:High potency
      CDR sequence.

<400> SEQUENCE: 29

Asp Ile Trp Trp Asp Asp Lys Lys His Tyr Asn Pro Ser Leu Lys Asp
 1               5                  10                  15

<210> SEQ ID NO 30
<211> LENGTH: 16
<212> TYPE: PRT
<213> ORGANISM: Artificial Sequence
<220> FEATURE:
<223> OTHER INFORMATION: Description of Artificial Sequence:High potency
      CDR sequence.

<400> SEQUENCE: 30

Asp Ile Trp Trp Asp Gly Lys Lys Ser Tyr Asn Pro Ser Leu Lys Asp
 1               5                  10                  15

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence:High potency
      CDR sequence.

<400> SEQUENCE: 31

Asp Met Ile Thr Asn Phe Tyr Phe Asp Val
 1               5                  10

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence:High potency
      CDR sequence.

<400> SEQUENCE: 32

Asp Met Ile Phe Asn Trp Tyr Phe Asp Val
 1               5                  10

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence:High potency
      CDR sequence.

<400> SEQUENCE: 33

Ser Met Ile Thr Asn Phe Tyr Phe Asp Val
 1               5                  10

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence:High potency
```

-continued

```
      CDR sequence.

<400> SEQUENCE: 34

Asp Met Ile Phe Asn Phe Tyr Phe Asp Val
 1               5                  10

<210> SEQ ID NO 35
<211> LENGTH: 106
<212> TYPE: PRT
<213> ORGANISM: Artificial Sequence
<220> FEATURE:
<223> OTHER INFORMATION: Description of Artificial Sequence: Light chain
      variable region sequence of high potency
      antibody.

<400> SEQUENCE: 35

Asp Ile Gln Met Thr Gln Ser Pro Ser Thr Leu Ser Ala Ser Val Gly
 1               5                  10                  15

Asp Arg Val Thr Ile Thr Cys Ser Leu Ser Ser Arg Val Gly Tyr Met
                20                  25                  30

His Trp Tyr Gln Gln Lys Pro Gly Lys Ala Pro Lys Leu Leu Ile Tyr
            35                  40                  45

Asp Thr Met Tyr Gln Ser Ser Gly Val Pro Ser Arg Phe Ser Gly Ser
        50                  55                  60

Gly Ser Gly Thr Glu Phe Thr Leu Thr Ile Ser Ser Leu Gln Pro Asp
 65                 70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys
            100                 105

<210> SEQ ID NO 36
<211> LENGTH: 120
<212> TYPE: PRT
<213> ORGANISM: Artificial Sequence
<220> FEATURE:
<223> OTHER INFORMATION: Description of Artificial Sequence: Heavy chain
      variable region sequence of high potency
      antibody.

<400> SEQUENCE: 36

Gln Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ala
                20                  25                  30

Gly Met Ser Val Gly Trp Ile Arg Gln Pro Pro Gly Lys Ala Leu Glu
            35                  40                  45

Trp Leu Ala Asp Ile Trp Trp Asp Gly Lys Lys Ser Tyr Asn Pro Ser
        50                  55                  60

Leu Lys Asp Arg Leu Thr Ile Ser Lys Asp Thr Ser Lys Asn Gln Val
 65                 70                  75                  80

Val Leu Lys Val Thr Asn Met Asp Pro Ala Asp Thr Ala Thr Tyr Tyr
                85                  90                  95

Cys Ala Arg Asp Met Ile Phe Asn Phe Tyr Phe Asp Val Trp Gly Gln
            100                 105                 110

Gly Thr Thr Val Thr Val Ser Ser
        115                 120

<210> SEQ ID NO 37
<211> LENGTH: 450
```

```
<212> TYPE: PRT
<213> ORGANISM: Artificial Sequence
<220> FEATURE:
<223> OTHER INFORMATION: Description of Artificial Sequence: Heavy chain
      of high potency antibody.

<400> SEQUENCE: 37
```

| | | | | | | | | | | | | | | | |
|---|---|---|---|---|---|---|---|---|---|---|---|---|---|---|---|
| Gln | Val | Thr | Leu | Arg | Glu | Ser | Gly | Pro | Ala | Leu | Val | Lys | Pro | Thr | Gln |
| 1 | | | | 5 | | | | | 10 | | | | | 15 | |
| Thr | Leu | Thr | Leu | Thr | Cys | Thr | Phe | Ser | Gly | Phe | Ser | Leu | Ser | Thr | Ala |
| | | | 20 | | | | | 25 | | | | | 30 | | |
| Gly | Met | Ser | Val | Gly | Trp | Ile | Arg | Gln | Pro | Pro | Gly | Lys | Ala | Leu | Glu |
| | | 35 | | | | | 40 | | | | | 45 | | | |
| Trp | Leu | Ala | Asp | Ile | Trp | Trp | Asp | Gly | Lys | Lys | Asp | Tyr | Asn | Pro | Ser |
| | 50 | | | | | 55 | | | | | 60 | | | | |
| Leu | Lys | Asp | Arg | Leu | Thr | Ile | Ser | Lys | Asp | Thr | Ser | Lys | Asn | Gln | Val |
| 65 | | | | | 70 | | | | | 75 | | | | | 80 |
| Val | Leu | Lys | Val | Thr | Asn | Met | Asp | Pro | Ala | Asp | Thr | Ala | Thr | Tyr | Tyr |
| | | | | 85 | | | | | 90 | | | | | 95 | |
| Cys | Ala | Arg | Asp | Met | Ile | Phe | Asn | Phe | Tyr | Phe | Asp | Val | Trp | Gly | Gln |
| | | | 100 | | | | | 105 | | | | | 110 | | |
| Gly | Thr | Thr | Val | Thr | Val | Ser | Ser | Ala | Ser | Thr | Lys | Gly | Pro | Ser | Val |
| | | 115 | | | | | 120 | | | | | 125 | | | |
| Phe | Pro | Leu | Ala | Pro | Ser | Ser | Lys | Ser | Thr | Ser | Gly | Gly | Thr | Ala | Ala |
| | 130 | | | | | 135 | | | | | 140 | | | | |
| Leu | Gly | Cys | Leu | Val | Lys | Asp | Tyr | Phe | Pro | Glu | Pro | Val | Thr | Val | Ser |
| 145 | | | | | 150 | | | | | 155 | | | | | 160 |
| Trp | Asn | Ser | Gly | Ala | Leu | Thr | Ser | Gly | Val | His | Thr | Phe | Pro | Ala | Val |
| | | | | 165 | | | | | 170 | | | | | 175 | |
| Leu | Gln | Ser | Ser | Gly | Leu | Tyr | Ser | Leu | Ser | Ser | Val | Val | Thr | Val | Pro |
| | | | 180 | | | | | 185 | | | | | 190 | | |
| Ser | Ser | Ser | Leu | Gly | Thr | Gln | Thr | Tyr | Ile | Cys | Asn | Val | Asn | His | Lys |
| | | 195 | | | | | 200 | | | | | 205 | | | |
| Pro | Ser | Asn | Thr | Lys | Val | Asp | Lys | Arg | Val | Glu | Pro | Lys | Ser | Cys | Asp |
| | 210 | | | | | 215 | | | | | 220 | | | | |
| Lys | Thr | His | Thr | Cys | Pro | Pro | Cys | Pro | Ala | Pro | Glu | Leu | Leu | Gly | Gly |
| 225 | | | | | 230 | | | | | 235 | | | | | 240 |
| Pro | Ser | Val | Phe | Leu | Phe | Pro | Pro | Lys | Pro | Lys | Asp | Thr | Leu | Met | Ile |
| | | | | 245 | | | | | 250 | | | | | 255 | |
| Ser | Arg | Thr | Pro | Glu | Val | Thr | Cys | Val | Val | Val | Asp | Val | Ser | His | Glu |
| | | | 260 | | | | | 265 | | | | | 270 | | |
| Asp | Pro | Glu | Val | Lys | Phe | Asn | Trp | Tyr | Val | Asp | Gly | Val | Glu | Val | His |
| | | 275 | | | | | 280 | | | | | 285 | | | |
| Asn | Ala | Lys | Thr | Lys | Pro | Arg | Glu | Glu | Gln | Tyr | Asn | Ser | Thr | Tyr | Arg |
| | 290 | | | | | 295 | | | | | 300 | | | | |
| Val | Val | Ser | Val | Leu | Thr | Val | Leu | His | Gln | Asp | Trp | Leu | Asn | Gly | Lys |
| 305 | | | | | 310 | | | | | 315 | | | | | 320 |
| Glu | Tyr | Lys | Cys | Lys | Val | Ser | Asn | Lys | Ala | Leu | Pro | Ala | Pro | Ile | Glu |
| | | | | 325 | | | | | 330 | | | | | 335 | |
| Lys | Thr | Ile | Ser | Lys | Ala | Lys | Gly | Gln | Pro | Arg | Glu | Pro | Gln | Val | Tyr |
| | | | 340 | | | | | 345 | | | | | 350 | | |
| Thr | Leu | Pro | Pro | Ser | Arg | Glu | Glu | Met | Thr | Lys | Asn | Gln | Val | Ser | Leu |
| | | 355 | | | | | 360 | | | | | 365 | | | |
| Thr | Cys | Leu | Val | Lys | Gly | Phe | Tyr | Pro | Ser | Asp | Ile | Ala | Val | Glu | Trp |
| | 370 | | | | | 375 | | | | | 380 | | | | |

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 38
<211> LENGTH: 213
<212> TYPE: PRT
<213> ORGANISM: Artificial Sequence
<220> FEATURE:
<223> OTHER INFORMATION: Description of Artificial Sequence: Light chain
      of high potency antibody.

<400> SEQUENCE: 38

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Phe Lys Leu Ser Ser Gly Val Pro Ser Arg Phe Ser Gly Ser
    50                  55                  60

Gly Ser Gly Thr Glu Phe Thr Leu Thr Ile Ser Ser Leu Gln Pro Asp
65              70                  75                  80

Asp Phe Ala Thr Tyr Tyr Cys Phe Gln Gly Ser Gly Tyr Pro Phe Thr
            85                  90                  95

Phe Gly Gly Gly Thr Lys Val Glu Ile Lys Arg Thr Val Ala Ala Pro
        100                 105                 110

Ser Val Phe Ile Phe Pro Pro Ser Asp Glu Gln Leu Lys Ser Gly Thr
    115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
            165                 170                 175

Thr Leu Thr Leu Ser Lys Ala Asp Tyr Glu Lys His Lys Val Tyr Ala
        180                 185                 190

Cys Glu Val Thr His Gln Gly Leu Ser Ser Pro Val Thr Lys Ser Phe
    195                 200                 205

Asn Arg Gly Glu Cys
210

<210> SEQ ID NO 39
<211> LENGTH: 450
<212> TYPE: PRT
<213> ORGANISM: Artificial Sequence
<220> FEATURE:
<223> OTHER INFORMATION: Description of Artificial Sequence: Heavy chain
      of high potency antibody.

<400> SEQUENCE: 39
```

```
Gln Val Thr Leu Arg Glu Ser Gly Pro Ala Leu Val Lys Pro Thr Gln
  1               5                  10                  15

Thr Leu Thr Leu Thr Cys Thr Phe Ser Gly Phe Ser Leu Ser Thr Ala
             20                  25                  30

Gly Met Ser Val Gly Trp Ile Arg Gln Pro Pro Gly Lys Ala Leu Glu
         35                  40                  45

Trp Leu Ala Asp Ile Trp Trp Asp Gly Lys Ser Tyr Asn Pro Ser
     50                  55                  60

Leu Lys Asp Arg Leu Thr Ile Ser Lys Asp Thr Ser Lys Asn Gln Val
 65              70                  75                  80

Val Leu Lys Val Thr Asn Met Asp Pro Ala Asp Thr Ala Thr Tyr Tyr
                 85                  90                  95

Cys Ala Arg Asp Met Ile Phe Asn Phe Tyr Phe Asp Val Trp Gly Gln
             100                 105                 110

Gly Thr Thr Val Thr Val Ser Ser Ala Ser Thr Lys Gly Pro Ser Val
             115                 120                 125

Phe Pro Leu Ala Pro Ser Ser Lys Ser Thr Ser Gly Gly Thr Ala Ala
         130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
             165                 170                 175

Leu Gln Ser Ser Gly Leu Tyr Ser Leu Ser Ser Val Val Thr Val Pro
             180                 185                 190

Ser Ser Ser Leu Gly Thr Gln Thr Tyr Ile Cys Asn Val Asn His Lys
             195                 200                 205

Pro Ser Asn Thr Lys Val Asp Lys Arg Val Glu Pro Lys Ser Cys Asp
             210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
             245                 250                 255

Ser Arg Thr Pro Glu Val Thr Cys Val Val Val Asp Val Ser His Glu
             260                 265                 270

Asp Pro Glu Val Lys Phe Asn Trp Tyr Val Asp Gly Val Glu Val His
             275                 280                 285

Asn Ala Lys Thr Lys Pro Arg Glu Glu Gln Tyr Asn Ser Thr Tyr Arg
             290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
             325                 330                 335

Lys Thr Ile Ser Lys Ala Lys Gly Gln Pro Arg Glu Pro Gln Val Tyr
             340                 345                 350

Thr Leu Pro Pro Ser Arg Glu Glu Met Thr Lys Asn Gln Val Ser Leu
             355                 360                 365

Thr Cys Leu Val Lys Gly Phe Tyr Pro Ser Asp Ile Ala Val Glu Trp
             370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
             405                 410                 415
```

```
Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 40
<211> LENGTH: 213
<212> TYPE: PRT
<213> ORGANISM: Artificial Sequence
<220> FEATURE:
<223> OTHER INFORMATION: Description of Artificial Sequence: Light chain
      of high potency antibody.

<400> SEQUENCE: 40

Asp Ile Gln Met Thr Gln Ser Pro Ser Thr Leu Ser Ala Ser Val Gly
  1               5                  10                  15

Asp Arg Val Thr Ile Thr Cys Ser Leu Ser Ser Arg Val Gly Tyr Met
                 20                  25                  30

His Trp Tyr Gln Gln Lys Pro Gly Lys Ala Pro Lys Leu Leu Ile Tyr
         35                  40                  45

Asp Thr Met Tyr Gln Ser Ser Gly Val Pro Ser Arg Phe Ser Gly Ser
     50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Phe Gln Gly Ser Gly Tyr Pro Phe Thr
                 85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 41
<211> LENGTH: 450
<212> TYPE: PRT
<213> ORGANISM: Artificial Sequence
<220> FEATURE:
<223> OTHER INFORMATION: Description of Artificial Sequence: Heavy chain
      of high potency antibody.

<400> SEQUENCE: 41

Gln Val Thr Leu Arg Glu Ser Gly Pro Ala Leu Val Lys Pro Thr Gln
  1               5                  10                  15

Thr Leu Thr Leu Thr Cys Thr Phe Ser Gly Phe Ser Leu Ser Thr Ala
                 20                  25                  30
```

-continued

```
Gly Met Ser Val Gly Trp Ile Arg Gln Pro Pro Gly Lys Ala Leu Glu
             35                  40                  45

Trp Leu Ala Asp Ile Trp Trp Asp Asp Lys Lys Ser Tyr Asn Pro Ser
 50                  55                  60

Leu Lys Asp Arg Leu Thr Ile Ser Lys Asp Thr Ser Lys Asn Gln Val
 65                  70                  75                  80

Val Leu Lys Val Thr Asn Met Asp Pro Ala Asp Thr Ala Thr Tyr Tyr
                 85                  90                  95

Cys Ala Arg Asp Met Ile Phe Asn Phe Tyr Phe Asp Val Trp Gly Gln
                100                 105                 110

Gly Thr Thr Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
```

450

<210> SEQ ID NO 42
<211> LENGTH: 213
<212> TYPE: PRT
<213> ORGANISM: Artificial Sequence
<220> FEATURE:
<223> OTHER INFORMATION: Description of Artificial Sequence: Light chain
     of high potency antibody.

<400> SEQUENCE: 42

Asp Ile Gln Met Thr Gln Ser Pro Ser Thr Leu Ser Ala Ser Val Gly
 1               5                  10                  15

Asp Arg Val Thr Ile Thr Cys Leu Pro Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Met Tyr Gln Ser Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 43
<211> LENGTH: 450
<212> TYPE: PRT
<213> ORGANISM: Artificial Sequence
<220> FEATURE:
<223> OTHER INFORMATION: Description of Artificial Sequence: Heavy chain
     of high potency antibody.

<400> SEQUENCE: 43

Gln Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Gly Lys Lys His Tyr Asn Pro Ser
    50                  55                  60

Leu Lys Asp Arg Leu Thr Ile Ser Lys Asp Thr Ser Lys Asn Gln Val

```
                65                  70                  75                  80
Val Leu Lys Val Thr Asn Met Asp Pro Ala Asp Thr Ala Thr Tyr Tyr
                            85                  90                  95

Cys Ala Arg Asp Met Ile Phe Asn Trp Tyr Phe Asp Val Trp Gly Gln
            100                 105                 110

Gly Thr Thr Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 44
<211> LENGTH: 213
<212> TYPE: PRT
<213> ORGANISM: Artificial Sequence
```

```
<220> FEATURE:
<223> OTHER INFORMATION: Description of Artificial Sequence: Light chain
      of high potency antibody.

<400> SEQUENCE: 44

Asp Ile Gln Met Thr Gln Ser Pro Ser Thr Leu Ser Ala Ser Val Gly
 1               5                  10                  15

Asp Arg Val Thr Ile Thr Cys Ser Leu Ser Ser Arg Val Gly Tyr Met
                20                  25                  30

His Trp Tyr Gln Gln Lys Pro Gly Lys Ala Pro Lys Leu Leu Ile Tyr
            35                  40                  45

Asp Thr Phe Lys Leu Ser Ser Gly Val Pro Ser Arg Phe Ser Gly Ser
        50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 45
<211> LENGTH: 450
<212> TYPE: PRT
<213> ORGANISM: Artificial Sequence
<220> FEATURE:
<223> OTHER INFORMATION: Description of Artificial Sequence: Heavy chain
      of high potency antibody.

<400> SEQUENCE: 45

Gln Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ala
                20                  25                  30

Gly Met Ser Val Gly Trp Ile Arg Gln Pro Pro Gly Lys Ala Leu Glu
            35                  40                  45

Trp Leu Ala Asp Ile Trp Trp Asp Asp Lys Lys His Tyr Asn Pro Ser
        50                  55                  60

Leu Lys Asp Arg Leu Thr Ile Ser Lys Asp Thr Ser Lys Asn Gln Val
 65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Phe Tyr Phe Asp Val Trp Gly Gln
            100                 105                 110
```

```
Gly Thr Thr Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 46
<211> LENGTH: 213
<212> TYPE: PRT
<213> ORGANISM: Artificial Sequence
<220> FEATURE:
<223> OTHER INFORMATION: Description of Artificial Sequence: Light chain
      of high potency antibody.

<400> SEQUENCE: 46

Asp Ile Gln Met Thr Gln Ser Pro Ser Thr Leu Ser Ala Ser Val Gly
```

-continued

```
                1               5              10              15
Asp Arg Val Thr Ile Thr Cys Ser Ala Ser Ser Arg Val Gly Tyr Met
                    20                  25                  30

His Trp Tyr Gln Gln Lys Pro Gly Lys Ala Pro Lys Leu Leu Ile Tyr
                    35                  40                  45

Asp Thr Phe Phe Leu Asp Ser Gly Val Pro Ser Arg Phe Ser Gly Ser
                    50                  55                  60

Gly Ser Gly Thr Glu Phe Thr Leu Thr Ile Ser Ser Leu Gln Pro Asp
 65                      70                  75                  80

Asp Phe Ala Thr Tyr Tyr Cys Phe Gln Gly Ser Gly Tyr Pro Phe Thr
                    85                  90                  95

Phe Gly Gly Gly Thr Lys Val Glu Ile Lys Arg Thr Val Ala Ala Pro
                   100                 105                 110

Ser Val Phe Ile Phe Pro Pro Ser Asp Glu Gln Leu Lys Ser Gly Thr
                   115                 120                 125

Ala Ser Val Val Cys Leu Leu Asn Asn Phe Tyr Pro Arg Glu Ala Lys
          130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                   165                 170                 175

Thr Leu Thr Leu Ser Lys Ala Asp Tyr Glu Lys His Lys Val Tyr Ala
              180                 185                 190

Cys Glu Val Thr His Gln Gly Leu Ser Ser Pro Val Thr Lys Ser Phe
              195                 200                 205

Asn Arg Gly Glu Cys
     210
```

<210> SEQ ID NO 47
<211> LENGTH: 450
<212> TYPE: PRT
<213> ORGANISM: Artificial Sequence
<220> FEATURE:
<223> OTHER INFORMATION: Description of Artificial Sequence: Heavy chain
      of high potency antibody.

<400> SEQUENCE: 47

```
                1               5              10              15
Gln Val Thr Leu Arg Glu Ser Gly Pro Ala Leu Val Lys Pro Thr Gln
 1                       5                  10                  15

Thr Leu Thr Leu Thr Cys Thr Phe Ser Gly Phe Ser Leu Ser Thr Ala
                    20                  25                  30

Gly Met Ser Val Gly Trp Ile Arg Gln Pro Pro Gly Lys Ala Leu Glu
                    35                  40                  45

Trp Leu Ala Asp Ile Trp Trp Asp Asp Lys Lys Ser Tyr Asn Pro Ser
                    50                  55                  60

Leu Lys Asp Arg Leu Thr Ile Ser Lys Asp Thr Ser Lys Asn Gln Val
 65                      70                  75                  80

Val Leu Lys Val Thr Asn Met Asp Pro Ala Asp Thr Ala Thr Tyr Tyr
                    85                  90                  95

Cys Ala Arg Asp Met Ile Phe Asn Trp Tyr Phe Asp Val Trp Gly Gln
                   100                 105                 110

Gly Thr Thr Val Thr Val Ser Ser Ala Ser Thr Lys Gly Pro Ser Val
              115                 120                 125

Phe Pro Leu Ala Pro Ser Ser Lys Ser Thr Ser Gly Gly Thr Ala Ala
              130                 135                 140
```

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 48
<211> LENGTH: 213
<212> TYPE: PRT
<213> ORGANISM: Artificial Sequence
<220> FEATURE:
<223> OTHER INFORMATION: Description of Artificial Sequence: Light chain
      of high potency antibody.

<400> SEQUENCE: 48

Asp Ile Gln Met Thr Gln Ser Pro Ser Thr Leu Ser Ala Ser Val Gly
1               5                   10                  15

Asp Arg Val Thr Ile Thr Cys Ser Pro Ser Ser Arg Val Gly Tyr Met
            20                  25                  30

His Trp Tyr Gln Gln Lys Pro Gly Lys Ala Pro Lys Leu Leu Ile Tyr
        35                  40                  45

```
Asp Thr Arg Tyr Gln Ser Ser Gly Val Pro Ser Arg Phe Ser Gly Ser
         50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Phe Gln Gly Ser Gly Tyr Pro Phe Thr
                 85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
        210

<210> SEQ ID NO 49
<211> LENGTH: 450
<212> TYPE: PRT
<213> ORGANISM: Artificial Sequence
<220> FEATURE:
<223> OTHER INFORMATION: Description of Artificial Sequence: Heavy chain
      of high potency antibody.

<400> SEQUENCE: 49

Gln Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Pro
             20                  25                  30

Gly Met Ser Val Gly Trp Ile Arg Gln Pro Pro Gly Lys Ala Leu Glu
         35                  40                  45

Trp Leu Ala Asp Ile Trp Trp Asp Gly Lys Lys His Tyr Asn Pro Ser
 50                  55                  60

Leu Lys Asp Arg Leu Thr Ile Ser Lys Asp Thr Ser Lys Asn Gln Val
 65                  70                  75                  80

Val Leu Lys Val Thr Asn Met Asp Pro Ala Asp Thr Ala Thr Tyr Tyr
                 85                  90                  95

Cys Ala Arg Asp Met Ile Phe Asn Trp Tyr Phe Asp Val Trp Gly Gln
            100                 105                 110

Gly Thr Thr Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
```

```
                185             190
Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
        210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 50
<211> LENGTH: 213
<212> TYPE: PRT
<213> ORGANISM: Artificial Sequence
<220> FEATURE:
<223> OTHER INFORMATION: Description of Artificial Sequence: Light chain
      of high potency antibody.

<400> SEQUENCE: 50

Asp Ile Gln Met Thr Gln Ser Pro Ser Thr Leu Ser Ala Ser Val Gly
1               5                   10                  15

Asp Arg Val Thr Ile Thr Cys Ser Pro Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Met Arg Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80
```

```
Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
210

<210> SEQ ID NO 51
<211> LENGTH: 450
<212> TYPE: PRT
<213> ORGANISM: Artificial Sequence
<220> FEATURE:
<223> OTHER INFORMATION: Description of Artificial Sequence: Heavy chain
      of high potency antibody.

<400> SEQUENCE: 51

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Pro
                20                  25                  30

Gly Met Ser Val Gly Trp Ile Arg Gln Pro Pro Gly Lys Ala Leu Glu
            35                  40                  45

Trp Leu Ala Asp Ile Trp Trp Asp Asp Lys Lys His Tyr Asn Pro Ser
        50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Phe Tyr Phe Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220
```

```
Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 52
<211> LENGTH: 213
<212> TYPE: PRT
<213> ORGANISM: Artificial Sequence
<220> FEATURE:
<223> OTHER INFORMATION: Description of Artificial Sequence: Light chain
      of high potency antibody.

<400> SEQUENCE: 52

Asp Ile Gln Met Thr Gln Ser Pro Ser Thr Leu Ser Ala Ser Val Gly
1               5                   10                  15

Asp Arg Val Thr Ile Thr Cys Ser Leu Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Phe Tyr Leu Ser Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
```

-continued

```
                115                 120                 125
Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
        180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 53
<211> LENGTH: 450
<212> TYPE: PRT
<213> ORGANISM: Artificial Sequence
<220> FEATURE:
<223> OTHER INFORMATION: Description of Artificial Sequence: Heavy chain
      of high potency antibody.

<400> SEQUENCE: 53

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Pro
                20                  25                  30

Gly Met Ser Val Gly Trp Ile Arg Gln Pro Pro Gly Lys Ala Leu Glu
            35                  40                  45

Trp Leu Ala Asp Ile Trp Trp Asp Gly Lys Lys His Tyr Asn Pro Ser
    50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Phe Tyr Phe Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
    195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255
```

```
Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Glu Glu Met Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
    450

<210> SEQ ID NO 54
<211> LENGTH: 213
<212> TYPE: PRT
<213> ORGANISM: Artificial Sequence
<220> FEATURE:
<223> OTHER INFORMATION: Description of Artificial Sequence: Light chain
      of high potency antibody.

<400> SEQUENCE: 54

Asp Ile Gln Met Thr Gln Ser Pro Ser Thr Leu Ser Ala Ser Val Gly
  1               5                  10                  15

Asp Arg Val Thr Ile Thr Cys Ser Leu Ser Arg Val Gly Tyr Met
                20                  25                  30

His Trp Tyr Gln Gln Lys Pro Gly Lys Ala Pro Lys Leu Leu Ile Tyr
            35                  40                  45

Asp Thr Arg Gly Leu Pro Ser Gly Val Pro Ser Arg Phe Ser Gly Ser
        50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160
```

```
Ser Val Thr Glu Gln Asp Ser Lys Asp Ser Thr Tyr Ser Leu Ser Ser
            165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210

<210> SEQ ID NO 55
<211> LENGTH: 16
<212> TYPE: PRT
<213> ORGANISM: Artificial Sequence
<220> FEATURE:
<223> OTHER INFORMATION: Description of Artificial Sequence:High potency
      CDR sequence.

<400> SEQUENCE: 55

Asp Ile Trp Trp Asp Asp Lys Lys Ser Tyr Asn Pro Ser Leu Lys Asp
 1               5                  10                  15

<210> SEQ ID NO 56
<211> LENGTH: 10
<212> TYPE: PRT
<213> ORGANISM: Artificial Sequence
<220> FEATURE:
<223> OTHER INFORMATION: Description of Artificial Sequence:High potency
      CDR sequence.

<400> SEQUENCE: 56

Leu Pro Ser Ser Arg Val Gly Tyr Met His
 1               5                  10

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence:High potency
      CDR sequence.

<400> SEQUENCE: 57

Asp Thr Phe Phe Leu Asp Ser
 1               5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence:High potency
      CDR sequence.

<400> SEQUENCE: 58

Asp Thr Arg Tyr Gln Ser Ser
 1               5

<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence:Light Chain
      CDR reference sequence.

<400> SEQUENCE: 59
```

```
Lys Cys Gln Leu Ser Val Gly Tyr Met His
 1               5                   10

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence:High potency
      CDR sequence.

<400> SEQUENCE: 60

Asp Thr Phe Arg Leu Ala Ser
 1               5

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence:High potency
      CDR sequence.

<400> SEQUENCE: 61

Asp Thr Phe Tyr Leu Ser Ser
 1               5
```